US010081628B2

(12) United States Patent
Tao et al.

(10) Patent No.: US 10,081,628 B2
(45) Date of Patent: Sep. 25, 2018

(54) APOPTOSIS-INDUCING AGENTS FOR THE TREATMENT OF CANCER AND IMMUNE AND AUTOIMMUNE DISEASES

(71) Applicant: AbbVie Inc., North Chicago, IL (US)

(72) Inventors: Zhi-Fu Tao, Vernon Hills, IL (US); Xilu Wang, Libertyville, IL (US); Michael Wendt, Vernon Hills, IL (US); Andrew Souers, Evanston, IL (US); Andrew Judd, Grayslake, IL (US); Aaron Kunzer, Arlington Heights, IL (US); Gerard Sullivan, Lake Villa, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/276,872

(22) Filed: Sep. 27, 2016

(65) Prior Publication Data

US 2017/0008891 A1 Jan. 12, 2017

Related U.S. Application Data

(60) Continuation of application No. 14/789,449, filed on Jul. 1, 2015, which is a division of application No. 14/176,506, filed on Feb. 10, 2014, now abandoned.

(60) Provisional application No. 61/781,070, filed on Mar. 14, 2013.

(51) Int. Cl.

| | |
|---|---|
| ***C07D 471/04*** | (2006.01) |
| ***A61K 31/496*** | (2006.01) |
| ***A61K 31/5377*** | (2006.01) |
| ***A61K 45/06*** | (2006.01) |

(52) U.S. Cl.

CPC .......... *C07D 471/04* (2013.01); *A61K 31/496* (2013.01); *A61K 31/5377* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 6,004,973 | A | 12/1999 | Guitard et al. |
| 6,720,338 | B2 | 4/2004 | Augeri et al. |
| 6,787,534 | B2 | 9/2004 | Haneda et al. |
| 6,858,638 | B2 | 2/2005 | Damour et al. |
| 7,390,799 | B2 | 6/2008 | Bruncko et al. |
| 7,504,512 | B2 | 3/2009 | Augeri et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,642,260 | B2 | 1/2010 | Bruncko et al. |
| 7,709,467 | B2 | 5/2010 | Bruncko et al. |
| 7,754,886 | B2 | 7/2010 | Augeri et al. |
| 7,767,684 | B2 | 8/2010 | Bruncko et al. |
| 7,947,706 | B2 | 5/2011 | Tabart et al. |
| 8,084,607 | B2 | 12/2011 | Bruncko et al. |
| 8,173,811 | B2 | 5/2012 | Bruncko et al. |
| 8,187,836 | B2 | 5/2012 | Hsieh |
| 8,354,404 | B2 | 1/2013 | Bruncko et al. |
| 8,546,399 | B2 | 10/2013 | Bruncko et al. |
| 2002/0055631 | A1 | 5/2002 | Augeri et al. |
| 2003/0144507 | A1 | 7/2003 | Haneda et al. |
| 2003/0236236 | A1 | 12/2003 | Chen et al. |
| 2005/0059722 | A1 | 3/2005 | Damour et al. |
| 2005/0101628 | A1 | 5/2005 | Jiao et al. |
| 2005/0159427 | A1 | 7/2005 | Bruncko et al. |
| 2005/0163835 | A1 | 7/2005 | Gellert et al. |
| 2005/0208082 | A1 | 9/2005 | Papas et al. |
| 2006/0128706 | A1 | 6/2006 | Bruncko et al. |
| 2007/0015787 | A1 | 1/2007 | Bruncko et al. |
| 2007/0027135 | A1 | 2/2007 | Bruncko et al. |
| 2007/0072860 | A1 | 3/2007 | Bruncko et al. |
| 2008/0076779 | A1 | 3/2008 | Elmore et al. |
| 2008/0182845 | A1 | 7/2008 | Bardwell et al. |
| 2008/0300267 | A1 | 12/2008 | Okram et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |

(Continued)

FOREIGN PATENT DOCUMENTS

| | | | |
|---|---|---|---|
| CN | 1561201 | A | 1/2005 |
| CN | 101175738 | A | 5/2008 |

(Continued)

OTHER PUBLICATIONS

Bardwell et al., "The Bcl-2 Family Antagonist ABT-737 Significantly Inhibits Multiple Animal Models of Autoimmunity," Journal of Immunology, 2009, vol. 182 (12), pp. 7482-7489.

(Continued)

*Primary Examiner* — Emily A Bernhardt

(57) ABSTRACT

Disclosed herein are compounds that inhibit the activity of anti-apoptotic Bcl-2 proteins, compositions containing the compounds and methods of treating diseases using the compounds. One embodiment of such compounds is 4-(4-{[2-(4-chloro-2-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide.

1 Claim, No Drawings

Specification includes a Sequence Listing.

(56) References Cited

U.S. PATENT DOCUMENTS

| | | | |
|---|---|---|---|
| 2009/0137457 | A1 | 5/2009 | Harbeson |
| 2009/0176785 | A1 | 7/2009 | Bardwell et al. |
| 2009/0239259 | A1 | 9/2009 | Hsieh |
| 2010/0022773 | A1 | 1/2010 | Bruncko et al. |
| 2010/0152183 | A1 | 6/2010 | Bruncko et al. |
| 2010/0160322 | A1 | 6/2010 | Bruncko et al. |
| 2010/0184750 | A1 | 7/2010 | Hexamer et al. |
| 2010/0184766 | A1 | 7/2010 | Kunzer et al. |
| 2010/0227838 | A1 | 9/2010 | Shah et al. |
| 2010/0297194 | A1 | 11/2010 | Catron et al. |
| 2010/0298321 | A1 | 11/2010 | Bruncko et al. |
| 2010/0298323 | A1 | 11/2010 | Bruncko et al. |
| 2010/0305122 | A1 | 12/2010 | Bruncko et al. |
| 2010/0310648 | A1 | 12/2010 | Packhaeuser et al. |
| 2011/0124628 | A1 | 5/2011 | Bruncko et al. |
| 2012/0108590 | A1 | 5/2012 | Birtalan et al. |
| 2012/0129853 | A1 | 5/2012 | Elmore et al. |
| 2012/0157470 | A1 | 6/2012 | Catron et al. |
| 2012/0190688 | A1 | 7/2012 | Bruncko et al. |
| 2012/0277210 | A1 | 11/2012 | Catron et al. |

FOREIGN PATENT DOCUMENTS

| | | | |
|---|---|---|---|
| EA | 012983 | B1 | 2/2010 |
| EP | 1880715 | A1 | 1/2008 |
| EP | 1796642 | B1 | 5/2008 |
| RU | 2159107 | C2 | 11/2000 |
| RU | 2001103044 | A | 8/2003 |
| RU | 2239631 | C2 | 11/2004 |
| RU | 2004130280 | A | 6/2005 |
| RU | 2318518 | C2 | 3/2008 |
| RU | 2387653 | C2 | 4/2010 |
| WO | 1995007271 | A1 | 3/1995 |
| WO | 1997010223 | A1 | 3/1997 |
| WO | 1997029131 | A1 | 8/1997 |
| WO | 2000001389 | A1 | 1/2000 |
| WO | 2000057854 | A2 | 10/2000 |
| WO | 2001000175 | A1 | 1/2001 |
| WO | 2002024636 | A2 | 3/2002 |
| WO | 2002066470 | A1 | 8/2002 |
| WO | 2002098848 | A1 | 12/2002 |
| WO | 2003028705 | A1 | 4/2003 |
| WO | 2003072108 | A1 | 9/2003 |
| WO | 2005049593 | A2 | 6/2005 |
| WO | 2005049594 | A1 | 6/2005 |
| WO | 2005099353 | A2 | 10/2005 |
| WO | 2006008754 | A1 | 1/2006 |
| WO | 2007002325 | A1 | 1/2007 |
| WO | 2007040650 | A2 | 4/2007 |
| WO | 2006124863 | A1 | 11/2007 |
| WO | 2008030836 | A2 | 3/2008 |
| WO | 2008124878 | A1 | 10/2008 |
| WO | 2009045464 | A1 | 4/2009 |
| WO | 2009073835 | A1 | 6/2009 |
| WO | 2010041051 | A1 | 4/2010 |
| WO | 2010065824 | A2 | 6/2010 |
| WO | 2010065865 | A2 | 6/2010 |
| WO | 2010072734 | A2 | 7/2010 |
| WO | 2010077740 | A2 | 7/2010 |
| WO | 2010083441 | A2 | 7/2010 |
| WO | 2010138588 | A2 | 12/2010 |
| WO | 2010143074 | A2 | 12/2010 |
| WO | 2011068560 | A1 | 6/2011 |
| WO | 2011068561 | A1 | 6/2011 |
| WO | 2011149492 | A1 | 12/2011 |
| WO | 2012058392 | A1 | 5/2012 |
| WO | 2012071336 | A1 | 5/2012 |
| WO | 2012071374 | A1 | 5/2012 |
| WO | 2012121758 | A1 | 9/2012 |

OTHER PUBLICATIONS

Becker et al., "Azaadamantane Benzamide 5-HT4 Agonists: Gastrointestinal Prokinetic SC-54750," Bioorganic and Medicinal Chemistry Letters, 2004, vol. 14 (22), pp. 5509-5512.

Berge et al., "Pharmaceutical Salts," Journal of Pharmaceutical Sciences, 1977, vol. 66 (1), pp. 1-19.

Beylot et al., "In Vivo Studies of Intrahepatic Metabolic Pathways," Diabetes & Metabolism, 1997, vol. 23 (3), pp. 251-257.

Blagojevic et al., "Role of Heavy Water in Boron Neutron Capture Therapy," Topics in Dosimetry & Treatment Planning for Neutron Capture Therapy, 1994, pp. 125-134.

Blake et al., "Studies With Deuterated Drugs," Journal of Pharmaceutical Sciences, 1975, vol. 64 (3), pp. 367-391.

Brickner et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

Bruncko et al., "Studies Leading to Potent, Dual Inhibitors of Bcl-2 and Bcl-xL," Journal of Medicinal Chemistry, 2007, vol. 50 (4), pp. 641-662.

Burger's Medicinal Chemistry and Drug Discovery, edited by Manfred E. Wolff, $5^{th}$ Edition, Part 1, 1995, pp. 975-977.

Caira, M.R., "Crystalline Polymorphism of Organic Compounds," 1998, vol. 198, pp. 163-208.

Cancer [online], [retrieved on Jul. 6, 2007]. Retrieved from the internet, <URL: http://www.nlm.nih.gov/medlineplus/cancer.html>, 8 pgs.

Cancer [online], [retrieved on Jul. 6, 2007]. Retrieved from the internet, <URL: http:// en.wikipedia.org/wiki/Cancer>, 34 pgs.

Certo et al., "Mitochondria Primed by Death Signals Determine Cellular Addiction to Antiapoptotic BCL-2 Family Members," Cancer Cell, 2006, vol. 9 (5), pp. 351-365.

Cross et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Crowley et al., "Pharmaceutical Applications of Hot-Melt Extrusion: Part 1," Drug Development and Industrial Pharmacy, 2007, vol. 33 (9), pp. 909-926.

Czajka et al., "Effect of Deuterium Oxide on the Reproductive Potential of Mice," Annals New York Academy of Sciences, 1960, vol. 84, pp. 770-779.

Czajka et al., "Physiological Effects of Deuterium on Dogs," American Journal of Physiology, 1961, vol. 201 (2), pp. 357-362.

Del Gaizo Moore et al., "BCL-2 Dependence and ABT-737 Sensitivity in Acute Lymphoblastic Leukemia," Blood, 2008, vol. 111 (4), pp. 2300-2309.

Durocher et al., "High-Level and High-Throughput Recombinant Protein Production by Transient Transfection of Suspension-Growing Human 293-EBNA1 Cells," Nucleic Acids Research, 2002, vol. 30 (2), pp. e9.

Eliel et al., "Stereochemistry of Organic Compounds," 1994, John Wiley & Sons, Inc., New York, Table of Contents. 6 pgs.

Fairhurst et al., "Systemic IFN-Alpha Drives Kidney Nephritis in B6.Sle123 Mice," European Journal of Immunology, 2008, vol. 38 (7), pp. 1948-1960.

Foster et al., "Deuterium Isotope Effects in the Metabolism of Drugs and Xenobiotics: Implications for Drug Design," Advances in Drug Research, 1985, vol. 14, pp. 2-36.

Gelfand et al., "Therapeutic Studies in NZB/W Mice II. Relative Efficacy of Azathioprine, Cyclophosphamide and Methylprednisolone," Arthritis and Rheumatism,1972, vol. 15 (3), pp. 247-252.

Golub et al., "Molecular Classification of Cancer: Class Discovery and Class Prediction by Gene Expression Monitoring", Science (1999), vol. 286, pp. 531-537.

Guo et al., "Relationship between the Expression of bcl-2. Fas/FasL and the Apoptosis of Peripheral Lymphocytes in Patients with Systemic lupus Erythematosus," Chinese Journal of Dermatology, 2001, vol. 34 (1), pp. 25 and 27.

Gupta, P. K., "Solutions and Phase Equilibria", Remington, The Science and Practice of Pharmacy, 21st Edition, Chapter 16, (2005) pp. 211-230.

Hanahan et al., "The Hallmarks of Cancer," Cell, 2000, vol. 100 (1), pp. 57-70.

(56) References Cited

OTHER PUBLICATIONS

Harada et al., "Survival Factor-Induced Extracellular Signal-Regulated Kinase Phosphorylates BIM, Inhibiting its Association with BAX and Proapoptotic Activity," Proceedings of the National Academy of Sciences, 2004, vol. 101 (43), pp. 15313-15317.
Hoepfner et al., eds., "Fiedler Encyclopedia of Excipients for Pharmaceuticals, Cosmetics and Related Areas," 5th Edition, Editio Cantor Verlag Aulendorf, 2002, Table of Contents, 6 pgs.
Holzelova et al., "Autoimmune Lymphoproliferative Syndrome with Somatic Fas Mutations," New England Journal of Medicine, 2004, vol. 351 (14), pp. 1409-1418.
Hovorka et al., "Oxidative Degradation of Pharmaceuticals: Theory, Mechanisms and Inhibition," J. Pharm. Sciences, 2001, vol. 90 (3), 253-269.
Humerickhouse, R., "Clinical Activity of the Potent and Selective Bcl-2 Inhibitor ABT-199: Proving the Concept," Symposium presentation, Apr. 9, 2013, AACR Annual Meeting (Wash. DC), pp. 1-31.
Jones et al., "Effects of Substituent Modification on Face Selection in Reduction," Journal of Organic Chemistry, 1998, vol. 63 (8), pp. 2758-2760.
Kato et al., "Synthesis of Deuterated Mosapride Citrate," Journal of Labelled Compounds and Radiopharmaceuticals, 1995, vol. 36 (10), pp. 927-932.
Kayagaki et al., "BAFF/BLyS Receptor 3 Binds the B Cell Survival Factor BAFF Ligand Through a Discrete Surface Loop and Promotes Processing of NF-kB2," Immunity, 2002, vol. 10, pp. 515-524.
Kibbe, A.H., Handbook of Pharmaceutical Excipients, Third Edition, 2000, American Pharmaceutical Association, Table of Contents, 4 pgs.
Klein et al., "The Tablet Formulation of Lopinavir/Ritonavir Provides Similar Bioavailability to the Soft-Gelatin Capsule Formulation With Less Pharmacokinetic Variability and Diminished Food Effect," Journal of Acquired Immune Deficiency Syndromes, 2007, vol. 44 (4), pp. 401-410.
Korolkovas, A., "Development of Drugs" in: Essentials of Medicinal Chemistry, Second Edition, John Wiley and Sons, 1988, pp. 53-139.
Kushner et al., "Pharmacological uses and perspectives of heavy water and deuterated compounds," Canadian Journal of Physiology and Pharmacology, 1999, vol. 77 (2), pp. 79-88.
Kwok et al., "Dysfunctional Interferon-a Production by Peripheral Plasmacytoid Dendritic Cells upon Toll-like Receptor-9 Stimulation in Patients with Systemic Lupus Erythematosus," Arthritis Research & Therapy, 2008, vol. 10 (2), 11 pgs.
Lala et al., "Role of nitric oxide in tumor progression: Lessons from experimental tumors." Cancer and Metastasis Reviews, 1998, vol. 17(1 ), pp. 91-106.
Laurent et al., "Synthesis of "Trioxaquantel" Derivatives as Potential New Antischistosomal Drugs," European Journal of Organic Chemistry, 2008, vol. 5, pp. 895-913.
Leuner et al., "Improving Drug Solubility for Oral Delivery Using Solid Dispersions," European Journal of Pharmaceutics and Biopharmaceutics: Official Journal of Arbeitsgemeinschaft Fur Pharmazeutische Verfahrenstechnik E.V., 2000, vol. 50 (1), pp. 47-60.
Liao, G., "ABT-199 BH-3 Mimetic Enters Phase Ia Trial for Chronic Lymphocytic Leukemia", [Asian Scientist Magazine online], [retrieved on Aug. 12, 2011]. Retrieved from the Internet <URL: http://www.asianscientist.com/tech-pharma/abt-1 99-bh-3-mimetic-wehiphase-ia-trial-chronic-lymphocytic-leukemia>, 2 pgs.
Liu et al., "What do Mouse Models Teach us about Human SLE?," Clinical Immunology, 2006, vol. 119 (2), pp. 123-130.
Lizondo et al., "Linezolid: Oxazolidinone Antibacterial," Drugs of the Future, 1996, vol. 21 (11), pp. 1116-1123.
Mallesham et al., "Highly Efficient Cul-Catalyzed Coupling of Aryl Bromides with Oxazolidinones Using Buchwald's Protocol: A Short Route to Linezolid and Toloxatone," Organic Letters, 2003, vol. 5 (7), pp. 963-965.
Marquina et al., "Inhibition of B Cell Death Causes the Development of an IgA Nephropathy in (New Zealand White x C57BL/6) $F_1$-bcl-2 Transgenic Mice," Journal of Immunology, 2004, vol. 172 (11), pp. 7177-7185.
Mason et al, "Programmed Anuclear Cell Death Delimits Platelet Life Span," Cell, 2007, vol. 128 (6), pp. 1173-1186.
Mathian et al., "IFN-a induces Early Lethal Lupus in Preautoimmune (New Zealand Black x New Zealand White) $F_1$ but not in BALB/c Mice," Journal of Immunology, 2005, vol. 174 (5), pp. 2499-2506.
Mizushima et al., "pEF-BOS, a Powerful Mammalian Expression Vector," Nucleic Acids Research, 1990, vol. 18 (17), pp. 5322.
Modern Pharmaceutics, edited by Gilbert S. Banker and Christopher T. Rhodes, 3rd Edition, 1996, pp. 451 and 596.
Moschwitzer et al., "Development of an Intravenously Injectable Chemically Stable Aqueous Omeprazole Formulation Using Nanosuspension Technology" Eur. J. Pharmaceutics and Biopharmaceutics, 58 (3), 2004, pp. 615-619.
Oltersdorf et al., "An inhibitor of Bcl-2 family proteins induces regression of solid tumours," Nature, 2005, vol. 435 (2), pp. 677-681.
Park et al., "Discovery of an Orally Bioavailable Small Molecule Inhibitor of Prosurvival B-Cell Lymphoma 2 Proteins," Journal of Medicinal Chemistry, 2008, vol. 51 (21 ), pp. 6902-6915.
Puck et al., "Immune Disorders Caused by Defects in the Caspase Cascade," Current Allergy and Asthma Reports, 2003, vol. 3, pp. 378-384.
Ramos et al., "Modulation of Autoantibody Production by Mycophenolate Mofetil: Effects on the Development of SLE in (NZB x NZW)$F_1$ Mice," Nephrology Dialysis Transplantation, 2003, vol. 18 (5), pp. 878-883.
Rengan et al., "Actin Cytoskeletal Function is Spared, but Apoptosis is Increased, in WAS Patient Hematopoietic Cells," Blood, 2000, vol. 95 (4), pp. 1283-1292.
Roberti et al., "Synthesis and Biological Evaluation of Resveratrol and Analogues as Apoptosis-Inducing Agents," J. Med. Chem. 2003, 46, 3546-3554.
Sharma et al., "Solubility Enhancement Strategies for Poorly Water-Soluble Drugs in Solid Dispersions: A Review," Asian Journal of Pharmaceutics, 2007, vol. 1 (1), pp. 9-19.
Shimazaki et al., "Evaluation of Apoptosis as a Prognostic Factor in Myelodysplastic Syndromes," British Journal of Haematology, 2000, vol. 110 (3), pp. 584-590.
Skoug et al., Enabling Discovery Through Formulation, American Association of Pharmaceutical Scientists (AAPS), Webinar [online], Presented Mar. 18, 2010, 51 pgs.
Souers et al., "ABT-199, a potent and selective BCL-2 inhibitor, achieves antitumor activity while sparing platelets," Nature Medicine, 2013, pp. 1-9.
Sperling, L. H., "Introduction to Physical Polymer Science," Second Edition, John Wiley & Sons, Inc., 1992, Table of Contents, 18 pgs.
Sutton et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Testa et al., "Predicting drug metabolism: Concepts and challenges", Pure Appl. Chem., 2004, vol. 76, No. 5, pp. 907-914.
Thomson, J.F., "Physiological Effects of $D_2O$ in Mammals," Annals New York Academy of Sciences, 1960, vol. 84, pp. 736-744.
Tse et al., "ABT-263: A Potent and Orally Bioavailable Bcl-2 Family Inhibitor," Cancer Research, 2008, vol. 68 (9), pp. 3421-3428—Including Supplementary Data.
U.S. Department of Health and Human Services Food and Drug Administration Center for Drug Evaluation and Research, Guidance for Industry, Aug. 2000, [retrieved on Jan. 25, 2012]. Retrieved from the internet <URL: http://www. f<la.gov I downloads/Drugs/ GuidanceComplianceRegulatoryInformation/Guidances/ ucm070246. pdf.>, 16 pgs.
Vandenberg et al., "ABT-199, a new Bcl-2-specific BH3 mimetic, has in vivo efficacy against aggressive Myc-driven mouse lympho-

(56) References Cited

OTHER PUBLICATIONS mas without provoking thrombocytopenia," Blood First Edition Paper, Prepublished online Jan. 22, 2013; DOI 10.1182/blood-2013-01-475855, 12 pages.
Vasanthavada et al., "Development of Solid Dispersion of Poorly Water-Soluble Drugs," Water-Insoluble Drug Formulation, 2nd Edition, 2008, pp. 499-529.
Wang, Z.X., "An Exact Mathematical Expression for Describing Competitive Binding of Two Different Ligands to a Protein Molecule," FEBS Letters, 1995, vol. 360 (2), pp. 111-114.
Wendt, M.D., "Discovery of ABT-263, a Bcl-Family Protein Inhibitor: Observations on Targeting a Large Protein-Protein Interaction," Expert Opinion on Drug Discovery, 2008, vol. 3 (9), pp. 1123-1143.
Wilson et al., "Autoimmune Disease Complicating Antiviral Therapy for Hepatitis C Virus Infection," Seminars in Arthritis and Rheumatism, 2002, vol. 32 (3), pp. 163-173.
Xie et al., "Apoptosis and Fas/bcl-2 Expression in Peripheral Blood Lymphocytes of Patients with Systemic Lupus Erythematosus," Chinese Medical Journal, 1999, vol. 113, p. 1072.
Zhang et al., "Effect of Interferon-Alpha in Systemic Lupus Erthematosus (SLE) Serum on the Differentiation and Maturation of Dendritic Cells derived from CD34+Hematopoietic Precursor Cells," Journal of Nanjing Medical University, 2009, vol. 23 (6), pp. 380-385.
Zhang et al., "Bcl-2 Family Proteins are Essential for Platelet Survival," Cell Death and Differentiation, 2007, vol. 14 (5), pp. 943-951.
International Search Report and Written Opinion of the International Searching Authority regarding PCT/US2014/017751 dated Jun. 10, 2014, 10 pgs.

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic

<400> SEQUENCE: 1

Gly Gln Val Gly Arg Gln Leu Ala Ile Ile Gly Asp Lys
1               5                   10
```

APOPTOSIS-INDUCING AGENTS FOR THE TREATMENT OF CANCER AND IMMUNE AND AUTOIMMUNE DISEASES

CROSS-REFERENCE TO RELATED APPLICATION

This application is a continuation application of U.S. application Ser. No. 14/789,449, file Jul. 1, 2015, which is incorporated by reference in its entirety. U.S. application Ser. No. 14/789,449 is a divisional application of U.S. application Ser. No. 14/176,506, filed Feb. 10, 2014, which is incorporated by reference in its entirety. U.S. application Ser. No. 14/176,506 claims priority to U.S. Provisional Application Ser. No. 61/781,070, filed Mar. 14, 2013, which is incorporated by reference in its entirety.

INCORPORATION OF SEQUENCE LISTING

A paper copy of the Sequence Listing and a computer readable form of the sequence containing the file named "ABV11872USC1_ST25.txt", which is 775 bytes in size (as measured in MICROSOFT WINDOWS® EXPLORER), are provided herein and are herein incorporated by reference. This Sequence Listing consists of SEQ ID NO: 1.

FIELD OF THE INVENTION

This invention pertains to compounds that inhibit the activity of Bcl-2 anti-apoptotic proteins, compositions containing the compounds, and methods of treating diseases using the compounds.

BACKGROUND OF THE INVENTION

The Bcl-2 family of proteins are key regulators of mitochondria-dependent apoptosis in nucleated cells and includes both anti-apoptotic (Bcl-$x_L$, Bcl-2, Bcl-w, A1, Mcl-1) and proapoptotic (Bak, Bax, Bid, Bim, Bad, Bik, Bmf, Noxa, Puma) members. Generally, the expression of Bcl-2 protein is associated with many physiologic functions, including the inhibition of apoptosis in the body, in some cases resulting in proliferation of cells affected by the Bcl-2 inhibition. As such, inhibition of Bcl-2 protein may reduce cell proliferation, leading to improved outcomes related to the treatment and prevention of cancer.

Anti-apoptotic Bcl-2 proteins are associated with a number of diseases. Bcl-2 proteins may be involved bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like. Additionally, Bcl-2 may be involved in immune and auto-immune diseases, as well as arthritis. Overexpression of Bcl-2 proteins correlates with resistance to chemotherapy, clinical outcome, disease progression, overall prognosis or a combination thereof in various cancers and disorders of the immune system.

There is a continuing need in the therapeutic arts for compounds that inhibit the activity of anti-apoptotic Bcl-2 proteins.

SUMMARY OF THE INVENTION

One embodiment of this invention pertains to compounds and therapeutically acceptable salts, prodrugs, metabolites, or salts of prodrugs thereof, which are useful as inhibitors of anti-apoptotic Bcl-2 proteins. The compounds include:

4-(4-{[2-(4-chlorophenyl)-4,4-dimethylcyclohex-1-en-1-yl]methyl}piperazin-1-yl)-N-[(4-{[(2R)-1,4-dioxan-2-ylmethyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1 S)-1-(tetrahydro-2H-pyran-4-yl)ethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1R)-1-(tetrahydro-2H-pyran-4-yl)ethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(5S,8S)-1-oxaspiro[4.5]dec-8-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(5R,8R)-1-oxaspiro[4.5]dec-8-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-hydroxytetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,4-dioxaspiro[4.5]dec-8-ylmethyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(morpholin-4-yl)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(2S)-1,4-dioxan-2-ylmethyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[3-(hydroxymethyl)oxetan-3-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxy-3-methylbutyl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(3-hydroxytricyclo[3.3.1.1$^{3,7}$]dec-1-yl)amino]-3-nitrophenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1R,5S,6S)-3-oxabicyclo[3.1.0]hex-6-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3-hydroxyoxetan-3-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}-2-(1H-pyrrolo[2,3-b]pyridin-5-yloxy)benzamide;

methyl 4-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}tetrahydro-2H-pyran-4-carboxylate;

4-(4-{[2-(4-chlorophenyl)-4,4-dimethylcyclohex-1-en-1-yl]methyl}piperazin-1-yl)-N-({3-nitro-4-[2-(tetrahydro-2H-pyran-4-yl)hydrazinyl]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4R)-oxepan-4-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(4S)-oxepan-4-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methyltetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-thiopyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[(oxetan-3-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R,5R)-5-methyl-1,4-dioxan-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(6-hydroxy-1,4-dioxepan-6-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4,4-difluoro-1-hydroxycyclohexyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-methoxytetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3,3-difluorocyclobutyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({3-nitro-4-[({1-[(trifluoromethyl)sulfonyl]piperidin-4-yl}methyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[1-(methylsulfonyl)piperidin-4-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2R,4R,6S)-2,6-dimethyltetrahydro-2H-pyran-4-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(1-oxidotetrahydro-2H-thiopyran-4-yl)methyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(4S)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(4R)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S,6R)-6-methyl-1,4-dioxan-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(3-nitro-4-{[(3 S)-tetrahydrofuran-3-ylmethyl]amino}phenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S)-6,6-dimethyl-1,4-dioxan-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(3-methyloxetan-3-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(6-fluoro-1,4-dioxepan-6-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(6-methoxy-1,4-dioxepan-6-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(trans-3-cyanocyclobutyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(cis-3-cyanocyclobutyl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S,5R)-5-methyl-1,4-dioxan-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-{[4-({[(2S,5S)-5-methyl-1,4-dioxan-2-yl]methyl}amino)-3-nitrophenyl]sulfonyl}-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-cyanotetrahydro-2H-pyran-4-yl)methyl]amino}-3-nitrophenyl)sulfonyl]-2-(1H-pyrrolo[2,3-b]pyridin-5-yloxy)benzamide;

N-[(4-{[(1-acetylpiperidin-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide;

4-(4-{[2-(4-chloro-2-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chloro-3-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-[(4-{[(4-ethyltetrahydro-2H-pyran-4-yl)methyl]amino}-3-nitrophenyl)sulfonyl]-2-(1H-pyrrolo[2,3-b]pyridin-5-yloxy)benzamide;

4-(4-{[2-(4-chlorophenyl)-4,4-dimethylcyclohex-1-en-1-yl]methyl}piperazin-1-yl)-N-({4-[(1,4-dioxepan-6-ylmethyl)amino]-3-nitrophenyl}sulfonyl)-2-(1H-pyrrolo[2,3-b]pyridin-5-yloxy)benzamide;

4-(4-{[2-(4-cyclopropylphenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide;

4-(4-{[2-(3,4-dichlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide; and 4-[4-({2-[4-(difluoromethyl)phenyl]-4,4-dimethylcyclohex-1-en-1-yl}methyl)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of this invention.

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a subject in need of treatment, said method comprising administering to the subject a therapeutically effective amount of a compound of this invention.

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a subject in need of treatment, said method comprising administering to the subject therapeutically effective amount of the compound of this invention and a therapeutically effective amount of one additional therapeutic agent or more than one additional therapeutic agent.

Another embodiment pertains to a composition for treating systemic lupus erythematosus, lupus nephritis, or Sjogren's Syndrome, said composition comprising an excipient and a therapeutically effective amount of a compound of this invention.

Another embodiment pertains to a method of treating systemic lupus erythematosus, lupus nephritis, or Sjogren's Syndrome in a subject in need of treatment, said method comprising administering to the subject a therapeutically effective amount of a compound of this invention.

Another embodiment pertains to a method of treating systemic lupus erythematosus, lupus nephritis, or Sjogren's Syndrome in a subject in need of treatment, said method comprising administering to the subject therapeutically effective amount of the compound of this invention and a therapeutically effective amount of one additional therapeutic agent or more than one additional therapeutic agent.

DETAILED DESCRIPTION OF THE INVENTION

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a Bcl-2 protein.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The term "subject" is defined herein to include animals such as mammals, including, but not limited to, primates (e.g., humans), cows, sheep, goats, horses, dogs, cats, rabbits, rats, mice and the like. In suitable embodiments, the subject is a human.

Compounds

One embodiment of this invention pertains to compounds and therapeutically acceptable salts, prodrugs, metabolites, or salts of prodrugs thereof, which are useful as inhibitors of anti-apoptotic Bcl-2 proteins.

One embodiment pertains to 4-(4-{[2-(4-chlorophenyl)-4,4-dimethylcyclohex-1-en-1-yl]methyl}piperazin-1-yl)-N-[(4-{[(2R)-1,4-dioxan-2-ylmethyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(1 S)-1-(tetrahydro-2H-pyran-4-yl)ethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(1R)-1-(tetrahydro-2H-pyran-4-yl)ethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(5S,8S)-1-oxaspiro[4.5]dec-8-ylmethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(5R,8R)-1-oxaspiro[4.5]dec-8-ylmethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(4-hydroxytetrahydro-2H-pyran-4-yl)methyl]amino}-3-nitrophenyl)sulfonyl]-2-(H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({4-[(1,4-dioxaspiro[4.5]dec-8-ylmethyl)amino]-3-nitrophenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-(morpholin-4-yl)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(2S)-1,4-dioxan-2-ylmethyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[3-(hydroxymethyl)oxetan-3-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({4-[(3-hydroxy-3-methylbutyl)amino]-3-nitrophenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({4-[(3-hydroxytricyclo[3.3.1.1$^{3,7}$]dec-1-yl)amino]-3-nitrophenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(1R,5S,6S)-3-oxabicyclo[3.1.0]hex-6-ylmethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(3-hydroxyoxetan-3-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to methyl 4-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}tetrahydro-2H-pyran-4-carboxylate; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({3-nitro-4-[2-(tetrahydro-2H-pyran-4-yl)hydrazinyl]phenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(4R)-oxepan-4-ylmethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(4S)-oxepan-4-ylmethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1- yl)-N-[(4-{[(4-methyltetrahydro-2H-pyran-4-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({3-nitro-4-[(tetrahydro-2H-thiopyran-4-ylmethyl)amino]phenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({3-nitro-4-[(oxetan-3-ylmethyl)amino]phenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(2R,5R)-5-methyl-1,4-dioxan-2-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(6-hydroxy-1,4-dioxepan-6-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(4,4-difluoro-1-hydroxycyclohexyl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(4-methoxytetrahydro-2H-pyran-4-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(3,3-difluorocyclobutyl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({3-nitro-4-[({1-[(trifluoromethyl)sulfonyl]piperidin-4-yl}methyl)amino]phenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[1-(methylsulfonyl)piperidin-4-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(2R,4R,6S)-2,6-dimethyltetrahydro-2H-pyran-4-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(1-oxidotetrahydro-2H-thiopyran-4-yl)methyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(4S)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(4R)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(2S,6R)-6-methyl-1,4-dioxan-2-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(3-nitro-4-{[(3 S)-tetrahydrofuran-3-ylmethyl]amino}phenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(2S)-6,6-dimethyl-1,4-dioxan-2-yl]methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(3-methyloxetan-3-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(6-fluoro-1,4-dioxepan-6-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(6-methoxy-1,4-dioxepan-6-yl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(trans-3-cyanocyclobutyl)methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(cis-3-cyanocyclobutyl)methyl]amino}-3-nitrophenyl)sulfonyl]-2-(1H-pyrrolo[2,3-b]pyridin-5-yloxy) benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl) methyl]amino}-3-nitrophenyl)sulfonyl]-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(2S,5R)-5-methyl-1,4-dioxan-2-yl] methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-{[4-({[(2S,5S)-5-methyl-1,4-dioxan-2-yl] methyl}amino)-3-nitrophenyl]sulfonyl}-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(4-cyanotetrahydro-2H-pyran-4-yl)methyl] amino}-3-nitrophenyl)sulfonyl]-2-(1H-pyrrolo[2,3-b] pyridin-5-yloxy)benzamide; and therapeutically acceptable salts, prodrugs, metabolites, or salts of prodrugs thereof.

Another embodiment pertains to N-[(4-{[(1-acetylpiperidin-4-yl)methyl]amino}-3-nitrophenyl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-chloro-2-fluorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin-5-yloxy)benzamide; and therapeutically acceptable salts, prodrugs, metabolites, or salts of prodrugs thereof.

Another embodiment pertains to 4-(4-{[2-(4-chloro-3-fluorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-[(4-{[(4-ethyltetrahydro-2H-pyran-4-yl)methyl] amino}-3-nitrophenyl)sulfonyl]-2-(1H-pyrrolo[2,3-b] pyridin-5-yloxy)benzamide; and therapeutically acceptable salts, prodrugs, metabolites, or salts of prodrugs thereof.

Another embodiment pertains to 4-(4-{[2-(4-chlorophenyl)-4,4-dimethylcyclohex-1-en-1-yl]methyl}piperazin-1-yl)-N-({4-[(1,4-dioxepan-6-ylmethyl)amino]-3-nitrophenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-(4-{[2-(4-cyclopropylphenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl)-2-(1H-pyrrolo [2,3-b]pyridin-5-yloxy)benzamide; and therapeutically acceptable salts, prodrugs, metabolites, or salts of prodrugs thereof.

Another embodiment pertains to 4-(4-{[2-(3,4-dichlorophenyl)-4,4-dimethylcyclohex-1-en-1-yl]methyl}piperazin-1-yl)-N-({3-nitro-4-[(tetrahydro-2H-pyran-4-ylmethyl) amino]phenyl}sulfonyl)-2-(1H-pyrrolo[2,3-b]pyridin-5-yloxy)benzamide; and therapeutically acceptable salts, prodrugs, metabolites, or salts of prodrugs thereof.

Another embodiment pertains to 4-[4-({2-[4-(difluoromethyl)phenyl]-4,4-dimethylcyclohex-1-en-1-yl}methyl)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide; and therapeutically acceptable salts, prodrugs, metabolites, or salts of prodrugs thereof.

The compounds of the invention may comprise geometric isomers. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of the invention can exist in a prodrug form of the selective Bcl-2 inhibitor compound. Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property. Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "*Essentials of Medicinal Chemistry*", John Wiley-Interscience Publications, John Wiley and Sons, New York (1988), pp. 97-118, which is incorporated in its entirety by reference herein.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the subject or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.,* 36(10):927-932 (1995); Kushner et al., *Can. J. Physiol. Pharmacol.,* 77, 79-88 (1999).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Pharmaceutical Compositions, Combination Therapies, and Administration

Another embodiment pertains to pharmaceutical compositions comprising a compound of this invention and an excipient.

Still another embodiment pertains to compositions for treating diseases during which anti-apoptotic Bcl-2 proteins are expressed, said compositions comprising an excipient and a therapeutically effective amount of the compound of this invention.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound of this invention.

Still another embodiment pertains to compositions for treating diseases during which are expressed anti-apoptotic Bcl-2 proteins, said compositions comprising an excipient and a therapeutically effective amount of the compound of this invention and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound of this invention and a therapeutically effective amount of one additional therapeutic agent or more than one additional therapeutic agent.

Still another embodiment pertains to compositions for treating systemic lupus erythematosus, lupus nephritis, or Sjogren's Syndrome, said compositions comprising an excipient and a therapeutically effective amount of the compound of this invention.

Still another embodiment pertains to compositions for treating systemic lupus erythematosus, lupus nephritis, or Sjogren's Syndrome, said compositions comprising an excipient and a therapeutically effective amount of the compound of this invention and a therapeutically effective amount of one additional therapeutic agent or more than one additional therapeutic agent.

Metabolites of compounds of this invention, produced by in vitro or in vivo metabolic processes, may also have utility for treating diseases associated with anti-apoptotic Bcl-2 proteins.

Certain precursor compounds which may be metabolized in vitro or in vivo to form compounds of this invention may also have utility for treating diseases associated with expression of anti-apoptotic Bcl-2 proteins.

Compounds of this invention may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds of this invention may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds of this invention depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention used to make a composition to be administered daily to a subject in a single dose or in divided doses is from about 0.001 to about 1000 mg/kg, or about 0.01 to about 500 mg/kg, or about 0.1 to about 300 mg/kg. Single dose compositions contain these amounts or a combination of submultiples thereof.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Compounds of this invention may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The excipients may be pharmaceutically acceptable excipients.

Excipients for preparation of compositions comprising a compound of this invention to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention to be administered osmotically include, for example, chlorofluorohydrocarbons, ethanol, water and mixtures thereof. Excipients for preparation of compositions comprising a compound of this invention to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention to be administered rectally or vaginally include, for example, cocoa butter, polyethylene glycol, wax and mixtures thereof.

Compounds of this invention are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-$OCH_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo

[2,3-b]pyridin-5-yloxy)benzamide (ABT-199), GX-070 (obatoclax) and the like. Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709, dinaciclib and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS 1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75, trastuzumab emtansine and the like.

Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRE- TIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171, carfilzomib and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1 b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds of this invention may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor-alpha), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Many proteins have been implicated in general autoimmune and inflammatory responses. Accordingly, it may be possible to combine the selective Bcl-2 inhibitors of the invention with compounds capable of altering the function of other proteins implicated in general autoimmune and inflammatory responses. Examples of proteins associated with autoimmune and inflammatory response include C5, CCL1 (1-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, ABCF1, BCL6, C3, C4A, CEBPB, CRP, ICEBERG, IL1R1, IL1RN, IL8RB, LTB4R, TOLLIP, FADD, IRAK-M, IRAK1, IRAK2, IRAK4, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL11RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, RNF110 (ZNF144), FGF family, PLGF, DLL4, NPR-1, Fc gamma receptor IIB modulators, anti-plasmacytoid cells modulators, Immune-complex clearance modifiers such as RNase or DNase, proto oncogen inhibitors such as, but not limited to c-kit and b-raf, Type 1 fibroblasts growth factor receptor modulators, dihydroorotate dehydrogenase modulators, estrogen receptor modulators, DNA directed DNA polymerase inhibitor, CD85gamma modulators, and epigenetic modifiers.

Combinations for treating autoimmune and inflammatory diseases may include compounds of the invention and non-steroidal anti-inflammatory drug(s), also referred to as NSAIDS, which include drugs like ibuprofen. Other combinations may include corticosteroids including prednisolone; the well known side-effects of steroid use can be reduced or even eliminated by tapering the steroid dose required when treating subjects in combination with this invention.

Non-limiting examples of therapeutic agents that may be used in combination with selective Bcl-2 inhibitors of this invention for treating lupus include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-9, IL-10, IL-11, IL-12, IL-13, IL-15, IL-16, IL-17A, IL-17F, IL-18, IL-21, IL-22, IL-23, IL-25, IL-33, interferons (for example, alpha, beta, gamma etc), Tweak, BAFF/BLyS, April, chemokines. Compounds of the invention can also be combined with antibodies to cell surface molecules such as CD2, CD3, CD4, CD8, CD16, CD19, CD20, CD22, CD25, CD28, CD30, CD32, CD40, CD45, CD47, CD52, CD54, CD64, CD69, CD72, CD79, CD80 (B7.1), CD86 (B7.2), CD90, CD100, CD200, CTLA, ICOS-1, B7RP, BR3, TACI, BCMA, or their ligands including CD154 (gp39 or CD40L).

Compounds of the invention may also be combined with other agents, such as cytoxan, 6-MP, azathioprine sulphasalazine, mesalazine, olsalazine chloroquinine, penicillamine, aurothiomalate (intramuscular and oral), azathioprine, cochicine, corticosteroids (oral, inhaled and local injection), selective glucocorticoid receptor modulators (SGRMs), O beta-2 adrenoreceptor agonists (salbutamol, terbutaline, salmeterol), xanthines (theophylline, aminophylline), cromoglycate, nedocromil, ketotifen, ipratropium and oxitropium, cyclosporin, FK506, leflunomide, corticosteroids such as prednisolone, phosphodiesterase inhibitors, adensosine agonists, antithrombotic agents, complement inhibitors, adrenergic agents, agents which interfere with signaling by proinflammatory cytokines such as TNF-α or IL-1 (e.g., IRAK, NIK, IKK, p38 or MAP kinase inhibitors), IL-1β converting enzyme inhibitors, JAK inhibitors, BTK inhibitors, SYK inhibitors, PKC family inhibitors, TNF-α converting enzyme (TACE) inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g., IL-4, IL-6, IL-10, IL-11, IL12, IL-13, IL-17, IL-18, IL-33 and TGFβ), folic acid, hydroxychloroquine sulfate, etanercept, infliximab, methylprednisolone, meloxicam, methylprednisolone acetate, gold sodium thiomalate, aspirin, triamcinolone acetonide, propoxyphene napsylate/apap, folate, diclofenac sodium, oxycodone HCl, hydrocodone bitartrate/apap, diclofenac sodium/misoprostol, fentanyl, anakinra, human recombinant, tramadol HCl, cyanocobalamin/fa/pyridoxine, acetaminophen, alendronate sodium, prednisolone, morphine sulfate, lidocaine hydrochloride, glucosamine sulf/chondroitin, amitriptyline HCl, sulfadiazine, olopatadine HCl, misoprostol, omeprazole, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, Mesopram. Combinations may additionally include leflunomide, cyclosporine and S1P agonists.

Examples of therapeutic agents for SLE (Lupus) and lupus nephritis, with which the compounds of the invention can be combined include the following: NSAIDs, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. binding proteins incorporated into the methods of the invention, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. The invention may also be used with T cell signaling inhibitors, for example, tyrosine kinase inhibitors; or molecules that target T cell activation molecules, for example, CTLA-4-IgG or anti-B7 family antibodies such as B7RP, anti-PD-1 family antibodies. The invention, can be combined with IL-11 or anti-cytokine antibodies, for example, fonotolizumab (anti-IFNg antibody), anti-interferon alpha, or anti-receptor receptor antibodies, for example, anti-IL-6 receptor antibody (including gp130) and antibodies to B-cell surface molecules. The invention may also be used with inhibitors of HMGB1, HDGF. The invention may also be used with inhibitors of toll receptors 1, 2, 3, 4, 7, and 9. The invention may also be used with inhibitors of dendritic cell makers BDCA-1, 2 and 3, DEC205, CD11c, Bst2 (PDCA-1), Langerin, and SiglecH. The invention may also be used with agents which promote regulatory T cell function. The invention may also be used with LJP 394 (abetimus), agents that inhibit complement, for example, anti-C5, anti-C5a, deplete or inactivate B-cells, for example, Rituximab (anti-CD20 antibody), lymphostat-B (anti-BlyS antibody), anti-CD22, TNF antagonists, for example, anti-TNF antibodies, Adalimumab (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) and inhibitors of other bcl-2 family members such as Bcl-$x_L$, Mcl-1, A-1 etc.

Examples of therapeutic agents used to treat Sjogren's Syndrome, that may be combined with the selective Bcl-2 inhibitors of the invention include, but are not limited to artificial tears, cyclosporine, cevimeline, pilocarpine, NSAIDs, corticosteroids, immunosuppressants, disease-modifying anti-rheumatic drugs (DMARDs) such as methotrexate, and hydroxychloroquine.

Methods of Treatment

An embodiment of the invention pertains to methods of treating cancer in a mammal comprising administering thereto a therapeutically acceptable amount of a compound of this invention.

Still another embodiment pertains to methods of treating autoimmune disease in a mammal comprising administering thereto a therapeutically acceptable amount of a compound of this invention.

Still another embodiment pertains to methods of treating disease in a subject during which anti-apoptotic Bcl-2 proteins are expressed, said methods comprising administering to the subject a therapeutically effective amount of a compound of this invention.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a subject, said methods comprising administering to the subject a therapeutically effective amount of a compound of this invention.

Still another embodiment pertains to methods of treating disease in a subject during which are expressed anti-apoptotic Bcl-2 proteins, said methods comprising administering to the subject a therapeutically effective amount of a compound of this invention and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a subject, said methods comprising administering to the subject a therapeutically effective amount of the compound of this invention and a therapeutically effective amount of one additional therapeutic agent or more than one additional therapeutic agent.

Still another embodiment pertains to methods of treating systemic lupus erythematosus, lupus nephritis, or Sjogren's Syndrome in a subject, said methods comprising administering to the subject a therapeutically effective amount of a compound of this invention.

Still another embodiment pertains to methods of treating systemic lupus erythematosus, lupus nephritis, and Sjogren's Syndrome in a subject, said methods comprising administering to the subject a therapeutically effective amount of the compound of this invention and a therapeutically effective amount of one additional therapeutic agent or more than one additional therapeutic agent.

It is expected that, because compounds of this invention bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT/US2004/036770, published as WO 2005/049593, in PCT/US2004/037911, published as WO 2005/049594, and in PCT/US01/29432, published as WO02/24636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418. Involvement of Bcl-2 proteins in arthritis is disclosed in commonly-owned PCT/US2008/083478, published as WO 2009/064938. Involvement of Bcl-2 proteins in methods of treating systemic lupus erythematosus, lupus nephritis, and Sjogren's Syndrome is described in commonly-owned PCT/US2011/061769, published as WO 2012/071374. Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds of this invention would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-l-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, *chlamydia*, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, irritable bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, *legionella*, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium* intracellulare, *mycobacterium tuberculosis*, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherosclerotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthopathy, sporadic, polyglandular deficiency type I, sporadic polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

EXAMPLES

Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC-HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

Compounds of this invention may be made by synthetic chemical processes, examples of which are shown herein. Exemplary schemes of the most useful and readily understood description of procedures and conceptual aspects of this invention are disclosed in commonly-owned U.S. patent application Ser. No. 12/951,344. It is meant to be understood that the order of the steps in the processes may be varied, that reagents, solvents and reaction conditions may be substituted for those specifically mentioned, and that vulnerable moieties may be protected and deprotected, as necessary.

It will be readily apparent to those skilled in the art that other suitable modifications and adaptations of the compounds of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

The following examples are presented to provide what is believed to be the most useful and readily understood description of procedures and conceptual aspects of this invention. Each exemplified compound and intermediate was named using ACD/ChemSketch Build 59026 (3 Sep. 2012), Advanced Chemistry Development Inc., Toronto, Ontario), or ChemDraw® Ver. 9.0.7 (CambridgeSoft, Cambridge, Mass.).

Example 1

4-(4-{[2-(4-chlorophenyl)-4,4-dimethylcyclohex-1-en-1-yl]methyl}piperazin-1-yl)-N-[(4-{[(2R)-1,4-dioxan-2-ylmethyl]amino}-3-nitrophenyl)sulfonyl]-2-(1H-pyrrolo[2,3-b]pyridin-5-yloxy)benzamide

Example 1A methyl 4,4-dimethyl-2-(trifluoromethylsulfonyloxy)cyclohex-1-enecarboxylate To a suspension of hexane washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and triflic anhydride (40 mL) was added. The reaction mixture was warmed to room temperature and stirred for 24 hours. The organic layer was washed with brine, dried ($Na_2SO_4$), filtered, and concentrated to afford the title compound.

Example 1B methyl 2-(4-chlorophenyl)-4,4-dimethylcyclohex-1-enecarboxylate

EXAMPLE 1A (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether (4×200 mL) was added and the mixture was filtered. The combined ether solution was concentrated to afford the title compound.

Example 1C (2-(4-chlorophenyl)-4,4-dimethylcyclohex-1-enyl)methanol

To a mixture of $LiBH_4$ (13 g), EXAMPLE 1B (53.8 g) and ether (400 mL), was added methanol (25 mL) slowly by syringe. The mixture was stirred at room temperature for 24 hours. The reaction was quenched with 1N aqueous HCl with ice-cooling. The mixture was diluted with water and extracted with ether (3×100 mL). The extracts were dried ($Na_2SO_4$), filtered, and concentrated. The crude product was chromatographed on silica gel with 0-30% ethyl acetate/hexanes.

Example 1D tert-butyl 4-((2-(4-chlorophenyl)-4,4-dimethylcyclohex-1-enyl)methyl)piperazine-1-carboxylate Mesyl Chloride (7.5 mL) was added via syringe to EXAMPLE 1C (29.3 g) and triethylamine (30 mL) in $CH_2Cl_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Example 1E 1-((2-(4-chlorophenyl)-4,4-dimethylcyclohex-1-enyl)methyl)piperazine EXAMPLE 1D (1 g) was stirred in dichloromethane (10 mL), trifluoroacetic acid (10 mL), and triethylsilane (1 mL) for 1 hour. The mixture was concentrated, taken up in a mixture of dichloromethane (100 mL) and saturated aqueous $Na_2CO_3$ solution (20 mL) and stirred for 10 minutes. The layers were separated, and the organic layer was dried over $Na_2SO_4$, filtered, and concentrated to afford the title compound.

Example 1F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 mL) was added 1M lithium hexamethyldisilazide in tetrahydrofuran (86 mL), and after 10 minutes, TIPS-Cl (triisopropylchlorosilane) (18.2 mL) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Example 1G 1-(triisopropylsilyl)-1H-pyrrolo[2,3-b]pyridin-5-ol

To a mixture of EXAMPLE 1F (24.3 g) in tetrahydrofuran (500 mL) at −78° C. was added 2.5M BuLi in hexanes (30.3 mL). After 2 minutes, trimethylborate (11.5 mL) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 mL) at 0° C., and 1M aqueous NaOH (69 mL) was added, followed by 30% aqueous $H_2O_2$ (8.43 mL), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Example 1H methyl 2-(1H-pyrrolo[2,3-b]pyridin-5-yloxy)-4-fluorobenzoate

A mixture of EXAMPLE 1G (8.5 g), methyl 2,4-difluorobenzoate (7.05 g), and $K_3PO_4$ (9.32 g) in diglyme (40 mL) at 115° C. was stirred for 24 hours. The reaction was cooled, diluted with ether (600 mL), and washed twice with water, and brine, and concentrated. The crude product was chromatographed on silica gel with 2-50% ethyl acetate/hexanes.

Example 1I methyl 2-(1H-pyrrolo[2,3-b]pyridin-5-yloxy)-4-(4-((2-(4-chlorophenyl)-4,4-dimethylcyclohex-1-enyl) methyl)piperazin-1-yl)benzoate A mixture of EXAMPLE 1H (1.55 g), EXAMPLE 1E (2.42 g), and $HK_2PO_4$ (1.42 g) in dimethylsulfoxide (20 mL) at 135° C. was stirred for 24 hours. The reaction was cooled, diluted with ether (400 mL), and washed three times with 1M aqueous NaOH, and brine, and concentrated. The crude product was chromatographed on silica gel with 10-50% ethyl acetate/hexanes.

Example 1J 2-(1H-pyrrolo[2,3-b]pyridin-5-yloxy)-4-(4-((2-(4-chlorophenyl)-4,4-dimethylcyclohex-1-enyl)methyl) piperazin-1-yl)benzoic acid EXAMPLE 1I (200 mg) in dioxane (10 mL) and 1M aqueous NaOH (6 mL) at 50° C. was stirred for 24 hours. The reaction was cooled, added to $NaH_2PO_4$ solution, and extracted three times with ethyl acetate. The combined extracts were washed with brine, and concentrated to afford the title compound.

Example 1K (S)-(1,4-dioxan-2-yl)methyl 4-methylbenzenesulfonate

To 2-chloroethanol (9.1 mL) in toluene (17 mL) was added $Et_2O.BF_3$ (0.30 mL), and a warm water bath was used to warm the mixture to 38° C. S-(+)-epichlorohydrin (3.4 mL) was added dropwise, keeping the temperature <45° C. The reaction was stirred at ~35° C. for 20 minutes, cooled to 15° C., and 20% NaOH (21 mL) was added dropwise, keeping the temperature <18° C. The reaction was then allowed to warm to room temperature for 1 hour. Water was added (10 mL), the layers were separated, the aqueous layer was extracted with toluene, the combined toluene layers washed with water, and the organic layer was concentrated down to an oil. NaOH (20% (wt) aqueous, 50 g) was heated to 90° C., then the above oil was added, and the mixture was heated for 1 hour, and cooled to room temperature. Then dichloromethane (12 mL) was added, followed by p-toluenesulfonyl chloride (8.0 g). The biphasic reaction was stirred at room temperature overnight. Water was added (10 mL), and the aqueous layer was extracted twice with dichloromethane (10 mL). The combined dichloromethane layers were washed with 1/1 water/brine and dried over $Na_2SO_4$. After filtration and concentration, the crude material was chromatographed on silica gel with 65/35 heptanes/ethyl acetate to afford the title compound.

Example 1L (R)-2-(azidomethyl)-1,4-dioxane

EXAMPLE 1K (2.5 g) was dissolved in N,N-dimethylformamide (12 mL), then sodium azide (1.0 g) was added and the reaction was heated at 80° C. for 3 hours. The reaction was then cooled and diluted with water and extracted with ethyl acetate. The organic layer was washed with brine and the combined aqueous layers were extracted with ethyl acetate. The combined organic layers were dried over $Na_2SO_4$. After filtration and concentration, the crude material was chromatographed on silica gel with 3/1 heptanes/ethyl acetate to afford the title compound.

Example 1M (R)-(1,4-dioxan-2-yl)methanamine

EXAMPLE 1L (916 mg) was dissolved in tetrahydrofuran (20 mL) and water (5 mL Then trimethylphosphine (6.4 mL, 1.0M in tetrahydrofuran) was added and the reaction mixture was stirred at room temperature for 90 minutes. Then 2N aqueous LiOH (6 mL) was added, and extracted with ethyl acetate. The organic layer was washed twice with brine, then dried over $Na_2SO_4$. After filtration and concentration, the product was used in the next step without purification.

Example 1N (R)-4-((1,4-dioxan-2-yl)methylamino)-3-nitrobenzenesulfonamide

EXAMPLE 1M (160 mg) was dissolved in tetrahydrofuran (3 mL), then 4-fluoro-3-nitrobenzenesulfonamide (164 mg) was added, followed by N-ethyl-N-isopropylpropan-2-amine (0.25 mL), and the mixture was heated at 45° C. overnight. The reaction mixture was then concentrated and methanol (3 mL) was added and the mixture was stirred overnight. The solids were filtered off, and the filter cake was washed with more methanol to afford the title compound.

Example 1O 4-(4-{[2-(4-chlorophenyl)-4,4-dimethylcyclohex-1-en-1-yl]methyl}piperazin-1-yl)-N-[(4-{[(2R)-1,4-dioxan-2-ylmethyl]amino}-3-nitrophenyl)sulfonyl]-2-(1H-pyrrolo[2,3-b]pyridin-5-yloxy)benzamide EXAMPLE 1N (170 mg), EXAMPLE 1J (340 mg), 1-ethyl-3-[3-(dimethylamino)propyl]-carbodiimide hydrochloride (150 mg), and 4-dimethylaminopyridine (130 mg) were stirred in $CH_2Cl_2$ (5 mL) overnight. $N^1$,$N^1$-dimethylethane-1,2-diamine (0.19 mL) was then added and the mixture was stirred for 90 minutes. Dichloromethane (15 mL) was added, and the reaction mixture was washed with 10% acetic acid:0.75% NaCl in water (2×12 mL). The combined aqueous layers were back-extracted with dichloromethane, and the combined organics were washed with brine, and dried over $Na_2SO_4$. After filtration and concentration, the crude material was chromatographed on silica gel with 3/7 dichloromethane/ethyl acetate. The material was then chromatographed on silica gel with 1.5-2.5% $CH_3OH$ in dichloromethane. The material was triturated with $CH_3CN$ to afford the title compound. $^1$H NMR (400 MHz, dimethylsulfoxide-$d_6$) δ ppm 11.65 (s, 1H), 8.55 (t, 1H), 8.54 (d, 1H), 8.01 (d, 1H), 7.81 (dd, 1H), 7.50 (m, 3H), 7.32 (d, 2H), 7.07 (d, 1H), 7.02 (d, 2H), 6.66 (dd, 1H), 6.37 (m, 1H), 6.18 (d, 1H), 3.77 (m, 3H), 3.63 (m, 2H), 3.47 (m, 2H), 3.31 (m, 2H), 3.06 (br m, 4H), 2.74 (br s, 2H), 2.19 (br m, 4H), 2.13 (br m, 2H), 1.94 (br m, 2H), 1.37 (t, 2H), 0.90 (s, 6H).

Example 2

4-(4-{[2-(4-chlorophenyl)-4,4-dimethylcyclohex-1-en-1-yl]methyl}piperazin-1-yl)-N-[(3-nitro-4-{[(1S)-1-(tetrahydro-2H-pyran-4-yl)ethyl]amino}phenyl)sulfonyl]-2-(1H-pyrrolo[2,3-b]pyridin-5-yloxy)benzamide

Example 2A

(S)-3-nitro-4-((1-(tetrahydro-2H-pyran-4-yl)ethyl)amino)benzenesulfonamide

The title compound was prepared by substituting (S)-1-(tetrahydro-2H-pyran-4-yl)ethanamine for EXAMPLE 1M in EXAMPLE 1N.

Example 2B

4-(4-{[2-(4-chlorophenyl)-4,4-dimethylcyclohex-1-en-1-yl]methyl}piperazin-1-yl)-N-[(3-nitro-4-{[(1S)-1-(tetrahydro-2H-pyran-4-yl)ethyl]amino}phenyl)sulfonyl]-2-(1H-pyrrolo[2,3-b]pyridin-5-yloxy)benzamide The title compound was prepared by substituting EXAMPLE 2A for EXAMPLE 1N in EXAMPLE 1O. $^1$H NMR (300 MHz, dimethylsulfoxide-$d_6$) δ ppm 11.68 (s, 1H), 11.36 (bs, 1H), 8.57 (d, 1H), 8.30 (d, 1H), 8.06 (d, 1H), 7.82 (dd, 1H), 7.56 (d, 1H), 7.52-7.48 (m, 2H), 7.34 (dt, 2H), 7.16 (d, 1H), 7.03 (dt, 2H), 6.68 (dd, 1H), 6.40 (dd, 1H), 6.18 (d, 1H), 3.92-3.82 (m, 2H), 3.76 (q, 1H), 3.27 (td, 2H), 3.07 (bs, 4H), 2.75 (bs, 2H), 2.25-2.10 (m, 6H), 1.95 (bs, 2H), 1.80 (m, 1H), 1.71-1.53 (m, 2H), 1.38 (t, 2H), 1.33-1.23 (m, 2H), 1.19 (d, 3H), 0.92 (s, 6H).

Example 3

4-(4-{[2-(4-chlorophenyl)-4,4-dimethylcyclohex-1-en-1-yl]methyl}piperazin-1-yl)-N-[(3-nitro-4-{[(1R)-1-(tetrahydro-2H-pyran-4-yl)ethyl]amino}phenyl)sulfonyl]-2-(1H-pyrrolo[2,3-b]pyridin-5-yloxy)benzamide

Example 3A

(R)-3-nitro-4-((1-(tetrahydro-2H-pyran-4-yl)ethyl)amino)benzenesulfonamide

The title compound was prepared by substituting (R)-1-(tetrahydro-2H-pyran-4-yl)ethanamine for EXAMPLE 1M in EXAMPLE 1N.

Example 3B

4-(4-{[2-(4-chlorophenyl)-4,4-dimethylcyclohex-1-en-1-yl]methyl}piperazin-1-yl)-N-[(3-nitro-4-{[(1R)-1-(tetrahydro-2H-pyran-4-yl)ethyl]amino}phenyl)sulfonyl]-2-(1H-pyrrolo[2,3-b]pyridin-5-yloxy)benzamide The title compound was prepared by substituting EXAMPLE 3A for EXAMPLE 1N in EXAMPLE 1O. $^1$H NMR (300 MHz, dimethylsulfoxide-$d_6$) δ ppm 11.68 (s, 1H), 11.36 (bs, 1H), 8.57 (d, 1H), 8.30 (d, 1H), 8.06 (d, 1H), 7.82 (dd, 1H), 7.56 (d, 1H), 7.52-7.48 (m, 2H), 7.34 (dt, 2H), 7.16 (d, 1H), 7.03 (dt, 2H), 6.68 (dd, 1H), 6.40 (dd, 1H), 6.18 (d, 1H), 3.92-3.82 (m, 2H), 3.76 (q, 1H), 3.27 (td, 2H), 3.07 (bs, 4H), 2.75 (bs, 2H), 2.25-2.10 (m, 6H), 1.95 (bs, 2H), 1.80 (m, 1H), 1.71-1.53 (m, 2H), 1.38 (t, 2H), 1.33-1.23 (m, 2H), 1.19 (d, 3H), 0.92 (s, 6H).

Example 4

4-(4-{[2-(4-chlorophenyl)-4,4-dimethylcyclohex-1-en-1-yl]methyl}piperazin-1-yl)-N-[(3-nitro-4-{[(5S,8S)-1-oxaspiro[4.5]dec-8-ylmethyl]amino}phenyl)sulfonyl]-2-(1H-pyrrolo[2,3-b]pyridin-5-yloxy)benzamide

Example 4A

1-oxaspiro[4.5]decane-8-carbonitrile

Potassium t-butoxide (1.68 g) was added portionwise to a mixture of 1-oxaspiro[4.5]decan-8-one (0.96 g) and TosMIC reagent (p-toluenesulfonylmethyl isocyanide, 1.46 g) in 1,2-dimethoxyethane (30 mL) and ethanol (0.5 mL) at 0° C. The reaction mixture was allowed to warm to room temperature and stirred for 4 hours, then heated to 40° C. for 24 hours. The reaction mixture was cooled, diluted with ether (600 mL), washed twice with water and brine, and concentrated. The crude product was chromatographed on silica gel with 1-20% ethyl acetate/hexanes to afford the title compound.

Example 4B

1-oxaspiro[4.5]decane-8-ylmethylamine $LiAlH_4$ (9.1 mL, 1M in tetrahydrofuran) was added to EXAMPLE 4A (0.96 g) in tetrahydrofuran (30 mL) at 0° C. The reaction mixture was allowed to warm to room temperature and stirred for 1 hour. The reaction mixture was quenched with the addition of 2 mL water and 10 mL 1M aqueous NaOH, and the mixture was stirred for 1 hour. The reaction mixture was diluted with ether (100 mL), filtered, and concentrated to afford the title compound.

Example 4C 4-(((5S,8S)-1-oxaspiro[4.5]decan-8-ylmethyl)amino)-3-nitrobenzenesulfonamide 4-Fluoro-3-nitrobenzenesulfonamide (650 mg), EXAMPLE 4B (500 mg) and triethylamine (0.41 mL) in tetrahydrofuran (12 mL) were heated at 50° C. for 2 hours. The reaction mixture was concentrated. The crude product was chromatographed on silica gel with 50% ethyl acetate/hexanes to afford the title compound.

Example 4D 4-(((5R,8R)-1-oxaspiro[4.5]decan-8-ylmethyl)amino)-3-nitrobenzenesulfonamide The title compound was also isolated from EXAMPLE 4C as the later-eluting fraction.

Example 4E

N-((4-(((5S,8S)-1-oxaspiro[4.5]decan-8-ylmethyl)amino)-3-nitrophenyl)sulfonyl)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzamide The title compound was prepared by substituting EXAMPLE 4C for EXAMPLE 1N in EXAMPLE 1O. $^1$H NMR (300 MHz, dimethylsulfoxide-$d_6$) δ 11.69 (s, 1H), 11.35 (br s, 1H), 8.59 (m, 1H), 8.56 (s, 1H), 8.04 (s, 1H), 7.79 (d, 1H), 7.51 (m, 2H), 7.34 (d, 2H), 7.07 (d, 1H), 7.04 (d, 2H), 6.67 (d, 1H), 6.38 (d, 1H), 6.19 (s, 1H), 3.68 (t, 2H), 3.26 (m, 6H), 3.07 (m, 4H), 2.74 (s, 2H), 2.19 (s, 2H), 2.14 (m, 2H), 1.97 (s, 2H), 1.82 (m, 2H), 1.60 (m, 2H), 1.57 (m, 4H), 1.36 (m, 2H), 1.32 (m, 4H), 0.92 (m, 6H).

Example 5

4-(4-{[2-(4-chlorophenyl)-4,4-dimethylcyclohex-1-en-1-yl]methyl}piperazin-1-yl)-N-[(3-nitro-4-{[(5R,8R)-1-oxaspiro[4.5]dec-8-ylmethyl]amino}phenyl)sulfonyl]-2-(1H-pyrrolo[2,3-b]pyridin-5-yloxy)benzamide The title compound was prepared by substituting EXAMPLE 4D for EXAMPLE 1N in EXAMPLE 1O. $^1$H NMR (300 MHz, dimethylsulfoxide-$d_6$) δ 11.69 (s, 1H), 11.35 (br s, 1H), 8.60 (m, 1H), 8.57 (s, 1H), 8.05 (s, 1H), 7.81 (d, 1H), 7.51 (m, 2H), 7.34 (d, 2H), 7.09 (d, 1H), 7.03 (d, 2H), 6.67 (d, 1H), 6.39 (d, 1H), 6.19 (s, 1H), 3.67 (t, 2H), 3.27 (m, 6H), 3.07 (m, 4H), 2.75 (s, 2H), 2.20 (s, 2H), 2.14 (m, 2H), 1.95 (s, 2H), 1.81 (m, 2H), 1.75 (m, 2H), 1.65 (m, 2H), 1.63 (m, 2H), 1.38 (m, 2H), 1.32 (m, 2H), 1.09 (m, 2H), 0.92 (m, 6H).

Example 6

4-(4-{[2-(4-chlorophenyl)-4,4-dimethylcyclohex-1-en-1-yl]methyl}piperazin-1-yl)-N-[(4-{[(4-hydroxytetrahydro-2H-pyran-4-yl)methyl]amino}-3-nitrophenyl)sulfonyl]-2-(1H-pyrrolo[2,3-b]pyridin-5-yloxy)benzamide Example 6A 4-(((4-hydroxytetrahydro-2H-pyran-4-yl)methyl)amino)-3-nitrobenzenesulfonamide The title compound was prepared by substituting 4-(aminomethyl)tetrahydro-2H-pyran-4-ol for EXAMPLE 1M in EXAMPLE 1N.

Example 6B 4-(4-{[2-(4-chlorophenyl)-4,4-dimethylcyclohex-1-en-1-yl]methyl}piperazin-1-yl)-N-[(4-{[(4-hydroxytetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting EXAMPLE 6A for EXAMPLE 1N in EXAMPLE 1O. $^1$H NMR (300 MHz, dimethylsulfoxide-$d_6$) δ ppm 11.67 (s, 1H), 8.66 (t, 1H), 8.56 (d, 1H), 8.04 (d, 1H), 7.80 (dd, 1H), 7.52 (d, 1H), 7.49 (d, 2H), 7.34 (d, 2H), 7.16 (d, 1H), 7.04 (d, 2H), 6.66 (dd, 1H), 6.39 (dd, 1H), 6.19 (d, 1H), 4.99 (bs, 1H), 3.63 (d, 4H), 3.38 (d, 2H), 3.07 (bs, 4H), 2.75 (bs, 2H), 2.23-2.11 (m, 6H), 1.95 (bs, 2H), 1.66-1.57 (m, 2H), 1.54-1.48 (m, 2H), 1.38 (t, 2H), 0.92 (s, 6H).

Example 7

4-(4-{[2-(4-chlorophenyl)-4,4-dimethylcyclohex-1-en-1-yl]methyl}piperazin-1-yl)-N-({4-[(1,4-dioxaspiro[4.5]dec-8-ylmethyl)amino]-3-nitrophenyl}sulfonyl)-2-(1H-pyrrolo[2,3-b]pyridin-5-yloxy)benzamide Example 7A 1,4-dioxaspiro[4.5]decane-8-carbonitrile The title compound was prepared by substituting 1,4-dioxaspiro[4.5]decan-8-one for 1-oxaspiro[4.5]decan-8-one in EXAMPLE 4A.

Example 7B 1,4-dioxaspiro[4.5]decan-8-ylmethanamine

The title compound was prepared by substituting EXAMPLE 7A for EXAMPLE 4A in EXAMPLE 4B.

Example 7C 4-((1,4-dioxaspiro[4.5]decan-8-ylmethyl)amino)-3-nitrobenzenesulfonamide The title compound was prepared by substituting EXAMPLE 7B for EXAMPLE 1M in EXAMPLE 1N.

Example 7D 4-(4-{[2-(4-chlorophenyl)-4,4-dimethylcyclohex-1-en-1-yl]methyl}piperazin-1-yl)-N-({4-[(1,4-dioxaspiro[4.5]dec-8-ylmethyl)amino]-3-nitrophenyl}sulfonyl)-2-(1H-pyrrolo[2,3-b]pyridin-5-yloxy)benzamide The title compound was prepared by substituting EXAMPLE 7C for EXAMPLE 1N in EXAMPLE 1O. $^{1}$H NMR (400 MHz, dimethylsulfoxide-$d_6$) δ ppm 11.60 (s, 1H), 8.48 (d, 2H), 7.99 (d, 1H), 7.71 (dd, 1H), 7.53 (d, 1H), 7.38-7.48 (m, 1H), 7.34 (d, 2H), 7.04 (d, 2H), 6.95 (d, 1H), 6.65 (dd, 1H), 6.35 (dd, 1H), 6.21 (d, 1H), 3.84 (s, 4H), 3.25 (t, 3H), 3.04 (s, 4H), 2.72 (s, 2H), 2.08-2.25 (m, 6H), 1.95 (s, 2H), 1.69 (t, 5H), 1.34-1.52 (m, 4H), 1.25 (d, 2H), 0.85-1.00 (m, 6H).

Example 8

4-(4-{[2-(4-chlorophenyl)-4,4-dimethylcyclohex-1-en-1-yl]methyl}piperazin-1-yl)-N-{[4-(morpholin-4-yl)-3-nitrophenyl]sulfonyl}-2-(1H-pyrrolo[2,3-b]pyridin-5-yloxy)benzamide Example 8A 4-morpholino-3-nitrobenzenesulfonamide The title compound was prepared by substituting morpholine for EXAMPLE 1M in EXAMPLE 1N.

Example 8B 4-(4-{[2-(4-chlorophenyl)-4,4-dimethylcyclohex-1-en-1-yl]methyl}piperazin-1-yl)-N-{[4-(morpholin-4-yl)-3-nitrophenyl]sulfonyl}-2-(1H-pyrrolo[2,3-b]pyridin-5-yloxy)benzamide The title compound was prepared by substituting EXAMPLE 8A for EXAMPLE 1N in EXAMPLE 1O. $^{1}$H NMR (300 MHz, dimethylsulfoxide-$d_6$) δ ppm 11.68 (s, 1H), 11.42 (bs, 1H), 8.27 (d, 1H), 8.03 (d, 1H), 7.86 (d, 1H), 7.53-7.48 (m, 3H), 7.35 (d, 2H), 7.24 (d, 1H), 7.05 (d, 2H), 6.67 (dd, 1H), 6.40 (dd, 1H), 6.20 (d, 1H), 3.69 (t, 4H), 3.16-3.02 (m, 8H), 2.76 (bs, 2H), 2.28-2.11 (m, 6H), 1.96 (bs, 2H), 1.39 (t, 2H), 0.93 (s, 6H).

Example 9

4-(4-{[2-(4-chlorophenyl)-4,4-dimethylcyclohex-1-en-1-yl]methyl}piperazin-1-yl)-N-[(4-{[(2S)-1,4-dioxan-2-ylmethyl]amino}-3-nitrophenyl)sulfonyl]-2-(1H-pyrrolo[2,3-b]pyridin-5-yloxy)benzamide Example 9A (R)-(1,4-dioxan-2-yl)methyl methanesulfonate The title compound was prepared by substituting R-(−)-epichlorohydrin for S-(+)-epichlorohydrin in EXAMPLE 1K.

Example 9B (S)-2-(azidomethyl)-1,4-dioxane

The title compound was prepared by substituting EXAMPLE 9A for EXAMPLE 1K in EXAMPLE 1L.

Example 9C (S)-(1,4-dioxan-2-yl)methanamine

EXAMPLE 9B (400 mg) was dissolved in tetrahydrofuran (15 mL), cooled to 0° C., and lithium aluminum hydride (2.0 mL, 2.0M in tetrahydrofuran) was added. The reaction mixture was stirred at 0° C. for 50 minutes, then at room temperature for another 75 minutes. The reaction mixture was cooled to 0° C., then water (0.16 mL) was carefully added, followed by 20% aqueous NaOH (0.16 mL), and additional water (0.48 mL). The mixture was stirred for 15 minutes, $MgSO_4$ was added and diethylether was added (20 mL). The mixture was stirred for 15 minutes, filtered through diatomaceous earth, and rinsed with diethylether. Concentration of the filtrate gave the title compound which was used in the next step without additional purification.

Example 9D (S)-4-((1,4-dioxan-2-yl)methylamino)-3-nitrobenzenesulfonamide

The title compound was prepared by substituting EXAMPLE 9C for EXAMPLE 1M in EXAMPLE 1N.

Example 9E 4-(4-{[2-(4-chlorophenyl)-4,4-dimethylcyclohex-1-en-1-yl]methyl}piperazin-1-yl)-N-[(4-{[(2S)-1,4-dioxan-2-ylmethyl]amino}-3-nitrophenyl)sulfonyl]-2-(1H-pyrrolo[2,3-b]pyridin-5-yloxy)benzamide The title compound was prepared by substituting EXAMPLE 9D for EXAMPLE 1N in EXAMPLE 1O. $^{1}$H NMR (400 MHz, dimethylsulfoxide-$d_6$) δ ppm 11.65 (s, 1H), 8.55 (t, 1H), 8.54 (d, 1H), 8.01 (d, 1H), 7.81 (dd, 1H), 7.50 (m, 3H), 7.32 (d, 2H), 7.07 (d, 1H), 7.02 (d, 2H), 6.66 (dd, 1H), 6.37 (m, 1H), 6.18 (d, 1H), 3.77 (m, 3H), 3.63 (m, 2H), 3.47 (m, 2H), 3.31 (m, 2H), 3.06 (br m, 4H), 2.74 (br s, 2H), 2.19 (br m, 4H), 2.13 (br m, 2H), 1.94 (br m, 2H), 1.37 (t, 2H), 0.90 (s, 6H).

Example 10

4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-pyrrolo[2,3-b]pyridin-5-yloxy)benzamide Example 10A 4-(((4-(hydroxymethyl)tetrahydro-2H-pyran-4-yl)methyl)amino)-3-nitrobenzenesulfonamide The title compound was prepared by substituting (4-(aminomethyl)tetrahydro-2H-pyran-4-yl)methanol for EXAMPLE 1M in EXAMPLE 1N.

Example 10B 4-(((4-(((tert-butyldimethylsilyl)oxy)methyl)tetrahydro-2H-pyran-4-yl)methyl)amino)-3-nitrobenzenesulfonamide EXAMPLE 10A (648 mg) was dissolved in N,N-dimethylformamide (9 mL), and tert-butyldimethylsilyl trifluoromethanesulfonate (546 mg) was added. The solution was stirred at room temperature for 16 hours, and the solvent was removed under vacuum. The crude material was purified by flash column chromatography on silica gel using 50-70% ethyl acetate in heptanes.

Example 10C 2-((1H-pyrrolo[2,3-b]pyridin-5-yl)oxy)-N-((4-(((4-(((tert-butyldimethylsilyl)oxy)methyl)tetrahydro-2H-pyran-4-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide The title compound was prepared by substituting EXAMPLE 10B for EXAMPLE 1N in EXAMPLE 1O.

Example 10D 4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-pyrrolo[2,3-b]pyridin-5-yloxy)benzamide EXAMPLE 10C (488 mg) was dissolved in tetrahydrofuran (3 mL Tetrabutylammonium fluoride (1M in tetrahydrofuran, 1.45 mL) was added, and the solution was stirred at room temperature for 30 minutes. The reaction mixture was quenched with a saturated aqueous solution of sodium bicarbonate and diluted with ethyl acetate. The phases were separated, and the organic phase was washed with brine, and then dried on anhydrous sodium sulfate. After filtration and concentration, the crude material was purified by flash column chromatography on silica gel using ethyl acetate, increasing to 5-10% methanol in dichloromethane. $^1$H NMR (300 MHz, dimethylsulfoxide-$d_6$) δ ppm 11.69 (s, 1H), 9.08 (t, 1H), 8.59 (d, 1H), 8.08 (d, 1H), 7.83 (dd, 1H), 7.56-7.52 (m, 3H), 7.38 (d, 2H), 7.18 (d, 1H), 7.08 (d, 2H), 6.72 (dd, 1H), 6.43 (dd, 1H), 6.24 (d, 1H), 5.26 (t, 1H), 3.68-3.58 (m, 4H), 3.56 (d, 2H), 3.10 (bs, 4H), 3.05 (m, 2H), 2.77 (bs, 2H), 2.27-2.15 (m, 6H), 1.99 (bs, 2H), 1.51 (m, 4H), 1.42 (t, 2H), 0.96 (s, 6H).

Example 11

4-(4-{[2-(4-chlorophenyl)-4,4-dimethylcyclohex-1-en-1-yl]methyl}piperazin-1-yl)-N-{[4-({[3-(hydroxymethyl)oxetan-3-yl]methyl}amino)-3-nitrophenyl]sulfonyl}-2-(1H-pyrrolo[2,3-b]pyridin-5-yloxy)benzamide Example 11A 4-(((3-(hydroxymethyl)oxetan-3-yl)methyl)amino)-3-nitrobenzenesulfonamide The title compound was prepared by substituting (3-(aminomethyl)oxetan-3-yl)methanol for EXAMPLE 1M in EXAMPLE 1N.

Example 11B 4-(((3-(((tert-butyldimethylsilyl)oxy)methyl)oxetan-3-yl)methyl)amino)-3-nitrobenzenesulfonamide The title compound was prepared by substituting EXAMPLE 11A for EXAMPLE 10A in EXAMPLE 10B.

Example 11C 2-((1H-pyrrolo[2,3-b]pyridin-5-yl)oxy)-N-((4-(((3-(((tert-butyldimethylsilyl)oxy)methyl)oxetan-3-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)benzamide The title compound was prepared by substituting EXAMPLE 11B for EXAMPLE 1N in EXAMPLE 1O.

Example 11D 4-(4-{[2-(4-chlorophenyl)-4,4-dimethylcyclohex-1-en-1-yl]methyl}piperazin-1-yl)-N-{[4-({[3-(hydroxymethyl)oxetan-3-yl]methyl}amino)-3-nitrophenyl]sulfonyl}-2-(1H-pyrrolo[2,3-b]pyridin-5-yloxy)benzamide The title compound was prepared by substituting EXAMPLE 11C for EXAMPLE 10C in EXAMPLE 10D. $^1$H NMR (300 MHz, dimethylsulfoxide-$d_6$) δ ppm 11.65 (s, 1H), 11.40 (bs, 1H), 8.90 (t, 1H), 8.56 (d, 1H), 8.04 (d, 1H), 7.83 (dd, 1H), 7.53-7.47 (m, 3H), 7.34 (d, 2H), 7.13 (d, 1H), 7.04 (d, 2H), 6.68 (dd, 1H), 6.39 (dd, 1H), 6.20 (d, 1H), 5.34 (t, 1H), 4.37 (s, 4H), 3.77 (d, 2H), 3.69 (d, 2H), 3.07 (bs, 4H), 2.74 (bs, 2H), 2.25-2.11 (m, 6H), 1.95 (bs, 2H), 1.38 (t, 2H), 0.92 (s, 6H).

Example 12

4-(4-{[2-(4-chlorophenyl)-4,4-dimethylcyclohex-1-en-1-yl]methyl}piperazin-1-yl)-N-({4-[(3-hydroxy-3-methylbutyl)amino]-3-nitrophenyl}sulfonyl)-2-(1H-pyrrolo[2,3-b]pyridin-5-yloxy)benzamide Example 12A 4-((3-hydroxy-3-methylbutyl)amino)-3-nitrobenzenesulfonamide The title compound was prepared by substituting 4-amino-2-methylbutan-2-ol for EXAMPLE 1M in EXAMPLE 1N.

Example 12B 4-(4-{[2-(4-chlorophenyl)-4,4-dimethylcyclohex-1-en-1-yl]methyl}piperazin-1-yl)-N-({4-[(3-hydroxy-3-methylbutyl)amino]-3-nitrophenyl}sulfonyl)-2-(1H-pyrrolo[2,3-b]pyridin-5-yloxy)benzamide The title compound was prepared by substituting EXAMPLE 12A for EXAMPLE 1N in EXAMPLE 1O. $^1$H NMR (300 MHz, dimethylsulfoxide-$d_6$) δ ppm 11.67 (s, 1H), 11.37 (bs, 1H), 8.95 (t, 1H), 8.56 (d, 1H), 8.05 (d, 1H), 7.82 (dd, 1H), 7.54 (d, 1H), 7.52-7.48 (m, 2H), 7.34 (d, 2H), 7.06-6.98 (m, 3H), 6.68 (dd, 1H), 6.39 (dd, 1H), 6.20 (d, 1H), 4.67 (s, 1H), 3.45 (q, 2H), 3.07 (bs, 4H), 2.75 (bs, 2H), 2.25-2.11 (m, 6H), 1.95 (bs, 2H), 1.74 (t, 2H), 1.38 (t, 2H), 1.18 (s, 6H), 0.92 (s, 6H).

Example 13

4-(4-{[2-(4-chlorophenyl)-4,4-dimethylcyclohex-1-en-1-yl]methyl}piperazin-1-yl)-N-({4-[(3-hydroxytricyclo[3.3.1.1$^{3,7}$]dec-1-yl)amino]-3-nitrophenyl}sulfonyl)-2-(1H-pyrrolo[2,3-b]pyridin-5-yloxy)benzamide Example 13A 4-((3-hydroxyadamantan-1-yl)amino)-3-nitrobenzenesulfonamide The title compound was prepared by substituting 3-aminoadamantan-1-ol for EXAMPLE 1M in EXAMPLE 1N.

Example 13B 4-(4-{[2-(4-chlorophenyl)-4,4-dimethylcyclohex-1-en-1-yl]methyl}piperazin-1-yl)-N-[(4-{[3-hydroxytricyclo[3.3.1.1$^{3,7}$]dec-1-yl]amino}-3-nitrophenyl)sulfonyl]-2-(1H-pyrrolo[2,3-b]pyridin-5-yloxy)benzamide The title compound was prepared by substituting EXAMPLE 13A for EXAMPLE 1N in EXAMPLE 1O. $^1$H NMR (300 MHz, dimethylsulfoxide-$d_6$) δ ppm 11.67 (s, 1H), 11.45 (bs, 1H), 8.57 (d, 1H), 8.45 (s, 1H), 8.04 (d, 1H), 7.82 (dd, 1H), 7.57-7.47 (m, 3H), 7.41-7.32 (m, 3H), 7.04 (d, 2H), 6.68 (dd, 1H), 6.39 (dd, 1H), 6.18 (d, 1H), 4.68 (s, 1H), 3.06 (bs, 4H), 2.75 (bs, 2H), 2.28-2.10 (m, 8H), 1.97-1.88 (m, 8H), 1.72-1.55 (m, 4H), 1.48 (d, 2H), 1.38 (t, 2H), 0.92 (s, 6H).

Example 14

4-(4-{[2-(4-chlorophenyl)-4,4-dimethylcyclohex-1-en-1-yl]methyl}piperazin-1-yl)-N-[(3-nitro-4-{[(1R,5S,6S)-3-oxabicyclo[3.1.0]hex-6-ylmethyl]amino}phenyl)sulfonyl]-2-(1H-pyrrolo[2,3-b]pyridin-5-yloxy)benzamide Example 14A tert-butyl (1R,5S,6R)-3-oxabicyclo[3.1.0]hexane-6-carboxylate Tert-butyl diazoacetate (135 g, 15% in toluene) was added to 2,5-dihydrofuran (100 g) and rhodium (II) acetate dimer (0.95 g) in dichloromethane (250 mL) over 4 hours, and the reaction mixture was stirred for 24 hours. The reaction mixture was concentrated and the crude product was chromatographed on silica gel with 1-15% ethyl acetate/hexanes to separately give the product and its diastereomer in a 2:1 ratio.

Example 14B (1R,5S,6R)-3-oxabicyclo[3.1.0]hexane-6-carboxylic acid

EXAMPLE 14A (4 g) was stirred in dichloromethane (20 mL) and TFA (20 mL) for 2 hours, and was concentrated. The crude material was taken up in dichloromethane (200 mL) and saturated $Na_2CO_3$ solution (20 mL). The reaction mixture was stirred for 10 minutes, and the organic layer was separated and dried over $Na_2SO_4$. After filtration, the mixture was concentrated to afford the title compound.

Example 14C (1R,5S,6R)-3-oxabicyclo[3.1.0]hexane-6-carboxamide

Oxalyl chloride (2.05 mL) was added to EXAMPLE 14B (4 g) in dichloromethane (40 mL) and the reaction mixture was stirred for 24 hours, and concentrated. The crude material was taken up in dichloromethane (30 mL), saturated $NH_4OH$ solution (3 mL) was added, and the reaction mixture was stirred for 30 minutes. Dichloromethane (30 mL) and saturated $Na_2CO_3$ solution (20 mL) were added, and the organic layer was separated, dried over $Na_2SO_4$, filtered, and concentrated to afford the title compound.

Example 14D 3-nitro-4-{[(1R,5S,6S)-3-oxabicyclo[3.1.0]hex-6-ylmethyl]amino}benzenesulfonamide Borane-tetrahydrofuran complex (2.5 mL, 1M in tetrahydrofuran) was added to EXAMPLE 14C (160 mg) in tetrahydrofuran (2 mL) and the reaction mixture was stirred for 24 hours at 50° C. The reaction mixture was quenched by the slow addition of 1M aqueous HCl, diluted with dichloromethane (20 mL), and minimal concentrated NaOH solution was added to basicify the solution. To this mixture 4-fluoro-3-nitrobenzenesulfonamide (277 mg) and triethylamine (2 mL) were added and the reaction mixture was stirred for 1 hours. The reaction mixture was concentrated and the crude product was chromatographed on silica gel with 10-100% ethyl acetate/hexanes to afford the title compound.

Example 14E 4-(4-{[2-(4-chlorophenyl)-4,4-dimethylcyclohex-1-en-1-yl]methyl}piperazin-1-yl)-N-[(3-nitro-4-{[(1R,5S,6S)-3-oxabicyclo[3.1.0]hex-6-ylmethyl]amino}phenyl)sulfonyl]-2-(1H-pyrrolo[2,3-b]pyridin-5-yloxy)benzamide The title compound was prepared by substituting EXAMPLE 14D for EXAMPLE 1N in EXAMPLE 1O. $^1$H NMR (300 MHz, dimethylsulfoxide-$d_6$) δ 11.68 (s, 1H), 11.40 (br s, 1H), 8.60 (m, 1H), 8.58 (s, 1H), 8.05 (s, 1H), 7.83 (d, 1H), 7.51 (m, 2H), 7.34 (d, 2H), 7.09 (d, 1H), 7.04 (d, 2H), 6.69 (d, 1H), 6.39 (d, 1H), 6.20 (s, 1H), 3.74 (d, 2H), 3.54 (m, 2H), 3.31 (m, 3H), 3.07 (m, 4H), 2.76 (s, 2H), 2.20 (s, 4H), 2.14 (m, 2H), 1.95 (s, 2H), 1.71 (m, 2H), 1.38 (m, 2H), 1.05 (m, 1H), 0.92 (m, 6H).

Example 15

4-(4-{[2-(4-chlorophenyl)-4,4-dimethylcyclohex-1-en-1-yl]methyl}piperazin-1-yl)-N-[(4-{[(3-hydroxyoxetan-3-yl)methyl]amino}-3-nitrophenyl)sulfonyl]-2-(1H-pyrrolo[2,3-b]pyridin-5-yloxy)benzamide Example 15A 4-(((3-hydroxyoxetan-3-yl)methyl)amino)-3-nitrobenzenesulfonamide The title compound was prepared by substituting 3-(aminomethyl)oxetan-3-ol for EXAMPLE 1M in EXAMPLE 1N.

Example 15B 4-(4-{[2-(4-chlorophenyl)-4,4-dimethylcyclohex-1-en-1-yl]methyl}piperazin-1-yl)-N-[(4-{[(3-hydroxyoxetan-3-yl)methyl]amino}-3-nitrophenyl)sulfonyl]-2-(1H-pyrrolo[2,3-b]pyridin-5-yloxy)benzamide The title compound was prepared by substituting EXAMPLE 15A for EXAMPLE 1N in EXAMPLE 1O. $^1$H NMR (300 MHz, dimethylsulfoxide-$d_6$) δ ppm 11.66 (s, 1H), 11.38 (bs, 1H), 8.56 (d, 1H), 8.54 (t, 1H), 8.05 (d, 1H), 7.83 (dd, 1H), 7.54-7.48 (m, 3H), 7.34 (dt, 2H), 7.19 (d, 1H), 7.04 (dt, 2H), 6.68 (dd, 1H), 6.39 (dd, 1H), 6.35 (s, 1H), 6.20 (d, 1H), 4.47 (dd, 4H), 3.72 (d, 2H), 3.07 (bs, 4H), 2.75 (bs, 2H), 2.25-2.10 (m, 6H), 1.95 (bs, 2H), 1.38 (t, 2H), 0.92 (s, 6H).

Example 16

4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}-2-(1H-pyrrolo[2,3-b]pyridin-5-yloxy)benzamide Example 16A 4-(morpholinoamino)-3-nitrobenzenesulfonamide The title compound was prepared by substituting morpholin-4-amine for EXAMPLE 1M in EXAMPLE 1N.

Example 16B 4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}-2-(1H-pyrrolo[2,3-b]pyridin-5-yloxy)benzamide The title compound was prepared by substituting EXAMPLE 16A for EXAMPLE 1N in EXAMPLE 1O. $^1$H NMR (300 MHz, dimethylsulfoxide-$d_6$) δ ppm 11.67 (s, 1H), 11.43 (bs, 1H), 9.26 (s, 1H), 8.54 (d, 1H), 8.04 (d, 1H), 7.83 (dd, 1H), 7.64 (d, 1H), 7.54-7.47 (m, 3H), 7.34 (d, 2H), 7.04 (d, 2H), 6.67 (dd, 1H), 6.39 (dd, 1H), 6.19 (d, 1H), 3.90-3.52 (m, 4H), 3.07 (bs, 4H), 2.85 (bs, 4H), 2.75 (bs, 2H), 2.26-2.11 (m, 6H), 1.95 (bs, 2H), 1.38 (t, 2H), 0.92 (s, 6H).

Example 17 methyl 4-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}tetrahydro-2H-pyran-4-carboxylate Example 17A methyl 4-(((2-nitro-4-sulfamoylphenyl)amino)methyl)tetrahydro-2H-pyran-4-carboxylate The title compound was prepared by substituting methyl 4-(aminomethyl)tetrahydro-2H-pyran-4-carboxylate for EXAMPLE 1M in EXAMPLE 1N.

Example 17B methyl 4-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}tetrahydro-2H-pyran-4-carboxylate The title compound was prepared by substituting EXAMPLE 17A for EXAMPLE 1N in EXAMPLE 1O. $^1$H NMR (300 MHz, dimethylsulfoxide-$d_6$) δ ppm 11.67 (s, 1H), 11.41 (bs, 1H), 8.56 (d, 1H), 8.54 (t, 1H), 8.04 (d, 1H), 7.84 (dd, 1H), 7.53-7.46 (m, 3H), 7.34 (d, 2H), 7.13 (d, 1H), 7.04 (d, 2H), 6.68 (dd, 1H), 6.39 (dd, 1H), 6.19 (d, 1H), 3.79 (dt, 2H), 3.62 (s, 3H), 3.59 (d, 2H), 3.33 (m, 2H), 3.07 (bs, 4H), 2.75 (bs, 2H), 2.25-2.11 (m, 6H), 2.02 (d, 2H), 1.95 (bs, 2H), 1.62 (m, 2H), 1.38 (t, 2H), 0.92 (s, 6H).

Example 18

4-(4-{[2-(4-chlorophenyl)-4,4-dimethylcyclohex-1-en-1-yl]methyl}piperazin-1-yl)-N-({3-nitro-4-[2-(tetrahydro-2H-pyran-4-yl)hydrazinyl]phenyl}sulfonyl)-2-(1H-pyrrolo[2,3-b]pyridin-5-yloxy)benzamide Example 18A 4-hydrazinyl-3-nitrobenzenesulfonamide The title compound was prepared by substituting hydrazine monohydrate for EXAMPLE 1M in EXAMPLE 1N.

Example 18B 3-nitro-4-(2-(tetrahydro-2H-pyran-4-yl)hydrazinyl)benzenesulfonamide EXAMPLE 18A (250 mg) was taken up in dichloromethane (10 mL) and 1-methylpyrrolidinone (5 mL), then dihydro-2H-pyran-4(3H)-one (119 mg) was added, and the solution was stirred at room temperature for 20 minutes. Sodium triacetoxyborohydride (479 mg) was added, and the mixture was stirred at room temperature for 16 hours. The mixture was diluted with ethyl acetate, washed with a saturated aqueous sodium bicarbonate solution, washed with water two times, washed with brine, and dried on anhydrous sodium sulfate. After filtration and concentration, the crude material was recrystallized from ethyl acetate. The solid material was washed with diethyl ether, and dried under vacuum to afford the title compound.

Example 18C 4-(4-{[2-(4-chlorophenyl)-4,4-dimethylcyclohex-1-en-1-yl]methyl}piperazin-1-yl)-N-({3-nitro-4-[2-(tetrahydro-2H-pyran-4-yl)hydrazinyl]phenyl}sulfonyl)-2-(1H-pyrrolo[2,3-b]pyridin-5-yloxy)benzamide The title compound was prepared by substituting EXAMPLE 18B for EXAMPLE 1N in EXAMPLE 1O. $^1$H NMR (300 MHz, dimethylsulfoxide-$d_6$) δ ppm 11.65 (s, 1H), 10.81 (s, 1H), 8.56 (d, 1H), 8.02 (d, 1H), 7.90 (dd, 1H), 7.72 (d, 1H), 7.51-7.47 (m, 3H), 7.34 (d, 2H), 7.03 (d, 2H), 6.68 (dd, 1H), 6.37 (dd, 1H), 6.21 (d, 1H), 3.79 (m, 4H), 3.27 (td, 2H), 3.08 (bs, 4H), 2.77 (bs, 2H), 2.55 (dt, 4H), 2.25-2.11 (m, 6H), 1.95 (bs, 2H), 1.38 (t, 2H), 0.92 (s, 6H).

Example 19

4-(4-{[2-(4-chlorophenyl)-4,4-dimethylcyclohex-1-en-1-yl]methyl}piperazin-1-yl)-N-[(3-nitro-4-{[(4R)-oxepan-4-ylmethyl]amino}phenyl)sulfonyl]-2-(1H-pyrrolo[2,3-b]pyridin-5-yloxy)benzamide Example 19A oxepan-4-one To a stirred solution of dihydro-2H-pyran-4(3H)-one (8.5 g) and boron trifluoride diethyl etherate (15 mL) in dichloromethane (400 mL) at −25° C. was added (trimethylsilyl) diazomethane (60 mL, 120 mmol, 2.0 M in hexanes) slowly via syringe. The reaction mixture was stirred at −25° C. for 2.5 hours. The reaction mixture was diluted with water (300 mL) and extracted with dichloromethane (300 mL). The organic layer was separated, washed with 10:1 saturated aqueous $NH_4Cl$: saturated aqueous $NH_4OH$, washed with brine, dried over magnesium sulfate, filtered, and concentrated in vacuo. The resulting crude product was purified by silica gel chromatography to afford the title compound.

Example 19B oxepane-4-carbonitrile

The title compound was prepared by substituting EXAMPLE 19A for 1-oxaspiro[4.5]decan-8-one in EXAMPLE 4A.

Example 19C oxepan-4-ylmethanamine

The title compound was prepared by substituting EXAMPLE 19B for EXAMPLE 4A in EXAMPLE 4B.

Example 19D (R)-3-nitro-4-(oxepan-4-ylmethylamino)benzenesulfonamide

The title compound was prepared by substituting EXAMPLE 19C for EXAMPLE 1M in EXAMPLE 1N. The enantiomers were separated using a modified Berger Instruments PrepSFC™ system. A manual version of the Berger system was integrated with a Gilson 232 autosampler for sample injection and a Cavro MiniPrep™ pipettor customized for fraction collection at atmospheric pressure (Olson, J.; Pan, J.; Hochlowski, J.; Searle, P.; Blanchard, D. *JALA* 2002, 7, 69-74). Custom designed collection shoes allowed collection into 18×150 mm tubes and a methanol wash system allows washing of shoes between fractions to maximize recovery and avoid cross-contamination of fractions. The system was controlled using SFC ProNTo™ software (version 1.5.305.15) and an AbbVie developed Visual Basic application for autosampler and fraction collector control. The outlet pressure was 100 bar, oven temperature at 35° C., and mobile phase flow rate at 40 mL/minute. The column used was a Chiralpak IA, 21×250 mm, 5 micron. The mobile phase was 35% $CH_3OH$ (containing 0.3% diethylamine)/65% supercritical $CO_2$. Samples were injected as solutions in 1.9 mL $CH_3OH$:DMSO 1:1. The preparative SFC system was controlled using SFC ProNTo™ software (version 1.5.305.15) and custom software for autosampler and fraction collector control. Fractions were collected based upon UV signal threshold and on-line Thermo MSQ mass spectrometry was used for molecular mass confirmation, using ESI ionization in positive mode. Mass spectra were acquired using a Navigator 4.0 software and an AbbVie developed Visual Basic interface to communicate with SFC controlling software.

Example 19E 4-(4-{[2-(4-chlorophenyl)-4,4-dimethylcyclohex-1-en-1-yl]methyl}piperazin-1-yl)-N-[(3-nitro-4-{[(4R)-oxepan-4-ylmethyl]amino}phenyl)sulfonyl]-2-(1H-pyrrolo[2,3-b]pyridin-5-yloxy)benzamide The title compound was prepared by substituting EXAMPLE 19D for EXAMPLE 1N in EXAMPLE 1O. $^1$H NMR (300 MHz dimethylsulfoxide-$d_6$) δ ppm 11.67 (s, 1H), 8.49-8.67 (m, 2H), 8.04 (d, 1H), 7.80 (dd, 1H), 7.45-7.58 (m, 3H), 7.34 (d, 2H), 6.97-7.14 (m, 3H), 6.67 (dd, 1H), 6.39 (dd, 1H), 6.19 (d, 1H), 3.44-3.76 (m, 4H), 3.00-3.13 (m, 4H), 2.74 (s, 2H), 2.07-2.27 (m, 6H), 1.83-2.00 (m, 3H), 1.68-1.85 (m, 3H), 1.54-1.65 (m, 1H), 1.27-1.47 (m, 4H), 0.92 (s, 6H).

Example 20

4-(4-{[2-(4-chlorophenyl)-4,4-dimethylcyclohex-1-en-1-yl]methyl}piperazin-1-yl)-N-[(3-nitro-4-{[(4S)-oxepan-4-ylmethyl]amino}phenyl)sulfonyl]-2-(1H-pyrrolo[2,3-b]pyridin-5-yloxy)benzamide Example 20A (S)-3-nitro-4-((oxepan-4-ylmethyl)amino)benzenesulfonamide The title compound was also obtained as described in EXAMPLE 19D.

Example 20B 4-(4-{[2-(4-chlorophenyl)-4,4-dimethylcyclohex-1-en-1-yl]methyl}piperazin-1-yl)-N-[(3-nitro-4-{[(4S)-oxepan-4-ylmethyl]amino}phenyl)sulfonyl]-2-(1H-pyrrolo[2,3-b]pyridin-5-yloxy)benzamide The title compound was prepared by substituting EXAMPLE 20A for EXAMPLE 1N in EXAMPLE 1O. $^1$H NMR (300 MHz dimethylsulfoxide-$d_6$) δ ppm 11.67 (s, 1H), 8.49-8.67 (m, 2H), 8.04 (d, 1H), 7.80 (dd, 1H), 7.45-7.58 (m, 3H), 7.34 (d, 2H), 6.97-7.14 (m, 3H), 6.67 (dd, 1H), 6.39 (dd, 1H), 6.19 (d, 1H), 3.44-3.76 (m, 4H), 3.00-3.13 (m, 4H), 2.74 (s, 2H), 2.07-2.27 (m, 6H), 1.83-2.00 (m, 3H), 1.68-1.85 (m, 3H), 1.54-1.65 (m, 1H), 1.27-1.47 (m, 4H), 0.92 (s, 6H).

Example 21

4-(4-{[2-(4-chlorophenyl)-4,4-dimethylcyclohex-1-en-1-yl]methyl}piperazin-1-yl)-N-[(4-{[(4-methyltetrahydro-2H-pyran-4-yl)methyl]amino}-3-nitrophenyl)sulfonyl]-2-(1H-pyrrolo[2,3-b]pyridin-5-yloxy)benzamide

Example 21A 4-(((4-methyltetrahydro-2H-pyran-4-yl)methyl)amino)-3-nitrobenzenesulfonamide Sodium triacetoxyborohydride (3513 mg) was added to trifluoromethylacetic acid (30 mL). 4-Amino-3-nitrobenzenesulfonamide (800 mg) was added and the solution was stirred at room temperature for 10 minutes. 4-Methyltetrahydro-2H-pyran-4-carbaldehyde (991 mg) dissolved in dichloromethane (10 mL) was added drop-wise. After the addition, the mixture was stirred at room temperature for 16 hours. The mixture was poured over an ice-cold saturated solution of sodium bicarbonate and extracted with ethyl acetate. The organic layer was washed with water and brine and dried on anhydrous sodium sulfate. After filtration and concentration, the crude material was purified by recrystallization from ethyl acetate.

Example 21B 4-(4-{[2-(4-chlorophenyl)-4,4-dimethylcyclohex-1-en-1-yl]methyl}piperazin-1-yl)-N-[(4-{[(4-methyltetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting EXAMPLE 21A for EXAMPLE 1N in EXAMPLE 1O. $^1$H NMR (300 MHz, dimethylsulfoxide-$d_6$) δ ppm 11.67 (s, 1H), 11.38 (bs, 1H), 8.56 (d, 1H), 8.48 (t, 1H), 8.03 (d, 1H), 7.80 (dd, 1H), 7.54-7.46 (m, 3H), 7.34 (d, 2H), 7.22 (d, 1H), 7.04 (d, 2H), 6.68 (dd, 1H), 6.38 (dd, 1H), 6.20 (d, 1H), 3.72-3.63 (m, 2H), 3.52 (m, 2H), 3.30 (m, 2H), 3.07 (bs, 4H), 2.75 (bs, 2H), 2.25-2.10 (m, 6H), 1.95 (bs, 2H), 1.53 (m, 2H), 1.38 (t, 2H), 1.31 (d, 2H), 1.06 (s, 3H), 0.92 (s, 6H).

Example 22

4-(4-{[2-(4-chlorophenyl)-4,4-dimethylcyclohex-1-en-1-yl]methyl}piperazin-1-yl)-N-({3-nitro-4-[(tetrahydro-2H-thiopyran-4-ylmethyl)amino]phenyl}sulfonyl)-2-(1H-pyrrolo[2,3-b]pyridin-5-yloxy)benzamide

Example 22A 3-nitro-4-(((tetrahydro-2H-thiopyran-4-yl)methyl)amino)benzenesulfonamide The title compound was prepared by substituting (tetrahydro-2H-thiopyran-4-yl)methanamine hydrochloride for EXAMPLE 1M in EXAMPLE 1N.

Example 22B 4-(4-{[2-(4-chlorophenyl)-4,4-dimethylcyclohex-1-en-1-yl]methyl}piperazin-1-yl)-N-({3-nitro-4-[(tetrahydro-2H-thiopyran-4-ylmethyl)amino]phenyl}sulfonyl)-2-(1H-pyrrolo[2,3-b]pyridin-5-yloxy)benzamide The title compound was prepared by substituting EXAMPLE 22A for EXAMPLE 1N in EXAMPLE 1O. $^1$H NMR (300 MHz, dimethylsulfoxide-$d_6$) δ ppm 11.68 (s, 1H), 11.37 (bs, 1H), 8.59 (t, 1H), 8.56 (d, 1H), 8.04 (d, 1H), 7.80 (dd, 1H), 7.55-7.47 (m, 3H), 7.34 (d, 2H), 7.08 (d, 1H), 7.04 (d, 2H), 6.68 (dd, 1H), 6.39 (dd, 1H), 6.19 (d, 1H), 3.28 (t, 2H), 3.07 (bs, 4H), 2.75 (bs, 2H), 2.58 (m, 4H), 2.25-2.11 (m, 6H), 2.02 (dd, 2H), 1.95 (bs, 2H), 1.70 (m, 1H), 1.38 (t, 2H), 1.36-1.28 (m, 2H), 0.92 (s, 6H).

Example 23

4-(4-{[2-(4-chlorophenyl)-4,4-dimethylcyclohex-1-en-1-yl]methyl}piperazin-1-yl)-N-({3-nitro-4-[(oxetan-3-ylmethyl)amino]phenyl}sulfonyl)-2-(1H-pyrrolo[2,3-b]pyridin-5-yloxy)benzamide

Example 23A 3-nitro-4-((oxetan-3-ylmethyl)amino)benzenesulfonamide

The title compound was prepared by substituting oxetan-3-ylmethanamine for EXAMPLE 1M in EXAMPLE 1N.

Example 23B 4-(4-{[2-(4-chlorophenyl)-4,4-dimethylcyclohex-1-en-1-yl]methyl}piperazin-1-yl)-N-({3-nitro-4-[(oxetan-3-ylmethyl)amino]phenyl}sulfonyl)-2-(1H-pyrrolo[2,3-b]pyridin-5-yloxy)benzamide The title compound was prepared by substituting EXAMPLE 23A for EXAMPLE 1N in EXAMPLE 1O. $^1$H NMR (300 MHz, dimethylsulfoxide-$d_6$) δ ppm 11.67 (s, 1H), 11.39 (bs, 1H), 8.66 (t, 1H), 8.55 (d, 1H), 8.04 (d, 1H), 7.80 (dd, 1H), 7.54-7.46 (m, 3H), 7.34 (d, 2H), 7.09 (d, 1H), 7.03 (d, 2H), 6.68 (dd, 1H), 6.39 (dd, 1H), 6.20 (d, 1H), 4.66 (dd, 2H), 4.36 (t, 2H), 4.01 (bs, 1H), 3.71 (t, 2H), 3.07 (bs, 4H), 2.75 (bs, 2H), 2.26-2.10 (m, 6H), 1.95 (bs, 2H), 1.38 (t, 2H), 0.92 (s, 6H).

Example 24

4-(4-{[2-(4-chlorophenyl)-4,4-dimethylcyclohex-1-en-1-yl]methyl}piperazin-1-yl)-N-{[4-({[(2R,5R)-5-methyl-1,4-dioxan-2-yl]methyl}amino)-3-nitrophenyl]sulfonyl}-2-(1H-pyrrolo[2,3-b]pyridin-5-yloxy)benzamide Example 24A (R)-((2-(allyloxy)propoxy)methyl)benzene (R)-1-(benzyloxy)propan-2-ol (5 g) and allyl bromide (3.5 mL) were dissolved in tetrahydrofuran (45 mL). The mixture was cooled to 5° C., and 95% NaH (1.1 g) was added in four portions over 10 minutes. The mixture was allowed to warm temperature and stirred under a drying tube overnight. The reaction was diluted with water and extracted with ether. The organic layer was washed with brine and the combined aqueous layers were back-extracted with ether. The combined organic layers were dried over $Na_2SO_4$. Filtration and concentration of the filtrate afforded the title compound which was used in the next step without further purification.

Example 24B 2-(((R)-1-(benzyloxy)propan-2-yloxy)methyl)oxirane

EXAMPLE 24A (6.2 g) was dissolved in dichloromethane (200 mL), cooled to 0° C., m-chloroperoxybenzoic acid (13.5 g) was added. The reaction mixture was stirred cold for 1 hour, then stirred at room temperature overnight. Aqueous $Na_2SO_3$ (10%, 100 mL) was added, the mixture was stirred for 5 minutes, and the layers were separated. The organic layer was washed with saturated $NaHCO_3$ (2×150 mL), and with brine. After drying over $Na_2SO_4$, filtration and concentration, the crude material was dissolved in diethylether, then washed with 10% $Na_2S_2O_3$, 3 times with saturated $NaHCO_3$, and brine. After drying over $Na_2SO_4$, filtration and concentration gave a crude oil. The crude material was chromatographed on silica gel with 85/15 heptanes/ethyl acetate to afford the title compound.

Example 24C (S)-2-(((R)-1-(benzyloxy)propan-2-yloxy)methyl)oxirane

R,R-(salen)Co(II) complex (56 mg) was added to neat EXAMPLE 24B (4.0 g), then tetrahydrofuran was added (180 μL), followed by acetic acid (20.7 μL). The mixture was cooled to 0° C., water was added (180 μL) and the reaction was allowed to come to room temperature overnight in an open 25 mL flask. The reaction was then directly chromatographed on silica gel with 85/15 heptanes/ethyl acetate to afford the title compound.

Example 24D (R)-2-((S)-oxiran-2-ylmethoxy)propan-1-ol

EXAMPLE 24C (2.3 g) was dissolved in ethyl acetate (65 mL), $Pd(OH)_2$ on carbon (20% Pd dry wt/overall 50% water, 100 mg) was added and the reaction mixture was stirred under a hydrogen balloon for 2 hours. After filtration through diatomaceous earth and concentration the incomplete reaction was rerun, this time using tetrahydrofuran in place of ethyl acetate. The crude material was chromatographed on silica gel with 35/65 heptanes/ethyl acetate to afford the title compound.

Example 24E ((2R,5R)-5-methyl-1,4-dioxan-2-yl)methanol

EXAMPLE 24D (800 mg) was dissolved in dichloromethane (45 mL), (1S)-(+)-camphorsulfonic acid (415 mg) was added, and the reaction mixture was stirred at room temperature overnight. Saturated $NaHCO_3$ was added, the layers were separated, and the aqueous layer was extracted with dichloromethane (3×50 mL). The combined organic layers were dried over $Na_2SO_4$. After filtration and concentration, the crude material was chromatographed on silica gel with 35/65 heptanes/ethyl acetate to afford the title compound.

Example 24F ((2S,5R)-5-methyl-1,4-dioxan-2-yl)methyl methanesulfonate

EXAMPLE 24E (400 mg) and triethylamine (0.58 mL) were dissolved in dichloromethane (12 mL). The reaction mixture was cooled to 0° C., and methanesulfonyl chloride (0.28 mL) was added dropwise. The reaction mixture was stirred at room temperature for 1 hour. Saturated $NaHCO_3$ (10 mL) was added, and the aqueous layer was extracted with dichloromethane (3×7 mL). The combined organic layers were dried over $Na_2SO_4$. Filtration and concentration of the filtrate gave the title compound that was used in the next step without further purification.

Example 24G (2R,5R)-2-(azidomethyl)-5-methyl-1,4-dioxane

The title compound was prepared by substituting EXAMPLE 24F for EXAMPLE 1K in EXAMPLE 1L.

Example 24H ((2R,5R)-5-methyl-1,4-dioxan-2-yl)methanamine

The title compound was prepared by substituting EXAMPLE 24G for EXAMPLE 9B in EXAMPLE 9C.

Example 24I 4-(((2R,5R)-5-methyl-1,4-dioxan-2-yl)methylamino)-3-nitrobenzenesulfonamide The title compound was prepared by substituting EXAMPLE 24H for EXAMPLE 1M in EXAMPLE 1N.

Example 24J 4-(4-{[2-(4-chlorophenyl)-4,4-dimethylcyclohex-1-en-1-yl]methyl}piperazin-1-yl)-N-{[4-({[(2R,5R)-5-methyl-1,4-dioxan-2-yl]methyl}amino)-3-nitrophenyl]sulfonyl}-2-(1H-pyrrolo[2,3-b]pyridin-5-yloxy)benzamide The title compound was prepared by substituting EXAMPLE 24I for EXAMPLE 1N in EXAMPLE 1O. $^1H$ NMR (400 MHz, dimethylsulfoxide-$d_6$) δ ppm 11.65 (s, 1H), 8.57 (d, 1H), 8.55 (t, 1H), 8.03 (d, 1H), 7.83 (dd, 1H), 7.50 (m, 3H), 7.34 (d, 2H), 7.10 (d, 1H), 7.02 (d, 2H), 6.67 (dd, 1H), 6.38 (m, 1H), 6.20 (d, 1H), 3.86, 3.78, 3.70, 3.67 (all m, 5H), 3.54, 3.49 (both m, 3H), 3.08 (br m, 4H), 2.76 (br s, 2H), 2.20 (br m, 4H), 2.13 (br m, 2H), 1.94 (br m, 2H), 1.37 (t, 2H), 1.09 (d, 3H), 0.92 (s, 6H).

Example 25

4-(4-{[2-(4-chlorophenyl)-4,4-dimethylcyclohex-1-en-1-yl]methyl}piperazin-1-yl)-N-[(4-{[(6-hydroxy-1,4-dioxepan-6-yl)methyl]amino}-3-nitrophenyl)sulfonyl]-2-(1H-pyrrolo[2,3-b]pyridin-5-yloxy)benzamide Example 25A 1,4-dioxepan-6-one To a cooled (0° C.) solution of ethane-1,2-diol (12.9 g) and ethyl 2-diazoacetate (47.5 g) in dichloromethane (400 mL) was added dropwise $BF_3Et_2O$ (0.3 mL). Gas evolution was observed upon the addition. The temperature was allowed to rise to room temperature and the mixture was stirred for 24 hours. The mixture was then concentrated under vacuum and the residue was used directly in the next reaction without further purification. To a solution of diethyl 2,2'-(ethane-1,2-diylbis(oxy))diacetate (52.75 g) in DMF was added tert-butoxylithium (36 g). The mixture was stirred at 90° C. overnight. The mixture was poured over 10% aqueous HCl (200 mL) and extracted three times with ethyl acetate. The combined extracts were washed three times with water, and brine, and dried over $Na_2SO_4$. Filtration and concentration gave crude product which was used in the next reaction without further purification. A mixture of ethyl 6-oxo-1,4-dioxepane-5-carboxylate (16.2 g) in 10% aqueous HCl (100 mL) was stirred at reflux for 4 hours. The mixture was cooled, and extracted three times with ethyl ether. The combined extracts were washed with brine, and dried over $Na_2SO_4$. After filtration, concentration afforded the title compound.

Example 25B 6-(nitromethyl)-1,4-dioxepan-6-ol

To a solution of sodium ethoxide (14 g, 21% w) in ethanol (20 mL) was added a solution of EXAMPLE 25A (3.2 g) and nitromethane (3.75 g). The reaction mixture was stirred for 4 hours. The reaction mixture was poured in aqueous $NH_4Cl$ (200 mL). The aqueous layer was extracted three times with ethyl acetate. The organic layers were combined and dried with $MgSO_4$. After filtration and concentration, the crude material was purified with on an Analogix System with a 600 g column, eluting with 0-40% ethyl acetate in hexanes to afford the title compound.

Example 25C 6-(aminomethyl)-1,4-dioxepan-6-ol

To a solution of EXAMPLE 25B (1.2 g) in ethanol (60 mL) was added Pd/C(10%, 120 mg). The mixture was stirred under a hydrogen balloon overnight. The mixture was filtered and concentrated to afford the crude product which was used directly in the next reaction without further purification.

Example 25D 4-(((6-hydroxy-1,4-dioxepan-6-yl)methyl)amino)-3-nitrobenzenesulfonamide The title compound was prepared by substituting EXAMPLE 25C for EXAMPLE 1M in EXAMPLE 1N.

Example 25E 4-(4-{[2-(4-chlorophenyl)-4,4-dimethylcyclohex-1-en-1-yl]methyl}piperazin-1-yl)-N-[(4-{[(6-hydroxy-1,4-dioxepan-6-yl)methyl]amino}-3-nitrophenyl)sulfonyl]-2-(1H-pyrrolo[2,3-b]pyridin-5-yloxy)benzamide The title compound was prepared by substituting EXAMPLE 25D for EXAMPLE 1N in EXAMPLE 1O. $^1H$ NMR (400 MHz, dimethylsulfoxide-$d_6$) δ ppm 11.67 (s, 1H), 8.64 (t, 1H), 8.57 (d, 1H), 8.05 (d, 1H), 7.81 (dd, 1H), 7.45-7.57 (m, 3H), 7.33 (t, 2H), 7.11 (d, 1H), 6.97-7.07 (m, 2H), 6.68 (dd, 1H), 6.39 (dd, 1H), 6.19 (d, 1H), 5.46-5.58 (m, 1H), 3.58-3.83 (m, 9H), 3.34-3.46 (m, 3H), 2.99-3.16 (m, 5H), 2.67-2.83 (m, 2H), 2.08-2.31 (m, 7H), 1.86-1.98 (m, 2H), 1.32-1.44 (m, 2H), 0.92 (s, 6H).

Example 26

4-(4-{[2-(4-chlorophenyl)-4,4-dimethylcyclohex-1-en-1-yl]methyl}piperazin-1-yl)-N-[(4-{[(4,4-difluoro-1-hydroxycyclohexyl)methyl]amino}-3-nitrophenyl)sulfonyl]-2-(1H-pyrrolo[2,3-b]pyridin-5-yloxy)benzamide Example 26A 4-(((4,4-difluoro-1-hydroxycyclohexyl)methyl)amino)-3-nitrobenzenesulfonamide The title compound was prepared by substituting 1-(aminomethyl)-4,4-difluorocyclohexanol for EXAMPLE 1M in EXAMPLE 1N.

Example 26B 4-(4-{[2-(4-chlorophenyl)-4,4-dimethylcyclohex-1-en-1-yl]methyl}piperazin-1-yl)-N-[(4-{[(4,4-difluoro-1-hydroxycyclohexyl)methyl]amino}-3-nitrophenyl)sulfonyl]-2-(1H-pyrrolo[2,3-b]pyridin-5-yloxy)benzamide The title compound was prepared by substituting EXAMPLE 26A for EXAMPLE 1N in EXAMPLE 1O. $^1H$ NMR (300 MHz, dimethylsulfoxide-$d_6$) δ ppm 11.73 (s, 1H), 11.40 (bs, 1H), 8.73 (t, 1H), 8.63 (d, 1H), 8.11 (d, 1H), 7.87 (dd, 1H), 7.62-7.53 (m, 3H), 7.40 (d, 2H), 7.25 (d, 1H), 7.10 (d, 2H), 6.74 (dd, 1H), 6.45 (dd, 1H), 6.25 (d, 1H), 5.12 (s, 1H), 3.49-3.42 (m, 2H), 3.13 (bs, 4H), 2.81 (bs, 2H), 2.30-2.18 (m, 6H), 2.15-1.90 (m, 6H), 1.81 (d, 2H), 1.66 (td, 2H), 1.44 (t, 2H), 0.98 (s, 6H).

Example 27

4-(4-{[2-(4-chlorophenyl)-4,4-dimethylcyclohex-1-en-1-yl]methyl}piperazin-1-yl)-N-[(4-{[(4-methoxytetrahydro-2H-pyran-4-yl)methyl]amino}-3-nitrophenyl)sulfonyl]-2-(1H-pyrrolo[2,3-b]pyridin-5-yloxy)benzamide Example 27A 4-(((4-methoxytetrahydro-2H-pyran-4-yl)methyl)amino)-3-nitrobenzenesulfonamide The title compound was prepared by substituting (4-methoxytetrahydro-2H-pyran-4-yl)methanamine for EXAMPLE 1M in EXAMPLE 1N.

Example 27B 4-(4-{[2-(4-chlorophenyl)-4,4-dimethylcyclohex-1-en-1-yl]methyl}piperazin-1-yl)-N-[(4-{[(4-methoxytetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting EXAMPLE 27A for EXAMPLE 1N in EXAMPLE 1O. $^1H$ NMR (300 MHz, dimethylsulfoxide-$d_6$) δ ppm 11.69 (s, 1H), 11.36 (bs, 1H), 8.58 (d, 1H), 8.42 (t, 1H), 8.05 (d, 1H), 7.87 (dd, 1H), 7.56-7.48 (m, 3H), 7.34 (d, 2H), 7.12 (d, 1H), 7.04 (d, 2H), 6.68 (d, 1H), 6.40 (dd, 1H), 6.19 (d, 1H), 3.68-3.62 (m, 2H), 3.56 (td, 2H), 3.47 (d, 2H), 3.17 (s, 3H), 3.07 (bs, 4H), 2.76 (bs, 2H), 2.20 (bs, 4H), 2.14 (t, 2H), 1.95 (bs, 2H), 1.75 (d, 2H), 1.60 (m, 2H), 1.38 (t, 2H), 0.92 (s, 6H).

Example 28

4-(4-{[2-(4-chlorophenyl)-4,4-dimethylcyclohex-1-en-1-yl]methyl}piperazin-1-yl)-N-[(4-{[(3,3-difluorocyclobutyl)methyl]amino}-3-nitrophenyl)sulfonyl]-2-(1H-pyrrolo[2,3-b]pyridin-5-yloxy)benzamide Example 28A 4-(((3,3-difluorocyclobutyl)methyl)amino)-3-nitrobenzenesulfonamide The title compound was prepared by substituting (3,3-difluorocyclobutyl)methanamine hydrochloride for EXAMPLE 1M in EXAMPLE 1N.

Example 28B 4-(4-{[2-(4-chlorophenyl)-4,4-dimethylcyclohex-1-en-1-yl]methyl}piperazin-1-yl)-N-[(4-{[(3,3-difluorocyclobutyl)methyl]amino}-3-nitrophenyl)sulfonyl]-2-(1H-pyrrolo[2,3-b]pyridin-5-yloxy)benzamide The title compound was prepared by substituting EXAMPLE 28A for EXAMPLE 1N in EXAMPLE 1O. $^1H$ NMR (300 MHz, dimethylsulfoxide-$d_6$) δ ppm 11.67 (s, 1H), 11.41 (bs, 1H), 8.62 (t, 1H), 8.56 (d, 1H), 8.04 (d, 1H), 7.80 (dd, 1H), 7.54-7.46 (m, 3H), 7.34 (d, 2H), 7.11 (d, 1H), 7.04 (d, 2H), 6.68 (d, 1H), 6.39 (dd, 1H), 6.20 (d, 1H), 3.53 (t, 2H), 3.07 (bs, 4H), 2.74 (bs, 2H), 2.70-2.59 (m, 2H), 2.46-2.35 (m, 2H), 2.25-2.10 (m, 7H), 1.95 (bs, 2H), 1.38 (t, 2H), 0.92 (s, 6H).

Example 29

4-(4-{[2-(4-chlorophenyl)-4,4-dimethylcyclohex-1-en-1-yl]methyl}piperazin-1-yl)-N-({3-nitro-4-[({1-[(trifluoromethyl)sulfonyl]piperidin-4-yl}methyl)amino]phenyl}sulfonyl)-2-(1H-pyrrolo[2,3-b]pyridin-5-yloxy)benzamide Example 29A 3-nitro-4-(((1-((trifluoromethyl)sulfonyl)piperidin-4-yl)methyl)amino)benzenesulfonamide The title compound was prepared by substituting (1-((trifluoromethyl)sulfonyl)piperidin-4-yl)methanamine for EXAMPLE 1M in EXAMPLE 1N.

Example 29B 4-(4-{[2-(4-chlorophenyl)-4,4-dimethylcyclohex-1-en-1-yl]methyl}piperazin-1-yl)-N-({3-nitro-4-[({1-[(trifluoromethyl)sulfonyl]piperidin-4-yl}methyl)amino]phenyl}sulfonyl)-2-(1H-pyrrolo[2,3-b]pyridin-5-yloxy)benzamide The title compound was prepared by substituting EXAMPLE 29A for EXAMPLE 1N in EXAMPLE 1O. $^1H$ NMR (300 MHz, dimethylsulfoxide-$d_6$) δ ppm 11.67 (s, 1H), 11.39 (bs, 1H), 8.63 (t, 1H), 8.56 (d, 1H), 8.04 (d, 1H), 7.81 (dd, 1H), 7.54-7.48 (m, 3H), 7.34 (d, 2H), 7.13 (d, 1H), 7.04 (d, 2H), 6.68 (d, 1H), 6.39 (dd, 1H), 6.19 (d, 1H), 3.82 (d, 2H), 3.36 (t, 2H), 3.17 (t, 2H), 3.07 (bs, 4H), 2.75 (bs, 2H), 2.25-2.11 (m, 6H), 1.95 (bs, 2H), 1.86 (m, 3H), 1.38 (t, 2H), 1.27 (m, 2H), 0.92 (s, 6H).

Example 30

4-(4-{[2-(4-chlorophenyl)-4,4-dimethylcyclohex-1-en-1-yl]methyl}piperazin-1-yl)-N-{[4-({[1-(methylsulfonyl)piperidin-4-yl]methyl}amino)-3-nitrophenyl]sulfonyl}-2-(1H-pyrrolo[2,3-b]pyridin-5-yloxy)benzamide Example 30A 4-(((1-(methylsulfonyl)piperidin-4-yl)methyl)amino)-3-nitrobenzenesulfonamide The title compound was prepared by substituting (1-(methylsulfonyl)piperidin-4-yl)methanamine for EXAMPLE 1M in EXAMPLE 1N.

Example 30B 4-(4-{[2-(4-chlorophenyl)-4,4-dimethylcyclohex-1-en-1-yl]methyl}piperazin-1-yl)-N-{[4-({[1-(methylsulfonyl)piperidin-4-yl]methyl}amino)-3-nitrophenyl]sulfonyl}-2-(1H-pyrrolo[2,3-b]pyridin-5-yloxy)benzamide The title compound was prepared by substituting EXAMPLE 30A for EXAMPLE 1N in EXAMPLE 1O. $^1H$ NMR (300 MHz, dimethylsulfoxide-$d_6$) δ ppm 11.67 (s, 1H), 11.40 (bs, 1H), 8.62 (t, 1H), 8.56 (d, 1H), 8.04 (d, 1H), 7.80 (dd, 1H), 7.54-7.48 (m, 3H), 7.34 (d, 2H), 7.12 (d, 1H), 7.04 (d, 2H), 6.68 (d, 1H), 6.39 (dd, 1H), 6.19 (d, 1H), 3.56 (d, 2H), 3.34 (t, 2H), 3.07 (bs, 4H), 2.83 (s, 3H), 2.75 (bs, 2H), 2.67 (td, 2H), 2.25-2.10 (m, 6H), 1.95 (bs, 2H), 1.81 (m, 3H), 1.38 (t, 2H), 1.27 (m, 2H), 0.92 (s, 6H).

Example 31

4-(4-{[2-(4-chlorophenyl)-4,4-dimethylcyclohex-1-en-1-yl]methyl}piperazin-1-yl)-N-{[4-({[(2R,4R,6S)-2,6-dimethyltetrahydro-2H-pyran-4-yl]methyl}amino)-3-nitrophenyl]sulfonyl}-2-(1H-pyrrolo[2,3-b]pyridin-5-yloxy)benzamide

Example 31A (2R,6S)-2,6-dimethyltetrahydro-4H-pyran-4-one 2,6-Dimethyl-4H-pyran-4-one (14 g) and tetrahydrofuran (140 mL) were added to 10% Pd/C, dry (2.8 g) in a 250 mL SS pressure bottle and the mixture was stirred for 2 hours at 50 psi. The mixture was filtered through a nylon membrane and concentrated. The crude product was chromatographed on silica gel with 5-50% ethyl acetate/hexanes to afford the title compound.

Example 31B rac-(2R,6S)-2,6-dimethyltetrahydro-2H-pyran-4-carbonitrile

The title compound was prepared by substituting EXAMPLE 31A for 1-oxaspiro[4.5]decan-8-one in EXAMPLE 4A

Example 31C 4-({[(2R,4R,6S)-2,6-dimethyltetrahydro-2H-pyran-4-yl]methyl}amino)-3-nitrobenzenesulfonamide $LiAlH_4$ (14.4 mL, 1M in tetrahydrofuran) was added to EXAMPLE 31B (2 g) in tetrahydrofuran (40 mL) and the mixture was stirred for 1 hour. The reaction mixture was quenched by the addition of saturated sodium potassium tartrate solution (5 mL), and the mixture was stirred for 30 minutes. The solution was decanted away from the salts and concentrated. The crude material was taken up in tetrahydrofuran (50 mL) and triethylamine (2.0 mL) and 4-fluoro-3-nitrobenzenesulfonamide (3.16 g) were added. The reaction mixture was stirred for 1 hour. The reaction mixture was diluted with ethyl acetate (200 mL), washed twice with $NaH_2PO_4$ solution and brine, and concentrated. The crude product was chromatographed on silica gel with 10-50% ethyl acetate/hexanes to separately afford the title compound and its diastereomer.

Example 31D 4-(4-{[2-(4-chlorophenyl)-4,4-dimethylcyclohex-1-en-1-yl]methyl}piperazin-1-yl)-N-{[4-({[(2R,4R,6S)-2,6-dimethyltetrahydro-2H-pyran-4-yl]methyl}amino)-3-nitrophenyl]sulfonyl}-2-(1H-pyrrolo[2,3-b]pyridin-5-yloxy)benzamide The title compound was prepared by substituting EXAMPLE 31C for EXAMPLE 1N in EXAMPLE 1O. $^1H$ NMR (300 MHz, dimethylsulfoxide-$d_6$) δ 11.69 (s, 1H), 11.40 (br s, 1H), 8.60 (m, 1H), 8.56 (s, 1H), 8.04 (s, 1H), 7.80 (d, 1H), 7.51 (m, 2H), 7.34 (d, 2H), 7.09 (d, 1H), 7.04 (d, 2H), 6.68 (d, 1H), 6.40 (d, 1H), 6.19 (s, 1H), 3.39 (m, 2H), 3.28 (m, 2H), 3.07 (m, 4H), 2.75 (s, 2H), 2.19 (s, 4H), 2.14 (m, 2H), 1.95 (s, 2H), 1.65 (m, 2H), 1.38 (m, 2H), 1.09 (s, 6H), 0.92 (m, 6H), 0.84 (m, 4H).

Example 32

4-(4-{[2-(4-chlorophenyl)-4,4-dimethylcyclohex-1-en-1-yl]methyl}piperazin-1-yl)-N-[(3-nitro-4-{[(1-oxidotetrahydro-2H-thiopyran-4-yl)methyl]amino}phenyl)sulfonyl]-2-(1H-pyrrolo[2,3-b]pyridin-5-yloxy)benzamide EXAMPLE 22B (450 mg) was dissolved in dichloromethane (8 mL), and 3-chloroperoxybenzoic acid (76%, 88 mg) was added. The reaction mixture was stirred at room temperature for three days. The crude material was purified by flash column chromatography on silica gel using 10-20% methanol in dichloromethane. $^1H$ NMR (300 MHz, dimethylsulfoxide-$d_6$) δ ppm 11.67 (s, 1H), 11.41 (bs, 1H), 8.68-8.56 (m, 1H), 8.55 (d, 1H), 8.03 (d, 1H), 7.78 (d, 1H), 7.52-7.47 (m, 3H), 7.34 (d, 2H), 7.09 (m, 1H), 7.04 (d, 2H), 6.67 (d, 1H), 6.39 (dd, 1H), 6.20 (d, 1H), 3.25 (m, 2H), 3.06 (bs, 4H), 2.86 (d, 2H), 2.73 (bs, 2H), 2.66-2.53 (m, 2H), 2.25-2.00 (m, 6H), 1.95 (bs, 2H), 1.87 (m, 3H), 1.69 (m, 2H), 1.38 (t, 2H), 0.92 (s, 6H).

Example 33

4-(4-{[2-(4-chlorophenyl)-4,4-dimethylcyclohex-1-en-1-yl]methyl}piperazin-1-yl)-N-{[4-({[(4S)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide

Example 33A (S)-4-(((2,2-dimethyltetrahydro-2H-pyran-4-yl)methyl)amino)-3-nitrobenzenesulfonamide The title compound was prepared by substituting racemic (2,2-dimethyltetrahydro-2H-pyran-4-yl)methanamine hydrochloride for EXAMPLE 1M in EXAMPLE 1N, and performing chiral purification as described in EXAMPLE 19D.

Example 33B 4-(4-{[2-(4-chlorophenyl)-4,4-dimethylcyclohex-1-en-1-yl]methyl}piperazin-1-yl)-N-{[4-({[(4S)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide The title compound was prepared by substituting EXAMPLE 33A for EXAMPLE 1N in EXAMPLE 1O. $^1H$ NMR (300 MHz, dimethylsulfoxide-$d_6$) δ ppm 11.67 (s, 1H), 11.41 (bs, 1H), 8.60-8.52 (m, 2H), 8.04 (d, 1H), 7.80 (dd, 1H), 7.53-7.47 (m, 3H), 7.34 (d, 2H), 7.10 (d, 1H), 7.04 (d, 2H), 6.68 (d, 1H), 6.39 (dd, 1H), 6.19 (d, 1H), 3.59 (td, 1H), 3.52 (td, 1H), 3.25 (t, 2H), 3.07 (bs, 4H), 2.74 (bs, 2H), 2.28-2.00 (m, 8H), 1.95 (bs, 2H), 1.58 (dd, 2H), 1.38 (t, 2H), 1.25 (m, 1H), 1.12 (s, 6H), 0.92 (s, 6H).

Example 34

4-(4-{[2-(4-chlorophenyl)-4,4-dimethylcyclohex-1-en-1-yl]methyl}piperazin-1-yl)-N-{[4-({[(4R)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide Example 34A (R)-4-(((2,2-dimethyltetrahydro-2H-pyran-4-yl)methyl)amino)-3-nitrobenzenesulfonamide The title compound was also prepared as described in EXAMPLE 33A.

Example 34B 4-(4-{[2-(4-chlorophenyl)-4,4-dimethylcyclohex-1-en-1-yl]methyl}piperazin-1-yl)-N-{[4-({[(4R)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide The title compound was prepared by substituting EXAMPLE 34A for EXAMPLE 1N in EXAMPLE 1O. $^1H$ NMR (300 MHz, dimethylsulfoxide-$d_6$) δ ppm 11.67 (s, 1H), 11.40 (bs, 1H), 8.60-8.52 (m, 2H), 8.04 (d, 1H), 7.80 (dd, 1H), 7.53-7.47 (m, 3H), 7.34 (d, 2H), 7.10 (d, 1H), 7.04 (d, 2H), 6.68 (d, 1H), 6.39 (dd, 1H), 6.19 (d, 1H), 3.59 (td, 1H), 3.52 (td, 1H), 3.25 (t, 2H), 3.07 (bs, 4H), 2.74 (bs, 2H), 2.28-2.00 (m, 8H), 1.95 (bs, 2H), 1.58 (dd, 2H), 1.38 (t, 2H), 1.25 (m, 1H), 1.12 (s, 6H), 0.92 (s, 6H).

Example 35

4-(4-{[2-(4-chlorophenyl)-4,4-dimethylcyclohex-1-en-1-yl]methyl}piperazin-1-yl)-N-{[4-({[(2S,6R)-6-methyl-1,4-dioxan-2-yl]methyl}amino)-3-nitrophenyl]sulfonyl}-2-(1H-pyrrolo[2,3-b]pyridin-5-yloxy)benzamide Example 35A (R)-1-(tert-butyldiphenylsilyloxy)propan-2-ol (R)-propane-1,2-diol (5 g) and imidazole (4.5 g) were dissolved in dichloromethane (200 mL). The mixture was cooled to 0° C., and a solution of tert-butylchlorodiphenylsilane (18.1 g) in dichloromethane (50 mL) was added dropwise. The reaction mixture was maintained at 0° C. under a drying tube overnight. The reaction mixture was filtered through diatomaceous earth, and concentrated. The crude material was chromatographed on silica gel with 9/1 heptanes/ethyl acetate to afford the title compound.

Example 35B (R)-(2-(benzyloxy)propoxy)(tert-butyl)diphenylsilane

EXAMPLE 35A (16.8 g), benzyl bromide (9.5 mL), N-ethyl-N-isopropylpropan-2-amine (15.0 mL), and sodium iodide (0.82 g) were heated at 150° C. under $N_2$ for 3 days. The reaction was cooled to room temperature and partitioned between ethyl acetate and 1M $KHSO_4$. The organic layer was washed with brine, and dried over $Na_2SO_4$. After filtration and concentration, the crude material was chromatographed on silica gel with 98.5/1.5 heptanes/ethyl acetate to afford the title compound.

Example 35C (R)-2-(benzyloxy)propan-1-ol

EXAMPLE 35B (5.6 g) was dissolved in tetrahydrofuran (50 mL), tetrabutyl ammonium fluoride (15 mL, 1.0M in 95/5 tetrahydrofuran/$H_2O$) was added and the reaction was stirred overnight. The reaction mixture was concentrated and the crude material was chromatographed on silica gel with 3/1 heptanes/ethyl acetate to afford the title compound.

Example 35D (R)-((1-(allyloxy)propan-2-yloxy)methyl)benzene

The title compound was prepared by substituting EXAMPLE 35C for (R)-1-(benzyloxy)propan-2-ol in EXAMPLE 24A.

Example 35E 2-(((R)-2-(benzyloxy)propoxy)methyl)oxirane

The title compound was prepared by substituting EXAMPLE 35D for EXAMPLE 24A in EXAMPLE 24B.

Example 35F (R)-2-(((R)-2-(benzyloxy)propoxy)methyl)oxirane

The title compound was prepared by substituting EXAMPLE 35E for EXAMPLE 24B and S,S-(salen)Co(II) complex (CAS#188264-84-8) for R,R-(salen)Co(II) complex in EXAMPLE 24C.

Example 35G (R)-1-((R)-oxiran-2-ylmethoxy)propan-2-ol

EXAMPLE 35F (780 mg) was dissolved in tetrahydrofuran (20 mL), and $Pd(OH)_2$ on carbon (20% Pd dry wt/overall 50% water, 80 mg) was added. The reaction mixture was stirred under a hydrogen balloon for 3 hours. Filtration through diatomaceous earth and concentration gave the title compound that was used in the next step without further purification.

Example 35H ((2S,6R)-6-methyl-1,4-dioxan-2-yl)methanol

The title compound was prepared by substituting EXAMPLE 35G for EXAMPLE 24D in EXAMPLE 24E.

Example 35I ((2R,6R)-6-methyl-1,4-dioxan-2-yl)methyl methanesulfonate

The title compound was prepared by substituting EXAMPLE 35H for EXAMPLE 24E in EXAMPLE 24F.

Example 35J (2S,6R)-2-(azidomethyl)-6-methyl-1,4-dioxane

The title compound was prepared by substituting EXAMPLE 35I for EXAMPLE 1K in EXAMPLE 1L.

Example 35K ((2S,6R)-6-methyl-1,4-dioxan-2-yl)methanamine

The title compound was prepared by substituting EXAMPLE 35J for EXAMPLE 9B in EXAMPLE 9C.

Example 35L 4-(((2S,6R)-6-methyl-1,4-dioxan-2-yl)methylamino)-3-nitrobenzenesulfonamide The title compound was prepared by substituting EXAMPLE 35J for EXAMPLE 1M in EXAMPLE 1N.

Example 35M 4-(4-{[2-(4-chlorophenyl)-4,4-dimethylcyclohex-1-en-1-yl]methyl}piperazin-1-yl)-N-{[4-({[(2S,6R)-6-methyl-1,4-dioxan-2-yl]methyl}amino)-3-nitrophenyl]sulfonyl}-2-(1H-pyrrolo[2,3-b]pyridin-5-yloxy)benzamide The title compound was prepared by substituting EXAMPLE 35L for EXAMPLE 1N in EXAMPLE 1O. $^1H$ NMR (400 MHz, dimethylsulfoxide-$d_6$) δ ppm 11.66 (s, 1H), 11.35 (v br s, 1H), 8.59 (t, 1H), 8.55 (d, 1H), 8.03 (d, 1H), 7.81 (dd, 1H), 7.50 (m, 3H), 7.34 (d, 2H), 7.08 (d, 1H), 7.03 (d, 2H), 6.68 (dd, 1H), 6.38 (m, 1H), 6.20 (d, 1H), 3.86 (m, 1H), 3.79 (dd, 1H), 3.70 (m, 2H), 3.48 (m, 1H), 3.35 (m, 2H), 3.21 (t, 1H), 3.06 (br m, 5H), 2.76 (br s, 2H), 2.20 (br m, 4H), 2.14 (br m, 2H), 1.95 (br m, 2H), 1.38 (t, 2H), 1.01 (d, 3H), 0.92 (s, 6H).

Example 36

4-(4-{[2-(4-chlorophenyl)-4,4-dimethylcyclohex-1-en-1-yl]methyl}piperazin-1-yl)-N-[(3-nitro-4-{[(3S)-tetrahydrofuran-3-ylmethyl]amino}phenyl)sulfonyl]-2-(1H-pyrrolo[2,3-b]pyridin-5-yloxy)benzamide Example 36A (S)-(tetrahydrofuran-3-yl)methanol (R)-tetrahydrofuran-3-carboxylic acid (0.50 g) in tetrahydrofuran (7.5 mL) was cooled to 0° C., and borane tetrahydrofuran complex (14 mL 1.0M in tetrahydrofuran) was added dropwise, keeping the temperature <6° C. The reaction mixture was allowed to stir at room temperature under nitrogen for 45 minutes. The reaction mixture was cooled to 0° C. and 5N NaOH (2.3 mL) was carefully added. The reaction mixture was stirred for a few minutes, and water and diethylether were added. The separated organic layer was washed with brine and the combined aqueous layers were back-extracted with diethylether. The combined organic layers were dried over $Na_2SO_4$, filtered, and concentrated. The crude material was chromatographed on silica gel with 3/7 heptanes/ethyl acetate to afford the title compound.

Example 36B (R)-(tetrahydrofuran-3-yl)methyl methanesulfonate

The title compound was prepared by substituting EXAMPLE 36A for EXAMPLE 24E in EXAMPLE 24F.

Example 36C (S)-3-(azidomethyl)tetrahydrofuran

The title compound was prepared by substituting EXAMPLE 36B for EXAMPLE 1K in EXAMPLE 1L.

Example 36D (S)-(tetrahydrofuran-3-yl)methanamine

The title compound was prepared by substituting EXAMPLE 36C for EXAMPLE 9B in EXAMPLE 9C.

Example 36E (S)-3-nitro-4-((tetrahydrofuran-3-yl)methylamino)benzenesulfonamide

The title compound was prepared by substituting EXAMPLE 36D for EXAMPLE 1M in EXAMPLE 1N.

Example 36F 4-(4-{[2-(4-chlorophenyl)-4,4-dimethylcyclohex-1-en-1-yl]methyl}piperazin-1-yl)-N-[(3-nitro-4-{[(3S)-tetrahydrofuran-3-ylmethyl]amino}phenyl)sulfonyl]-2-(1H-pyrrolo[2,3-b]pyridin-5-yloxy)benzamide The title compound was prepared by substituting EXAMPLE 36E for EXAMPLE 1N in EXAMPLE 1O. $^1H$ NMR (400 MHz, dimethylsulfoxide-$d_6$) δ ppm 11.68 (s, 1H), 11.33 (v br s, 1H), 8.62 (t, 1H), 8.57 (d, 1H), 8.03 (d, 1H), 7.81 (dd, 1H), 7.50 (m, 3H), 7.34 (d, 2H), 7.09 (d, 1H), 7.03 (d, 2H), 6.68 (dd, 1H), 6.39 (m, 1H), 6.19 (d, 1H), 3.80 (m, 1H), 3.71 (dd, 1H), 3.63 (dd, 1H), 3.52 (m, 2H), 3.08 (br m, 4H), 2.76 (br s, 2H), 2.58 (m, 1H), 2.20 (br m, 4H), 2.00 (m, 1H), 2.14 (br m, 2H), 1.65 (m, 1H), 1.95 (br m, 2H), 1.38 (t, 2H), 0.92 (s, 6H).

Example 37

4-(4-{[2-(4-chlorophenyl)-4,4-dimethylcyclohex-1-en-1-yl]methyl}piperazin-1-yl)-N-{[4-({[(2S)-6,6-dimethyl-1,4-dioxan-2-yl]methyl}amino)-3-nitrophenyl]sulfonyl}-2-(1H-pyrrolo[2,3-b]pyridin-5-yloxy)benzamide Example 37A methyl 2-(allyloxy)acetate Methyl glycolate (25 g) was added dropwise over 10-15 minutes to a 0° C. suspension of NaH (7.7 g, 95%) in DMF (280 mL). Methyl glycolate (25 g) was then added dropwise over 10-15 minutes. The reaction was allowed to warm to room temperature, stirred for 1 hour, and cooled back down to 0° C. Allyl bromide (36.7 g) was added dropwise over 10-15 minutes, and the reaction was stirred at room temperature for 1 hour. The reaction mixture was poured into saturated aqueous $NH_4Cl$ solution (700 mL) and extracted with ethyl acetate (3×350 mL). The combined organic layers were washed with brine and dried over $Na_2SO_4$. After filtration and concentration, the crude product was distilled using a Vigeraux head and vac=3.4 mmHg to get the title compound as a mixture with DMF. This was dissolved in ether (10 mL), washed with water (2×10 mL) and brine, then dried over $MgSO_4$. Filtration and concentration gave the title compound.

Example 37B 1-(allyloxy)-2-methylpropan-2-ol

EXAMPLE 37A (12 g) was dissolved in tetrahydrofuran (200 mL) and cooled to 0° C. $CH_3MgCl$ (100 mL, 3.0 M in tetrahydrofuran) was added dropwise. The reaction mixture was stirred cold under $N_2$ for 3.5 hours. Saturated $NH_4Cl$ (60 mL) was slowly added followed by the addition of water and diethylether. The organic layer was washed with brine and dried over $Na_2SO_4$. Filtration and concentration of the filtrate afforded the title compound which was used in the next step without further purification.

Example 37C ((1-(allyloxy)-2-methylpropan-2-yloxy)methyl)benzene

The title compound was prepared by substituting EXAMPLE 37B for EXAMPLE 35A in EXAMPLE 35B.

Example 37D 2-((2-(benzyloxy)-2-methylpropoxy)methyl)oxirane

The title compound was prepared by substituting EXAMPLE 37C for EXAMPLE 24A in EXAMPLE 24B.

Example 37E (R)-2-((2-(benzyloxy)-2-methylpropoxy)methyl)oxirane

The title compound was prepared by substituting EXAMPLE 37D for EXAMPLE 24B and S,S-(salen)Co(II) complex (CAS#188264-84-8) for R,R-(salen)Co(II) complex in EXAMPLE 24C.

Example 37F (R)-2-methyl-1-(oxiran-2-ylmethoxy)propan-2-ol

The title compound was prepared by substituting EXAMPLE 37E for EXAMPLE 35F in EXAMPLE 35G.

Example 37G (S)-(6,6-dimethyl-1,4-dioxan-2-yl)methanol

The title compound was prepared by substituting EXAMPLE 37F for EXAMPLE 24D in EXAMPLE 24E.

Example 37H (R)-(6,6-dimethyl-1,4-dioxan-2-yl)methyl methanesulfonate

The title compound was prepared by substituting EXAMPLE 37G for EXAMPLE 24E in EXAMPLE 24F.

Example 37I (S)-6-(azidomethyl)-2,2-dimethyl-1,4-dioxane

The title compound was prepared by substituting EXAMPLE 37H for EXAMPLE 1K in EXAMPLE 1L.

Example 37J (S)-(6,6-dimethyl-1,4-dioxan-2-yl)methanamine

The title compound was prepared by substituting EXAMPLE 37I for EXAMPLE 9B in EXAMPLE 9C.

Example 37K (S)-4-((6,6-dimethyl-1,4-dioxan-2-yl)methylamino)-3-nitrobenzenesulfonamide The title compound was prepared by substituting EXAMPLE 37J for EXAMPLE 1M in EXAMPLE 1N.

Example 37L 4-(4-{[2-(4-chlorophenyl)-4,4-dimethylcyclohex-1-en-1-yl]methyl}piperazin-1-yl)-N-{[4-({[(2S)-6,6-dimethyl-1,4-dioxan-2-yl]methyl}amino)-3-nitrophenyl]sulfonyl}-2-(1H-pyrrolo[2,3-b]pyridin-5-yloxy)benzamide The title compound was prepared by substituting EXAMPLE 37K for EXAMPLE 1N in EXAMPLE 1O. $^1H$ NMR (400 MHz, dimethylsulfoxide-$d_6$) δ ppm 11.66 (s, 1H), 11.33 (v br s, 1H), 8.57 (t, 1H), 8.56 (d, 1H), 8.03 (d, 1H), 7.82 (dd, 1H), 7.50 (m, 3H), 7.34 (d, 2H), 7.06 (d, 1H), 7.03 (d, 2H), 6.69 (dd, 1H), 6.38 (m, 1H), 6.20 (d, 1H), 4.06 (m, 1H), 3.81 (dd, 1H), 3.49 (d, 1H), 3.43 (m, 1H), 3.29 (m, 1H), 3.18 (m, 2H), 3.08 (br m, 4H), 2.76 (br s, 2H), 2.20 (br m, 4H), 2.14 (br m, 2H), 1.95 (br m, 2H), 1.38 (t, 2H), 1.27 (s, 3H), 1.08 (s, 3H), 0.92 (s, 6H).

Example 38

4-(4-{[2-(4-chlorophenyl)-4,4-dimethylcyclohex-1-en-1-yl]methyl}piperazin-1-yl)-N-[(4-{[(3-methyloxetan-3-yl)methyl]amino}-3-nitrophenyl)sulfonyl]-2-(1H-pyrrolo[2,3-b]pyridin-5-yloxy)benzamide Example 38A 4-(((3-methyloxetan-3-yl)methyl)amino)-3-nitrobenzenesulfonamide The title compound was prepared by substituting (3-methyloxetan-3-yl)methanamine for EXAMPLE 1M in EXAMPLE 1N.

Example 38B 4-(4-{[2-(4-chlorophenyl)-4,4-dimethylcyclohex-1-en-1-yl]methyl}piperazin-1-yl)-N-[(4-{[(3-methyloxetan-3-yl)methyl]amino}-3-nitrophenyl)sulfonyl]-2-(1H-pyrrolo[2,3-b]pyridin-5-yloxy)benzamide The title compound was prepared by substituting EXAMPLE 38A for EXAMPLE 1N in EXAMPLE 1O. $^1H$ NMR (300 MHz, dimethylsulfoxide-$d_6$) δ ppm 11.66 (s, 1H), 11.41 (bs, 1H), 8.67 (t, 1H), 8.57 (d, 1H), 8.03 (d, 1H), 7.83 (dd, 1H), 7.52-7.47 (m, 3H), 7.34 (d, 2H), 7.17 (d, 1H), 7.04 (d, 2H), 6.68 (d, 1H), 6.38 (dd, 1H), 6.20 (d, 1H), 4.45 (d, 2H), 4.31 (d, 2H), 3.57 (td, 2H), 3.07 (bs, 4H), 2.75 (bs, 2H), 2.25-2.11 (m, 6H), 1.95 (bs, 2H), 1.38 (t, 2H), 1.32 (s, 3H), 0.92 (s, 6H).

Example 39

4-(4-{[2-(4-chlorophenyl)-4,4-dimethylcyclohex-1-en-1-yl]methyl}piperazin-1-yl)-N-[(4-{[(6-fluoro-1,4-dioxepan-6-yl)methyl]amino}-3-nitrophenyl)sulfonyl]-2-(1H-pyrrolo[2,3-b]pyridin-5-yloxy)benzamide Example 39A 6-((dibenzylamino)methyl)-1,4-dioxepan-6-ol To a solution of EXAMPLE 25C (1.8 g) in dichloromethane (30 mL) was added benzaldehyde (3.82 g) and acetic acid (0.5 mL) followed by sodium cycanoborohydride on resin (2.4 mmol/g, 4.5 g). The mixture was stirred overnight. The mixture was then filtered and the filtrate was concentrated under vacuum. The residue was loaded on a silica gel column and eluted with 30% ethyl acetate in hexane to afford the title compound.

Example 39B

N,N-dibenzyl-1-(6-fluoro-1,4-dioxepan-6-yl)methanamine

To a solution of EXAMPLE 39A (256 mg) in dichloromethane (33 mL) was added bis(2-methoxyethyl)aminosulfur trifluoride (2 mL, 1M solution in tetrahydrofuran). The mixture was stirred overnight. The mixture was then poured into ice-water and extracted three times with dichloromethane (50 mL). The combined organic extracts were washed with aqueous $NaHCO_3$, water and brine, and dried over $Na_2SO_4$. After filtration and concentration, the crude material was purified by column chromatography using 20% ethyl acetate in heptane to afford the title compound.

Example 39C (6-fluoro-1,4-dioxepan-6-yl)methanamine

To a solution of EXAMPLE 39B (200 mg) in methanol (20 mL) was added Raney Ni (30 mg). The mixture was stirred under 30 psi hydrogen overnight. Filtration and concentration afforded the title compound.

Example 39D 4-(((6-fluoro-1,4-dioxepan-6-yl)methyl)amino)-3-nitrobenzenesulfonamide The title compound was prepared by substituting EXAMPLE 39C for EXAMPLE 1M in EXAMPLE 1N.

Example 39E 4-(4-{[2-(4-chlorophenyl)-4,4-dimethylcyclohex-1-en-1-yl]methyl}piperazin-1-yl)-N-[(4-{[(6-fluoro-1,4-dioxepan-6-yl)methyl]amino}-3-nitrophenyl)sulfonyl]-2-(1H-pyrrolo[2,3-b]pyridin-5-yloxy)benzamide The title compound was prepared by substituting EXAMPLE 39D for EXAMPLE 1N in EXAMPLE 1O. $^1H$ NMR (300 MHz dimethylsulfoxide-$d_6$) δ ppm 11.70 (s, 1H), 11.60-11.67 (m, 1H), 9.48-9.71 (m, 1H), 8.52-8.70 (m, 2H), 8.04 (d, 1H), 7.83 (dd, 1H), 7.46-7.62 (m, 3H), 7.39 (d, 2H), 7.20 (d, 1H), 7.08 (d, 2H), 6.71 (dd, 1H), 6.40 (dd, 1H), 6.25 (s, 1H), 3.49-4.03 (m, 9H), 2.99-3.19 (m, 2H), 2.62-2.84 (m, 2H), 2.15-2.31 (m, 4H), 1.97-2.05 (m, 4H), 1.37-1.53 (m, 4H), 0.94 (s, 6H).

Example 40

4-(4-{[2-(4-chlorophenyl)-4,4-dimethylcyclohex-1-en-1-yl]methyl}piperazin-1-yl)-N-[(4-{[(6-methoxy-1,4-dioxepan-6-yl)methyl]amino}-3-nitrophenyl)sulfonyl]-2-(1H-pyrrolo[2,3-b]pyridin-5-yloxy)benzamide Example 40A N,N-dibenzyl-1-(6-methoxy-1,4-dioxepan-6-yl)methanamine To a solution of EXAMPLE 39A (300 mg) in tetrahydrofuran (3 mL) and HMPA (hexamethylphosphoramide, 3 mL) was added NaH (200 mg, 60% in mineral oil). The mixture was stirred for 30 minutes before the addition of $CH_3I$ (0.6 g). The mixture was then stirred at 50° C. overnight. The mixture was poured over aqueous $NH_4Cl$ and extracted three times with ethyl acetate (100 mL). The combined organic extracts were washed three times with water, and brine, and dried over $Na_2SO_4$. After filtration and concentration, evaporation of the solvent gave crude product which was loaded on a silica gel column and eluted with 20% ethyl acetate in hexane to afford the title compound.

Example 40B (6-methoxy-1,4-dioxepan-6-yl)methanamine

To a solution of EXAMPLE 40A (200 mg) in methanol (20 mL) was added Raney Ni (50 mg). The mixture was stirred under 30 psi hydrogen overnight. After filtration, vacuum evaporation of the solvent afforded the title compound.

Example 40C 4-(((6-methoxy-1,4-dioxepan-6-yl)methyl)amino)-3-nitrobenzenesulfonamide The title compound was prepared by substituting EXAMPLE 40B for EXAMPLE 1M in EXAMPLE 1N.

Example 40D 4-(4-{[2-(4-chlorophenyl)-4,4-dimethylcyclohex-1-en-1-yl]methyl}piperazin-1-yl)-N-[(4-{[(6-methoxy-1,4-dioxepan-6-yl)methyl]amino}-3-nitrophenyl)sulfonyl]-2-(1H-pyrrolo[2,3-b]pyridin-5-yloxy)benzamide The title compound was prepared by substituting EXAMPLE 40C for EXAMPLE 1N in EXAMPLE 1O. $^1H$ NMR (300 MHz, dimethylsulfoxide-$d_6$) δ ppm 11.68 (s, 1H), 8.57 (d, 1H), 8.49 (t, 1H), 8.05 (d, 1H), 7.43-7.58 (m, 3H), 7.34 (d, 2H), 7.12 (d, 1H), 7.04 (d, 2H), 6.68 (dd, 1H), 6.39 (dd, 1H), 6.19 (d, 1H), 3.87-4.09 (m, 3H), 3.61-3.81 (m, 5H), 3.38-3.51 (m, 2H), 2.99-3.15 (m, 4H), 2.70-2.90 (m, 2H), 2.08-2.33 (m, 5H), 1.90-2.01 (m, 3H), 1.39 (t, 2H), 1.17 (t, 2H), 0.92 (s, 6H).

Example 41

4-(4-{[2-(4-chlorophenyl)-4,4-dimethylcyclohex-1-en-1-yl]methyl}piperazin-1-yl)-N-[(4-{[(trans-3-cyanocyclobutyl)methyl]amino}-3-nitrophenyl)sulfonyl]-2-(1H-pyrrolo[2,3-b]pyridin-5-yloxy)benzamide Example 41A trans-3-(hydroxymethyl)cyclobutanecarbonitrile Catecholborane (7.1 mL) was added to 3-methylenecyclobutanecarbonitrile (5.6 g) in tetrahydrofuran (25 mL) and the mixture was stirred for 24 hours. The reaction mixture was quenched by the slow addition of ethanol (25 mL), and the mixture was poured into ethanol (75 mL) and tetrahydrofuran (100 mL). To this was added 2M aqueous NaOH (150 mL) and 30% aqueous $H_2O_2$ (150 mL) was added slowly over 1 hour. The mixture was stirred another 3 hours, and was diluted with ethyl acetate (500 mL). The layers were separated and the organic layer was washed twice with 1M aqueous NaOH and brine, and concentrated. The crude product was chromatographed on silica gel with 5-100% ethyl acetate/hexanes to separately afford the title compound and its cis-diastereomer.

Example 41B trans-3-cyanocyclobutyl)methyl methanesulfonate

Mesyl chloride (1.0 mL) was added to EXAMPLE 41A (1.35 g) and diisopropylethylamine (2.33 mL) in dichloromethane (50 mL) at −20° C. The mixture was stirred for 1 hour. The reaction mixture was poured into dichloromethane (200 mL) and washed twice with water and brine, and concentrated. The crude product was chromatographed on silica gel with 10-100% ethyl acetate/hexanes to separately afford the title compound.

Example 41C 4-(((trans-3-cyanocyclobutyl)methyl)amino)-3-nitrobenzenesulfonamide Sodium azide (1.1 g) was added to EXAMPLE 41B (5.6 g) in N,N-dimethylformamide (15 mL) and the mixture was stirred for 24 hours. The reaction mixture was poured into water (75 mL) and extracted twice with ether (100 mL). The organic layers were combined and concentrated to 10 mL. Tetrahydrofuran (25 mL) was added and to the resulting mixture triphenylphosphine (2.2 g) and water (0.3 mL) were added, and the reaction was stirred for 24 hours. Sodium sulfate (5 g) and 4-fluoro-3-nitrobenzenesulfonamide (1.86 g) were added and the reaction was stirred for 2 hours at 40° C. The mixture was diluted with ethyl acetate (300 mL). The layers were separated and the organic layer was washed with brine, and concentrated. The crude product was chromatographed on silica gel with 50% ethyl acetate/hexanes to afford the title compound.

Example 41D 4-(4-{[2-(4-chlorophenyl)-4,4-dimethylcyclohex-1-en-1-yl]methyl}piperazin-1-yl)-N-[(4-{[(trans-3-cyanocyclobutyl)methyl]amino}-3-nitrophenyl)sulfonyl]-2-(1H-pyrrolo[2,3-b]pyridin-5-yloxy)benzamide The title compound was prepared by substituting EXAMPLE 41C for EXAMPLE 1N in EXAMPLE 1O. $^1H$ NMR (300 MHz, dimethylsulfoxide-$d_6$) δ 11.67 (s, 1H), 11.35 (br s, 1H), 8.56 (m, 1H), 8.54 (s, 1H), 8.04 (s, 1H), 7.80 (d, 1H), 7.51 (m, 2H), 7.34 (d, 2H), 7.09 (d, 1H), 7.04 (d, 2H), 6.69 (d, 1H), 6.39 (d, 1H), 6.19 (s, 1H), 3.51 (m, 2H), 3.40 (m, 1H), 3.07 (m, 4H), 2.78 (m, 1H), 2.75 (m, 2H), 2.38 (m, 2H), 2.20 (m, 6H), 1.95 (s, 2H), 1.38 (t, 2H), 1.24 (m, 1H), 0.92 (m, 6H), 0.85 (m, 2H).

Example 42

4-(4-{[2-(4-chlorophenyl)-4,4-dimethylcyclohex-1-en-1-yl]methyl}piperazin-1-yl)-N-[(4-{[(cis-3-cyanocyclobutyl)methyl]amino}-3-nitrophenyl)sulfonyl]-2-(1H-pyrrolo[2,3-b]pyridin-5-yloxy)benzamide Example 42A cis-3-(hydroxymethyl)cyclobutanecarbonitrile The title compound was also isolated from EXAMPLE 41A.

Example 42B cis-3-cyanocyclobutyl)methyl methanesulfonate

The title compound was prepared by substituting EXAMPLE 42A for EXAMPLE 41A in EXAMPLE 41B.

Example 42C 4-(((cis-3-cyanocyclobutyl)methyl)amino)-3-nitrobenzenesulfonamide

The title compound was prepared by substituting EXAMPLE 42B for EXAMPLE 41B in EXAMPLE 41C.

Example 42D 4-(4-{[2-(4-chlorophenyl)-4,4-dimethylcyclohex-1-en-1-yl]methyl}piperazin-1-yl)-N-[(4-{[(cis-3-cyanocyclobutyl)methyl]amino}-3-nitrophenyl)sulfonyl]-2-(1H-pyrrolo[2,3-b]pyridin-5-yloxy)benzamide The title compound was prepared by substituting EXAMPLE 42C for EXAMPLE 1N in EXAMPLE 1O. $^1H$ NMR (300 MHz, dimethylsulfoxide-$d_6$) δ 11.68 (s, 1H), 11.35 (br s, 1H), 8.55 (m, 2H), 8.04 (s, 1H), 7.81 (d, 1H), 7.51 (m, 2H), 7.34 (d, 2H), 7.06 (d, 1H), 7.04 (d, 2H), 6.69 (d, 1H), 6.39 (d, 1H), 6.19 (s, 1H), 3.47 (m, 2H), 3.32 (m, 1H), 3.07 (m, 4H), 2.75 (m, 2H), 2.65 (m, 1H), 2.38 (m, 2H), 2.20 (m, 6H), 1.95 (s, 2H), 1.38 (t, 2H), 1.24 (m, 1H), 0.92 (m, 6H), 0.86 (m, 2H).

Example 43

4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-pyrrolo[2,3-b]pyridin-5-yloxy)benzamide Example 43A 4-(((1,1-dioxidotetrahydro-2H-thiopyran-4-yl)methyl)amino)-3-nitrobenzenesulfonamide The title compound was prepared by substituting 4-(aminomethyl)tetrahydro-2H-thiopyran 1,1-dioxide hydrochloride for EXAMPLE 1M in EXAMPLE 1N.

Example 43B 4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-pyrrolo[2,3-b]pyridin-5-yloxy)benzamide The title compound was prepared by substituting EXAMPLE 43A for EXAMPLE 1N in EXAMPLE 1O. $^1H$ NMR (300 MHz, dimethylsulfoxide-$d_6$) δ ppm 11.67 (s, 1H), 11.42 (bs, 1H), 8.66 (t, 1H), 8.56 (d, 1H), 8.04 (d, 1H), 7.81 (dd, 1H), 7.56-7.48 (m, 3H), 7.34 (d, 2H), 7.13 (d, 1H), 7.04 (d, 2H), 6.68 (d, 1H), 6.39 (dd, 1H), 6.19 (d, 1H), 3.37 (t, 2H), 3.17-3.00 (m, 8H), 2.73 (bs, 2H), 2.26-2.03 (m, 9H), 1.95 (bs, 2H), 1.68 (m, 2H), 1.38 (t, 2H), 0.92 (s, 6H).

Example 44

4-(4-{[2-(4-chlorophenyl)-4,4-dimethylcyclohex-1-en-1-yl]methyl}piperazin-1-yl)-N-{[4-({[(2S,5R)-5-methyl-1,4-dioxan-2-yl]methyl}amino)-3-nitrophenyl]sulfonyl}-2-(1H-pyrrolo[2,3-b]pyridin-5-yloxy)benzamide Example 44A (R)-2-(((R)-1-(benzyloxy)propan-2-yloxy)methyl)oxirane The title compound was prepared by substituting S,S-(salen)Co(II) complex (CAS#188264-84-8) for R,R-(salen)Co(II) complex (CAS#176763-62-5) in EXAMPLE 24C.

Example 44B (R)-2-((R)-oxiran-2-ylmethoxy)propan-1-ol

The title compound was prepared by substituting EXAMPLE 44A for EXAMPLE 35F in EXAMPLE 35G.

Example 44C ((2S,5R)-5-methyl-1,4-dioxan-2-yl)methanol

The title compound was prepared by substituting EXAMPLE 44B for EXAMPLE 24D in EXAMPLE 24E.

Example 44D ((2R,5R)-5-methyl-1,4-dioxan-2-yl)methyl methanesulfonate

The title compound was prepared by substituting EXAMPLE 44C for EXAMPLE 24E in EXAMPLE 24F.

Example 44E (2S,5R)-2-(azidomethyl)-5-methyl-1,4-dioxane

The title compound was prepared by substituting EXAMPLE 44D for EXAMPLE 1K in EXAMPLE 1L.

Example 44F ((2S,5R)-5-methyl-1,4-dioxan-2-yl)methanamine

The title compound was prepared by substituting EXAMPLE 44E for EXAMPLE 9B in EXAMPLE 9C.

Example 44G 4-(((2S,5R)-5-methyl-1,4-dioxan-2-yl)methylamino)-3-nitrobenzenesulfonamide The title compound was prepared by substituting EXAMPLE 44F for EXAMPLE 1M in EXAMPLE 1N.

Example 44H 4-(4-{[2-(4-chlorophenyl)-4,4-dimethylcyclohex-1-en-1-yl]methyl}piperazin-1-yl)-N-{[4-({[(2S,5R)-5-methyl-1,4-dioxan-2-yl]methyl}amino)-3-nitrophenyl]sulfonyl}-2-(1H-pyrrolo[2,3-b]pyridin-5-yloxy)benzamide The title compound was prepared by substituting EXAMPLE 44G for EXAMPLE 1N in EXAMPLE 1O. $^1H$ NMR (400 MHz, dimethylsulfoxide-$d_6$) δ 11.66 (s, 1H), 8.57 (t, 1H), 8.55 (d, 1H), 8.03 (d, 1H), 7.83 (dd, 1H), 7.50 (m, 3H), 7.34 (d, 2H), 7.10 (d, 1H), 7.03 (d, 2H), 6.67 (dd, 1H), 6.38 (m, 1H), 6.19 (d, 1H), 3.81 (ddd, 2H), 3.72 (m, 1H), 3.52 (m, 2H), 3.36 (m, 2H), 3.20 (dd, 1H), 3.07 (br m, 4H), 2.76 (br s, 2H), 2.20 (br m, 4H), 2.14 (br m, 2H), 1.95 (br m, 2H), 1.38 (t, 2H), 0.98 (d, 3H), 0.92 (s, 6H).

Example 45

4-(4-{[2-(4-chlorophenyl)-4,4-dimethylcyclohex-1-en-1-yl]methyl}piperazin-1-yl)-N-{[4-({[(2S,5S)-5-methyl-1,4-dioxan-2-yl]methyl}amino)-3-nitrophenyl]sulfonyl}-2-(1H-pyrrolo[2,3-b]pyridin-5-yloxy)benzamide Example 45A (S)-((2-(allyloxy)propoxy)methyl)benzene The title compound was prepared by substituting (S)-1-(benzyloxy)propan-2-ol for (R)-1-(benzyloxy)propan-2-ol in EXAMPLE 24A.

Example 45B (S)-2-((R)-oxiran-2-ylmethoxy)propan-1-ol

The title compound was prepared by substituting EXAMPLE 45A for EXAMPLE 24A in EXAMPLE 24B.

Example 45C (R)-2-(((S)-1-(benzyloxy)propan-2-yloxy)methyl)oxirane

The title compound was prepared by substituting S,S-(salen)Co(II) complex (CAS#188264-84-8) for R,R-(salen)Co(II) complex (CAS#176763-62-5) and EXAMPLE 45B for EXAMPLE 24B in EXAMPLE 24C.

Example 45D (S)-2-((S)-oxiran-2-ylmethoxy)propan-1-ol

The title compound was prepared by substituting EXAMPLE 45C for EXAMPLE 35F in EXAMPLE 35G.

Example 45E ((2S,5S)-5-methyl-1,4-dioxan-2-yl)methanol

The title compound was prepared by substituting EXAMPLE 45D for EXAMPLE 24D in EXAMPLE 24E.

Example 45F ((2R,5S)-5-methyl-1,4-dioxan-2-yl)methyl methanesulfonate

The title compound was prepared by substituting EXAMPLE 45E for EXAMPLE 24E in EXAMPLE 24F.

Example 45G (2S,5S)-2-(azidomethyl)-5-methyl-1,4-dioxane

The title compound was prepared by substituting EXAMPLE 45F for EXAMPLE 1K in EXAMPLE 1L.

Example 45H ((2S,5S)-5-methyl-1,4-dioxan-2-yl)methanamine

The title compound was prepared by substituting EXAMPLE 45G for EXAMPLE 9B in EXAMPLE 9C.

Example 45I 4-(((2S,5S)-5-methyl-1,4-dioxan-2-yl)methylamino)-3-nitrobenzenesulfonamide The title compound was prepared by substituting EXAMPLE 45H for EXAMPLE 1M in EXAMPLE 1N.

Example 45J 4-(4-{[2-(4-chlorophenyl)-4,4-dimethylcyclohex-1-en-1-yl]methyl}piperazin-1-yl)-N-{[4-({[(2S,5S)-5-methyl-1,4-dioxan-2-yl]methyl}amino)-3-nitrophenyl]sulfonyl}-2-(1H-pyrrolo[2,3-b]pyridin-5-yloxy)benzamide The title compound was prepared by substituting EXAMPLE 45I for EXAMPLE 1N in EXAMPLE 1O. $^1H$ NMR (400 MHz, dimethylsulfoxide-$d_6$) δ 11.67 (s, 1H), 8.57 (d, 1H), 8.55 (t, 1H), 8.03 (d, 1H), 7.83 (dd, 1H), 7.50 (m, 3H), 7.34 (d, 2H), 7.11 (d, 1H), 7.03 (d, 2H), 6.68 (dd, 1H), 6.38 (m, 1H), 6.20 (d, 1H), 3.84, 3.78, 3.70, 3.66 (all m, 5H), 3.54, 3.49 (both m, 3H), 3.08 (br m, 4H), 2.76 (br s, 2H), 2.20 (br m, 4H), 2.14 (br m, 2H), 1.95 (br m, 2H), 1.38 (t, 2H), 1.09 (d, 3H), 0.92 (s, 6H).

Example 46

4-(4-{[2-(4-chlorophenyl)-4,4-dimethylcyclohex-1-en-1-yl]methyl}piperazin-1-yl)-N-[(4-{[(4-cyanotetrahydro-2H-pyran-4-yl)methyl]amino}-3-nitrophenyl)sulfonyl]-2-(1H-pyrrolo[2,3-b]pyridin-5-yloxy)benzamide Example 46A (4-carbamoyl-tetrahydro-pyran-4-ylmethyl)-carbamic acid tert-butyl ester 4-(Aminomethyl)tetrahydro-2H-pyran-4-carboxamide (1000 mg) was stirred in acetonitrile (30 mL) and 1-methylpyrrolidinone (10 mL). N,N-dimethylpyridin-4-amine (77 mg) was added followed by di-tert-butyl dicarbonate (1.45 g). The mixture was stirred for one hour at room temperature, and then the acetonitrile portion of the solvent was removed by evaporation at reduced pressure. The mixture was added to ethyl acetate and washed three times with water. The mixture was then washed with brine and dried on anhydrous sodium sulfate. After filtration, the solvent was removed, and the material was utilized with no further purification.

Example 46B (4-cyano-tetrahydro-pyran-4-ylmethyl)-carbamic acid tert-butyl ester EXAMPLE 46A (1.63 g) was dissolved in tetrahydrofuran (60 mL), and 1-methoxy-N-triethylammoniosulfonyl-methanimidate (1.58 g) was added. The mixture was stirred at room temperature for 16 hours. The solvent was removed under vacuum and the material taken up in ethyl acetate. The solution was washed with water three times, washed with brine, and dried on anhydrous sodium sulfate. After filtration, the solvent was removed, and the material was utilized with no further purification.

Example 46C 4-(aminomethyl)tetrahydro-2H-pyran-4-carbonitrile trifluoroacetic acid salt EXAMPLE 46B (610 mg) was dissolved in dichloromethane (20 mL). 2,2,2-Trifluoroacetic acid (1.95 mL) was added, and the mixture was stirred at room temperature for four hours. The solvent was removed under vacuum, the crude material was taken up in dichloromethane, and the solvents were removed under vacuum again. The material was then triturated with diethyl ether, and dried on vacuum.

Example 46D

4-[(4-cyano-tetrahydro-pyran-4-ylmethyl)-amino]-3-nitro-benzenesulfonamide

The title compound was prepared by substituting EXAMPLE 46C for EXAMPLE 1M in EXAMPLE 1N.

Example 46E 4-(4-{[2-(4-chlorophenyl)-4,4-dimethylcyclohex-1-en-1-yl]methyl}piperazin-1-yl)-N-[(4-{[(4-cyanotetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting EXAMPLE 46D for EXAMPLE 1N in EXAMPLE 1O. $^{1}$H NMR (300 MHz, dimethylsulfoxide-$d_6$) δ 11.66 (s, 1H), 11.37 (bs, 1H), 8.65 (t, 1H), 8.57 (d, 1H), 8.04 (d, 1H), 7.85 (dd, 1H), 7.52 (dd, 2H), 7.49 (d, 1H), 7.44 (d, 1H), 7.34 (d, 2H), 7.04 (d, 2H), 6.68 (dd, 1H), 6.38 (t, 1H), 6.20 (d, 1H), 3.92 (dd, 2H), 3.83 (d, 2H), 3.46 (t, 2H), 3.08 (s, 4H), 2.76 (s, 2H), 2.27-2.12 (m, 6H), 1.95 (s, 2H), 1.89 (d, 2H), 1.74 (td, 2H), 1.38 (t, 2H), 0.92 (s, 6H).

Example 47

N-[(4-{[(1-acetylpiperidin-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Example 47A (1-Acetyl-piperidin-4-ylmethyl)-carbamic acid tert-butyl ester Tert-butyl (piperidin-4-ylmethyl)carbamate (600 mg) was dissolved in dichloromethane (20 mL). Triethylamine (1.17 mL) was added, and acetic anhydride (0.26 mL) was added. The solution was mixed at room temperature for 16 hours, and the solvent was removed under vacuum. The material was carried on with no further purification.

Example 47B 1-(4-(aminomethyl)piperidin-1-yl)ethanone trifluoroacetic acid salt

EXAMPLE 47A (718 mg) was dissolved in dichloromethane (20 mL). 2,2,2-Trifluoroacetic acid (4.32 mL) was added, and the solution was stirred at room temperature for four hours. The solvent was removed under vacuum, the material taken up in dichloromethane, and the solvents were removed under vacuum again. The material was then triturated with diethyl ether, and dried on vacuum.

Example 47C

4-[(1-Acetyl-piperidin-4-ylmethyl)-amino]-3-nitro-benzenesulfonamide

The title compound was prepared by substituting EXAMPLE 47B for EXAMPLE 1M in EXAMPLE 1N.

Example 47D

N-[(4-{[(1-acetylpiperidin-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting EXAMPLE 47C for EXAMPLE 1N in EXAMPLE 1O. $^{1}$H NMR (300 MHz, dimethylsulfoxide-$d_6$) δ 11.68 (s, 1H), 11.35 (bs, 1H), 8.62 (t, 1H), 8.57 (d, 1H), 8.04 (d, 1H), 7.81 (dd, 1H), 7.52 (dd, 2H), 7.49 (d, 1H), 7.34 (d, 2H), 7.11 (d, 1H), 7.04 (d, 2H), 6.68 (dd, 1H), 6.39 (t, 1H), 6.19 (d, 1H), 4.38 (d, 1H), 3.81 (d, 1H), 3.07 (s, 4H), 2.98 (t, 1H), 2.75 (s, 2H), 2.48 (t, 1H), 2.24-2.11 (m, 6H), 1.98 (s, 3H), 1.95 (s, 2H), 1.88 (m, 2H), 1.72 (t, 2H), 1.38 (t, 2H), 1.22-0.98 (m, 3H), 0.92 (s, 6H).

Example 48

4-(4-{[2-(4-chloro-2-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 48A methyl 2-(4-chloro-2-fluorophenyl)-4,4-dimethylcyclohex-1-enecarboxylate The title compound was prepared by substituting 2-fluoro-4-chlorophenyl boronic acid for 4-chlorophenyl boronic acid in EXAMPLE 1B.

Example 48B (2-(4-chloro-2-fluorophenyl)-4,4-dimethylcyclohex-1-enyl)methanol

The title compound was prepared by substituting EXAMPLE 48A for EXAMPLE 1B in EXAMPLE 1C.

Example 48C 2-(4-chloro-2-fluorophenyl)-4,4-dimethylcyclohex-1-enecarbaldehyde

EXAMPLE 48B (500 mg) was dissolved in dichloromethane (19 mL), Dess-Martin periodinane (950 mg) was added and the reaction was stirred at room temperature for 2 hours. The reaction was then concentrated and and the crude material was partitioned between diethyl ether and 2M aqueous $Na_2CO_3$. The organic layer was washed with brine, dried over $Na_2SO_4$, filtered, and concentrated. The crude material was chromatographed on silica gel with 9/1 heptanes/ethyl acetate to give the title compound.

Example 48D methyl 2-(1H-pyrrolo[2,3-b]pyridin-5-yloxy)-4-(piperazin-1-yl)benzoate A mixture of EXAMPLE 1H (20.5 g) and piperazine (37.0 g) in dimethylsulfoxide (200 mL) was heated to 110° C. for 24 hours, and the mixture was allowed to cool to room temperature. The mixture was poured into water (1 L) and extracted three times with dichloromethane. The combined extracts were washed twice with water, washed with brine, filtered, and concentrated to give the title compound.

Example 48E methyl 2-(1H-pyrrolo[2,3-b]pyridin-5-yloxy)-4-(4-((2-(4-chloro-2-fluorophenyl)-4,4-dimethylcyclohex-1-enyl)methyl)piperazin-1-yl)benzoate To a solution of EXAMPLE 48C (450 mg) and EXAMPLE 48D (600 mg) in dichloromethane (6 mL) was added sodium triacetoxyborohydride (540 mg). The mixture was stirred overnight. The mixture was diluted with ethyl acetate (200 mL) and washed with saturated aqueous $NaHCO_3$, water and brine. After drying over $Na_2SO_4$, the crude material was filtered, and chromatographed on silica gel with 1/1 heptanes/ethyl acetate to give the title compound.

Example 48F 2-(1H-pyrrolo[2,3-b]pyridin-5-yloxy)-4-(4-((2-(4-chloro-2-fluorophenyl)-4,4-dimethylcyclohex-1-enyl)methyl)piperazin-1-yl)benzoic acid The title compound was prepared by substituting EXAMPLE 48E for EXAMPLE 1I in EXAMPLE 1J.

Example 48G methyl 2-(1H-pyrrolo[2,3-b]pyridin-5-yloxy)-4-(piperazin-1-yl)benzoate The title compound was prepared by substituting (tetrahydro-2H-pyran-4-yl)methanamine for EXAMPLE 1M in EXAMPLE 1N.

Example 48H 2-(1H-pyrrolo[2,3-b]pyridin-5-yloxy)-4-(4-((2-(4-chloro-2-fluorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting EXAMPLE 48F for EXAMPLE 1J and EXAMPLE 48G for EXAMPLE 1N in EXAMPLE 1O. $^1H$ NMR (400 MHz, dimethylsulfoxide-$d_6$) δ 11.68 (s, 1H), 8.61 (t, 1H), 8.56 (d, 1H), 8.04 (d, 1H), 7.80 (dd, 1H), 7.50 (m, 3H), 7.35 (dd, 1H), 7.21 (dd, 1H), 7.10 (m, 2H), 6.68 (dd, 1H), 6.39 (m, 1H), 6.20 (d, 1H), 3.85 (dd, 2H), 3.27 (m, 4H), 3.07 (br m, 4H), 2.67 (br s, 2H), 2.17 (br m, 6H), 1.90 (br m, 2H), 1.88 (m, 1H), 1.61 (dd, 2H), 1.40 (t, 2H), 1.27 (ddd, 2H), 0.92 (s, 6H).

Example 49

4-(4-{[2-(4-chloro-3-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 49A methyl 2-(4-chloro-3-fluorophenyl)-4,4-dimethylcyclohex-1-enecarboxylate The title compound was prepared by substituting 3-fluoro-4-chlorophenyl boronic acid for 4-chlorophenyl boronic acid in EXAMPLE 1B.

Example 49B (2-(4-chloro-3-fluorophenyl)-4,4-dimethylcyclohex-1-enyl)methanol

The title compound was prepared by substituting EXAMPLE 49A for EXAMPLE 1B in EXAMPLE 1C.

Example 49C 2-(4-chloro-3-fluorophenyl)-4,4-dimethylcyclohex-1-enecarbaldehyde

The title compound was prepared by substituting EXAMPLE 49B for EXAMPLE 48B in EXAMPLE 48C.

Example 49D methyl 2-(1H-pyrrolo[2,3-b]pyridin-5-yloxy)-4-(4-((2-(4-chloro-3-fluorophenyl)-4,4-dimethylcyclohex-1-enyl)methyl)piperazin-1-yl)benzoate The title compound was prepared by substituting EXAMPLE 49C for EXAMPLE 48C in EXAMPLE 48E.

Example 49E 2-(1H-pyrrolo[2,3-b]pyridin-5-yloxy)-4-(4-((2-(4-chloro-3-fluorophenyl)-4,4-dimethylcyclohex-1-enyl)methyl)piperazin-1-yl)benzoic acid The title compound was prepared by substituting EXAMPLE 49D for EXAMPLE 1I in EXAMPLE 1J.

Example 49F 2-(1H-pyrrolo[2,3-b]pyridin-5-yloxy)-4-(4-((2-(4-chloro-3-fluorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting EXAMPLE 49E for EXAMPLE 1J and EXAMPLE 48G for EXAMPLE 1N in EXAMPLE 1O. $^1H$ NMR (400 MHz, dimethylsulfoxide-$d_6$) δ 11.69 (s, 1H), 8.61 (t, 1H), 8.56 (d, 1H), 8.04 (d, 1H), 7.80 (dd, 1H), 7.50 (m, 3H), 7.32 (dd, 1H), 7.23 (dd, 1H), 7.11 (d, 1H), 7.03 (m, 1H), 6.68 (dd, 1H), 6.39 (m, 1H), 6.20 (d, 1H), 3.85 (dd, 2H), 3.27 (m, 4H), 3.07 (br m, 4H), 2.75 (br s, 2H), 2.21 (br m, 4H), 2.14 (br m, 2H), 1.96 (s, 2H), 1.89 (m, 1H), 1.61 (dd, 2H), 1.38 (t, 2H), 1.26 (ddd, 2H), 0.92 (s, 6H).

Example 50

4-(4-{[2-(4-chlorophenyl)-4,4-dimethylcyclohex-1-en-1-yl]methyl}piperazin-1-yl)-N-[(4-{[(4-ethyltetrahydro-2H-pyran-4-yl)methyl]amino}-3-nitrophenyl)sulfonyl]-2-(1H-pyrrolo[2,3-b]pyridin-5-yloxy)benzamide Example 50A 4-[(4-Ethyl-tetrahydro-pyran-4-ylmethyl)-amino]-3-nitro-benzenesulfonamide The title compound was prepared by substituting (4-ethyltetrahydro-2H-pyran-4-yl)methanamine for EXAMPLE 1M in EXAMPLE 1N.

Example 50B 4-(4-{[2-(4-chlorophenyl)-4,4-dimethylcyclohex-1-en-1-yl]methyl}piperazin-1-yl)-N-[(4-{[(4-ethyltetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting EXAMPLE 50A for EXAMPLE 1N in EXAMPLE 1O. $^1H$ NMR (300 MHz, dimethylsulfoxide-$d_6$) δ 11.68 (s, 1H), 11.37 (bs, 1H), 8.57 (d, 1H), 8.37 (t, 1H), 8.05 (d, 1H), 7.84 (dd, 1H), 7.52 (dd, 2H), 7.49 (d, 1H), 7.34 (d, 2H), 7.22 (d, 1H), 7.04 (d, 2H), 6.68 (dd, 1H), 6.39 (t, 1H), 6.19 (d, 1H), 3.68-3.52 (m, 4H), 3.35 (q, 2H), 3.07 (s, 4H), 2.76 (s, 2H), 2.25-2.11 (m, 6H), 1.95 (s, 2H), 1.55-1.35 (m, 8H), 0.92 (s, 6H), 0.82 (t, 3H).

Example 51

4-(4-{[2-(4-chlorophenyl)-4,4-dimethylcyclohex-1-en-T-yl]methyl}piperazin-1-yl)-N-({4-[(1,4-dioxepan-6-ylmethyl)amino]-3-nitrophenyl}sulfonyl)-2-(1H-pyrrolo[2,3-b]pyridin-5-yloxy)benzamide Example 51A tert-butyl 2-(1,4-dioxepan-6-ylidene)acetate To a cooled (0° C.) solution of tert-butyl 2-(diethoxyphosphoryl)acetate (16.9 g) in THF (250 mL) was added sodium hydride (60% in mineral oil, 2.7 g) in portions over 20 minutes, and the mixture was stirred for an additional 10 minutes. EXAMPLE 25A (6.5 g) in THF (10 mL) was added and the reaction mixture was stirred for 1 hour, while the temperature was allowed to rise to room temperature. The mixture was then poured into water (200 mL) and extracted with ether (2×300 mL). The combined ether extracts were washed with water and brine, dried over $Na_2SO_4$, filtered, and concentrated. Chromatography on silica gel using 10% ethyl acetate in heptanes provided the title compound.

Example 51B tert-butyl 2-(1,4-dioxepan-6-yl)acetate

EXAMPLE 51A (8.4 g) and THF (100 mL) were added to 5% Pd/C (wet JM#9, 1.6 g) in a 250 mL SS pressure bottle and the mixture was stirred for 30 minutes at 30 psi. The mixture was filtered through a nylon membrane and concentrated.

Example 51C 2-(1,4-dioxepan-6-yl)acetic acid

EXAMPLE 51B (8.4 g) was stirred in dichloromethane (100 mL)/TFA (100 mL) for 1 hour, and the mixture was concentrated to give the title compound.

Example 51D benzyl ((1,4-dioxepan-6-yl)methyl)carbamate

A solution of EXAMPLE 51C (3.88 g), diphenylphosphoryl azide (6.67 g), benzyl alcohol (5.04 mL), and triethylamine (3.4 mL) in toluene (50 mL) was stirred at 90° C. for 48 hours. The mixture was cooled and poured into water (100 mL) and extracted with ether (2×200 mL). The combined extracts were washed with water and brine, dried over $Na_2SO_4$, filtered, and concentrated. Chromatography on silica gel using 5-20% ethyl acetate in heptanes provided the title compound.

Example 51E (1,4-dioxepan-6-yl)methanamine

EXAMPLE 51D (4 g) and ethanol (60 mL) were added to 20% $Pd(OH)_2/C$ (wet, 0.4 g) in a 250 mL SS pressure bottle and the reaction mixture was stirred for 30 minutes at 30 psi and 50° C. The mixture was filtered through a nylon membrane and concentrated to give the title compound.

Example 51F 4-(((1,4-dioxepan-6-yl)methyl)amino)-3-nitrobenzenesulfonamide

The title compound was prepared by substituting EXAMPLE 51E for EXAMPLE 1M in EXAMPLE 1N.

Example 51G 4-(4-{[2-(4-chlorophenyl)-4,4-dimethylcyclohex-1-en-1-yl]methyl}piperazin-1-yl)-N-({4-[(1,4-dioxepan-6-ylmethyl)amino]-3-nitrophenyl}sulfonyl)-2-(1H-pyrrolo[2,3-b]pyridin-5-yloxy)benzamide The title compound was prepared by substituting EXAMPLE 51F for EXAMPLE 1N in EXAMPLE 1O. $^1$H NMR (300 MHz, dimethylsulfoxide-$d_6$) δ 11.68 (s, 1H), 11.35 (br s, 1H), 8.70 (m, 1H), 8.56 (s, 1H), 8.04 (s, 1H), 7.81 (d, 1H), 7.50 (m, 3H), 7.34 (d, 2H), 7.07 (d, 1H), 7.04 (d, 2H), 6.69 (d, 1H), 6.39 (d, 1H), 6.19 (s, 1H), 3.86 (dd, 2H), 3.68 (m, 4H), 3.64 (dd, 2H), 3.37 (m, 2H), 3.07 (m, 4H), 2.76 (m, 2H), 2.35 (m, 1H), 2.20 (m, 4H), 2.14 (m, 2H), 1.95 (m, 2H), 1.38 (m, 2H), 0.92 (m, 6H).

Example 52

4-(4-{[2-(4-cyclopropylphenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 52A methyl 2-(4-cyclopropylphenyl)-4,4-dimethylcyclohex-1-enecarboxylate The title compound was prepared by substituting 4-cyclopropylphenyl boronic acid for 4-chlorophenyl boronic acid in EXAMPLE 1B.

Example 52B (2-(4-cyclopropylphenyl)-4,4-dimethylcyclohex-1-enyl)methanol

The title compound was prepared by substituting EXAMPLE 52A for EXAMPLE 1B in EXAMPLE 1C.

Example 52C 2-(4-cyclopropylphenyl)-4,4-dimethylcyclohex-1-enecarbaldehyde

The title compound was prepared by substituting EXAMPLE 52B for EXAMPLE 48B in EXAMPLE 48C.

Example 52D methyl 2-(1H-pyrrolo[2,3-b]pyridin-5-yloxy)-4-(4-((2-(4-cyclopropylphenyl)-4,4-dimethylcyclohex-1-enyl)methyl)piperazin-1-yl)benzoate The title compound was prepared by substituting EXAMPLE 52C for EXAMPLE 48C in EXAMPLE 48E.

Example 52E 2-(1H-pyrrolo[2,3-b]pyridin-5-yloxy)-4-(4-((2-(4-cyclopropylphenyl)-4,4-dimethylcyclohex-1-enyl)methyl)piperazin-1-yl)benzoic acid The title compound was prepared by substituting EXAMPLE 52D for EXAMPLE 1I in EXAMPLE 1J.

Example 52F 2-(1H-pyrrolo[2,3-b]pyridin-5-yloxy)-4-(4-((2-(4-cyclopropylphenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting EXAMPLE 52E for EXAMPLE 1J and EXAMPLE 48G for EXAMPLE 1N in EXAMPLE 1O. $^1$H NMR (400 MHz, dimethylsulfoxide-$d_6$) δ 11.67 (s, 1H), 8.59 (t, 1H), 8.56 (d, 1H), 8.04 (d, 1H), 7.80 (dd, 1H), 7.50 (m, 3H), 7.09 (d, 1H), 6.97 (d, 2H), 6.87 (d, 2H), 6.68 (dd, 1H), 6.39 (m, 1H), 6.20 (d, 1H), 3.85 (dd, 2H), 3.27 (m, 4H), 3.08 (br m, 4H), 2.78 (br s, 2H), 2.20 (br m, 4H), 2.13 (br m, 2H), 1.93 (s, 2H), 1.86 (m, 2H), 1.61 (dd, 2H), 1.37 (t, 2H), 1.27 (ddd, 2H), 0.92 (s, 6H), 0.89 (m, 2H), 0.61 (m, 2H).

Example 53

4-(4-{[2-(3,4-dichlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Example 53A methyl 2-(3,4-dichlorophenyl)-4,4-dimethylcyclohex-1-enecarboxylate The title compound was prepared by substituting 3,4-dichlorophenyl boronic acid for 4-chlorophenyl boronic acid in EXAMPLE 1B.

Example 53B (2-(3,4-dichlorophenyl)-4,4-dimethylcyclohex-1-enyl)methanol

The title compound was prepared by substituting EXAMPLE 53A for EXAMPLE 1B in EXAMPLE 1C.

Example 53C 2-(3,4-dichlorophenyl)-4,4-dimethylcyclohex-1-enecarbaldehyde

The title compound was prepared by substituting EXAMPLE 53B for EXAMPLE 48B in EXAMPLE 48C.

Example 53D methyl 2-(1H-pyrrolo[2,3-b]pyridin-5-yloxy)-4-(4-((2-(3,4-dichlorophenyl)-4,4-dimethylcyclohex-1-enyl)methyl)piperazin-1-yl)benzoate The title compound was prepared by substituting EXAMPLE 53C for EXAMPLE 48C in EXAMPLE 48E.

Example 53E 2-(1H-pyrrolo[2,3-b]pyridin-5-yloxy)-4-(4-((2-(3,4-dichlorophenyl)-4,4-dimethylcyclohex-1-enyl) methyl)piperazin-1-yl)benzoic acid The title compound was prepared by substituting EXAMPLE 53D for EXAMPLE 1 in EXAMPLE 1J.

Example 53F 2-(1H-pyrrolo[2,3-b]pyridin-5-yloxy)-4-(4-((2-(3,4-dichlorophenyl)-4,4-dimethylcyclohex-1-enyl) methyl)piperazin-1-yl)-N-(3-nitro-4-((tetrahydro-2H-pyran-4-yl)methylamino)phenylsulfonyl) benzamide The title compound was prepared by substituting EXAMPLE 53E for EXAMPLE 1J and EXAMPLE 48G for EXAMPLE 1N in EXAMPLE 1O. $^1$H NMR (400 MHz, dimethylsulfoxide-$d_6$) δ 11.68 (s, 1H), 8.60 (t, 1H), 8.56 (d, 1H), 8.04 (d, 1H), 7.80 (dd, 1H), 7.52 (m, 4H), 7.29 (d, 1H), 7.11 (d, 1H), 7.02 (dd, 1H), 6.68 (dd, 1H), 6.39 (m, 1H), 6.20 (d, 1H), 3.85 (dd, 2H), 3.27 (m, 4H), 3.07 (br m, 4H), 2.76 (br s, 2H), 2.21 (br m, 4H), 2.14 (br m, 2H), 1.96 (s, 2H), 1.89 (m, 1H), 1.61 (dd, 2H), 1.38 (t, 2H), 1.26 (ddd, 2H), 0.92 (s, 6H).

Example 54

4-[4-({2-[4-(difluoromethyl)phenyl]-4,4-dimethylcyclohex-1-en-1-yl}methyl)piperazin-1-yl]-N-({3-nitro-4-[(tetrahydro-2H-pyran-4-ylmethyl)amino] phenyl}sulfonyl)-2-(1H-pyrrolo[2,3-b]pyridin-5-yloxy)benzamide Example 54A 2-(4-Difluoromethyl-phenyl)-4,4-dimethyl-cyclohex-1-enecarboxylic acid methyl ester The title compound was prepared by substituting (4-(difluoromethyl)phenyl)boronic acid for 4-chlorophenyl boronic acid in EXAMPLE 1B.

Example 54B

[2-(4-difluoromethyl-phenyl)-4,4-dimethyl-cyclohex-1-enyl]-methanol

The title compound was prepared by substituting EXAMPLE 54A for EXAMPLE 1B in EXAMPLE 1C.

Example 54C 2-(4-difluoromethyl-phenyl)-4,4-dimethyl-cyclohex-1-enecarbaldehyde

The title compound was prepared by substituting EXAMPLE 54B for EXAMPLE 48B in EXAMPLE 48C.

Example 54D

4-{4-[2-(4-Difluoromethyl-phenyl)-4,4-dimethyl-cyclohex-1-enylmethyl]-piperazin-1-yl}-2-(1H-pyrrolo[2,3-b]pyridin-5-yloxy)-benzoic acid methyl ester The title compound was prepared by substituting EXAMPLE 54C for EXAMPLE 48C in EXAMPLE 48E.

Example 54E

4-{4-[2-(4-difluoromethyl-phenyl)-4,4-dimethyl-cyclohex-1-enylmethyl]-piperazin-1-yl}-2-(1H-pyrrolo[2,3-b]pyridin-5-yloxy)-benzoic acid The title compound was prepared by substituting EXAMPLE 54D for EXAMPLE 1I in EXAMPLE 1J.

Example 54F

4-[4-({2-[4-(difluoromethyl)phenyl]-4,4-dimethylcyclohex-1-en-1-yl}methyl)piperazin-1-yl]-N-({3-nitro-4-[(tetrahydro-2H-pyran-4-ylmethyl)amino] phenyl}sulfonyl)-2-(1H-pyrrolo[2,3-b]pyridin-5-yloxy)benzamide The title compound was prepared by substituting EXAMPLE 54E for EXAMPLE 1J and EXAMPLE 48G for EXAMPLE 1N in EXAMPLE 1O. $^1$H NMR (300 MHz, dimethylsulfoxide-$d_6$) δ 11.67 (s, 1H), 11.38 (bs, 1H), 8.59 (t, 1H), 8.56 (d, 1H), 8.04 (d, 1H), 7.80 (dd, 1H), 7.53-7.47 (m, 5H), 7.16 (d, 2H), 7.11 (d, 1H), 6.99 (t, 1H), 6.68 (dd, 1H), 6.39 (t, 1H), 6.19 (d, 1H), 3.85 (dd, 2H), 3.27 (m, 4H), 3.07 (s, 4H), 2.75 (s, 2H), 2.23-2.13 (m, 6H), 1.97 (s, 2H), 1.89 (m, 1H), 1.62 (d, 2H), 1.40 (t, 2H), 1.36 (m, 2H), 0.93 (s, 6H).

Bcl-2 Binding Data

Determination of the utility of compounds of this invention as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmoc-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with DCM and kept wet. 150 mL of 95:4:1 dichloromethane: triisopropylsilane:trifluoroacetic acid was flowed through the resin bed over 30 minutes. The mixture turned deep yellow then faded to pale yellow. 100 mL of DMF was flowed through the bed over 15 minutes. The resin was then washed thrice with DMF and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% DIEA/DMF and stirred or shaken at ambient temperature overnight. When complete, the resin was drained, washed thrice with DMF, thrice with (1×DCM and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, Calif.) on a 4.6×250 mm YMC column packed with ODS-AQ 5 μm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe Acetyl-(SEQ ID NO: 1)GQVGRQLAIIGDK(6-FAM)-INR-$NH_2$

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 $[(M+H)^+]$.

Alternative Synthesis of Peptide Probe F-Bak: Acetyl-(SEQ ID NO: 1)GQVGRQLAIIGDK(6-FAM)-INR-$NH_2$ The protected peptide was assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in DMF and confirmed complete by ninhydrin testing. The peptide was cleaved from the resin and side-chains deprotected by treating with 80:5:5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 $((M+H)^+)$).

Time Resolved-Fluorescence Resonance Energy Transfer (TR-FRET) Assay

Representative compounds were serially diluted in dimethyl sulfoxide (DMSO) starting at 50 μM (2× starting concentration; 10% DMSO) and 10 μL were transferred into a 384-well plate. Then 10 μL of a protein/probe/antibody mix was added to each well at final concentrations listed in TABLE 1. The samples are then mixed on a shaker for 1 minute and incubated for an additional 3 hours at room temperature. For each assay, the probe/antibody and protein/probe/antibody were included on each assay plate as negative and positive controls, respectively. Fluorescence was measured on the Envision (Perkin Elmer) using a 340/35 nm excitation filter and 520/525 (F-Bak peptide) and 495/510 nm (Tb-labeled anti-Histidine antibody) emission filters. Dissociation constants ($K_i$) are shown in TABLE 2 below and were determined using Wang's equation (Wang Z.-X., An Exact Mathematical Expression For Describing Competitive Binding Of Two Different Ligands To A Protein Molecule. *FEBS Lett.* 1995, 360:111-4).

TABLE 1

Protein, Probe And Antibody Used For TR-FRET Assays

| Protein | Probe | Protein (nM) | Probe (nM) | Antibody | Antibody (nM) |
|---|---|---|---|---|---|
| GST-Bcl-2 | F-Bak Peptide Probe Acetyl-(SEQ ID NO: 1 GQVGRQLAIIGDK(6-FAM)-INR-amide) | 1 | 100 | Tb-anti-GST | 1 |

6-FAM = 6- carboxyfluorescein.; Tb = terbium; GST = glutathione S-transferase

The samples were then mixed on a shaker for 1 minute and incubated for an additional 3 hours at room temperature. For each assay, the probe/antibody and protein/probe/antibody were included on each assay plate as negative and positive controls, respectively. Fluorescence was measured on the Envision (Perkin Elmer) using a 340/35 nm excitation filter and 520/525 (F-Bak peptide) and 495/510 nm (Tb-labeled anti-Histidine antibody) emission filters.

Inhibition constants ($K_i$) for compounds were determined using Wang's equation (Wang Zx. An Exact Mathematical Expression For Describing Competitive Binding Of Two Different Ligands To A Protein Molecule. *FEBS Lett.* 1995, 360:111-4). Where the $K_i$ for a compound is represented as "<" (less than) a certain numerical value, it is intended to mean that the binding affinity value (e.g., for Bcl-2) is lower than the limit of detection of the assay used. Inhibition constants ($K_i$) for compounds of the invention are shown in Table 2.

TABLE 2

TR-FRET Bcl-2 Binding $K_i$ (nM)

| EXAMPLE | Ki (nM) |
|---|---|
| 1 | <0.1 |
| 2 | 0.1 |
| 3 | <0.1 |
| 4 | <0.1 |
| 5 | <0.1 |
| 6 | <0.1 |
| 7 | 0.1 |
| 8 | 0.7 |
| 9 | <0.1 |
| 10 | <0.1 |
| 11 | <0.1 |
| 12 | <0.1 |
| 13 | 0.1 |
| 14 | <0.1 |
| 15 | <0.1 |
| 16 | <0.1 |
| 17 | 0.1 |
| 18 | <0.1 |
| 19 | 0.1 |
| 20 | <0.1 |

TABLE 2-continued

TR-FRET Bcl-2 Binding $K_i$ (nM)

| EXAMPLE | Ki (nM) |
|---|---|
| 21 | <0.1 |
| 22 | <0.1 |
| 23 | <0.1 |
| 24 | <0.1 |
| 25 | <0.1 |
| 26 | <0.1 |
| 27 | <0.1 |
| 28 | <0.1 |
| 29 | <0.1 |
| 30 | <0.1 |
| 31 | <0.1 |
| 32 | <0.1 |
| 33 | <0.1 |
| 34 | <0.1 |
| 35 | <0.1 |
| 36 | <0.1 |
| 37 | <0.1 |
| 38 | <0.1 |
| 38 | <0.1 |
| 40 | <0.1 |
| 41 | <0.1 |
| 42 | <0.1 |
| 43 | <0.1 |
| 44 | <0.1 |
| 45 | <0.1 |
| 46 | <0.1 |
| 47 | <0.1 |
| 48 | 0.1 |
| 49 | 0.1 |
| 50 | 0.1 |
| 51 | <0.1 |
| 52 | 0.1 |
| 53 | 0.2 |
| 54 | nd |

nd = no data

The inhibition constant ($K_i$) is the dissociation constant of an enzyme-inhibitor complex or a protein/small molecule complex, wherein the small molecule is inhibiting binding of one protein to another protein or peptide. So a large $K_i$ value indicates a low binding affinity and a small $K_i$ value indicates a high binding affinity. TABLE 2 shows inhibition constants for the inhibition of a Bak BH3 peptide probe to Bcl-2 protein and indicate that compounds according to the invention have high binding affinities for anti-apoptotic Bcl-2 protein. The compounds are therefore expected to have utility in treatment of diseases during which anti-apoptotic Bcl-2 protein is expressed.

Biological Data

RS4;11 Cell Viability Assay

The acute lymphoblastic leukemia (ALL) cell line RS4;11 was used as the primary human cell line to assess the cellular activity of Bcl-2 selective agents in vitro and their efficacy in vivo. Previous studies have shown by BH3 profiling, a mitochondrial assay that classifies blocks in the intrinsic apoptotic pathway, that RS4;11 cells were highly dependant on BCL-2 for survival and sensitive to the Bcl-2 family member inhibitor ABT-737 (Blood, 2008, Vol. 111, 2300-2309). The prevalence of Bcl-2 complexed to the proapoptotic BH3 protein Bim in RS4;11 suggests that these cells are "primed" or more susceptible to cell death by antagonism of the antiapoptotic protein Bcl-2 for which they depend on for survival.

RS4;11 cells were cultured in RPMI-1640 supplemented with 2 mM L-glutamine, 10% FBS, 1 mM sodium pyruvate, 2 mM HEPES, 1% penicillin/streptomycin (Invitrogen), 4.5 g/L glucose and maintained at 37 C containing 5% $CO_2$. To test for the cellular activity of compounds in vitro, cells were treated at 50,000 cells per well in 96-well microtiter plates in the presence of 10% human serum for 48 hours in a humidified chamber with 5% $CO_2$. Cell cytotoxicity $EC_{50}$ values were assessed using CellTiter Glo (Promega) according to the manufacturer's recommendations. The $EC_{50}$ values were determined as a percentage of viable cells following treatment compared to the untreated control cells.

TABLE 3

RS4; 11 $EC_{50}$ Values (μM)

| EXAMPLE # | $EC_{50}$ (μM) |
|---|---|
| 1 | 0.0053 |
| 2 | 0.16 |
| 3 | 0.15 |
| 4 | 0.057 |
| 5 | 0.0052 |
| 6 | 0.0076 |
| 7 | 0.0068 |
| 8 | >1.0 |
| 9 | 0.0022 |
| 10 | 0.0081 |
| 11 | 0.015 |
| 12 | 0.030 |
| 13 | 0.13 |
| 14 | 0.010 |
| 15 | 0.0093 |
| 16 | 0.067 |
| 17 | 0.085 |
| 18 | 0.047 |
| 19 | 0.014 |
| 20 | 0.019 |
| 21 | 0.019 |
| 22 | 0.028 |
| 23 | 0.023 |
| 24 | 0.014 |
| 25 | 0.036 |
| 26 | 0.044 |
| 27 | 0.097 |
| 28 | 0.12 |
| 29 | 0.057 |
| 30 | 0.027 |
| 31 | 0.016 |
| 32 | 0.043 |
| 33 | 0.044 |
| 34 | 0.013 |
| 35 | 0.012 |
| 36 | 0.032 |
| 37 | 0.25 |
| 38 | 0.030 |
| 39 | 0.040 |
| 40 | 0.076 |
| 41 | 0.047 |
| 42 | 0.056 |
| 43 | 0.031 |
| 44 | 0.0047 |
| 45 | 0.019 |
| 46 | 0.0069 |
| 47 | 0.014 |
| 48 | 0.0033 |
| 49 | 0.046 |
| 50 | 0.052 |
| 51 | 0.039 |
| 52 | 0.016 |
| 53 | 0.046 |
| 54 | 0.0099 |

TABLE 3 shows the utility of compounds of this invention to functionally inhibit anti-apoptotic Bcl-2 protein in a cellular context. The acute lymphoblastic leukemia (ALL) cell line RS4;11 has been shown by BH3 profiling, a mitochondrial assay that classifies blocks in the intrinsic apoptotic pathway, to be highly dependant on Bcl-2 for survival and is sensitive to the Bcl-2 family member inhibitor ABT-737 (*Blood,* 2008, Vol. 111, 2300-2309). The ability of compounds to kill RS4;11 cells is a direct measure of the compounds ability to inhibit anti-apoptotic Bcl-2 protein function. Compounds of this invention are very effective in killing RS4;11 cells as demonstrated by low $EC_{50}$ values.

It is known within the art that inhibition of certain members of the Bcl-2 family of proteins may induce dose-limiting thrombocytopenia. The dose-limiting thrombocytopenia that severely limited the therapeutic use of some non-selective Bcl-2 inhibitors for autoimmune indications is thought to be due to inhibition of Bcl-$x_L$ (See Mason, K. D., et al., *Programmed anuclear cell death delimits platelet life span.* Cell, 2007. 128(6): p. 1173-86.

An experiment was performed to evaluate the effect of Bcl-2 selective/Bcl-$x_L$ sparing compounds on immune cells and platelets, as evaluated in C57Bl/6 mice. Mice were treated four days with compounds (doses of 30 mg/kg, administered by intraperitoneal injection every day) and cell numbers were measured with a Cell Dyn hematology analyzer 24 hours after the first and last doses. Exposure of the compound (area under the curve) was calculated by using time points of 1, 6, 10 and 24 hours after the last dose. The results of this experiment are illustrated in Table 4.

TABLE 4

Lymphocyte Reduction in C57BL/6 Mice Treated with 1 and 4 Doses of a Bcl-2 Selective Inhibitor (30 mg/kg)

| EXAMPLE # | % inh. day 1 | % inh. day 4 |
|---|---|---|
| 1 | 41 | 41 |
| 2 | <15 | <15 |
| 3 | <15 | <15 |
| 5 | 47 | 45 |
| 6 | <15 | 24 |
| 7 | 64 | 55 |
| 9 | 69 | 58 |
| 10 | <15 | <15 |
| 12 | 41 | 27 |
| 14 | 61 | 54 |
| 15 | <15 | <15 |
| 16 | <15 | <15 |
| 18 | <15 | 25 |
| 19 | 49 | 45 |
| 20 | 20 | 57 |
| 21 | 61 | 61 |
| 22 | 40 | 44 |
| 23 | 37 | 15 |
| 24 | 48 | 58 |
| 25 | 29 | 15 |
| 26 | 38 | 23 |
| 27 | 23 | 21 |
| 31 | 53 | 55 |
| 34 | <15 | 61 |
| 35 | 54 | 49 |
| 36 | 47 | 42 |
| 37 | 28 | 22 |
| 44 | 66 | 60 |
| 46 | 46 | 35 |
| 48 | 76 | 78 |
| 52 | 54 | 51 |

nd = no decrease of lymphocytes

These data are consistent with the in vitro selectivity profile and underscore the essential role of Bcl-2 on lymphocyte and Bcl-$x_L$ on platelet survival respectively. This pharmacodynamic study illustrates the ability of these compounds as selective Bcl-2 inhibitors to effectively reduce lymphocytes, without the adverse effects associated with non-selective Bcl-2 inhibitors.

What is claimed is:

1. The compound 4-(4-{[2-(4-chloro-2-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide or a therapeutically acceptable salt thereof.

* * * * *

UNITED STATES PATENT AND TRADEMARK OFFICE

CERTIFICATE OF CORRECTION

PATENT NO. : 10,081,628 B2
APPLICATION NO. : 15/276872
DATED : September 25, 2018
INVENTOR(S) : Tao et al.

It is certified that error appears in the above-identified patent and that said Letters Patent is hereby corrected as shown below:

In the Specification

Column 15, Line 28, delete "camphorsufonate" and insert therefor --camphorsulfonate--.

Column 17, Line 15, delete "proteosome" and insert therefor --proteasome--.

Column 18, Line 25, delete "rofosfamide" and insert therefor --trofosfamide--.

Column 19, Line 24, delete "petuzumab" and insert therefor --pertuzumab--.

Column 19, Line 53, delete "lesaurtinib" and insert therefor --lestaurtinib--.

Column 20, Line 36, delete "dexrazoxine" and insert therefor --dexrazoxane--.

Column 20, Line 47, delete "trastuzimab" and insert therefor --trastuzumab--.

Column 20, Line 58, delete "megesterol" and insert therefor --megestrol--.

Column 21, Line 26, delete "sargaramostim" and insert therefor --sargramostim--.

Column 21, Line 43, delete "ratitrexed" and insert therefor --raltitrexed--.

Column 22, Line 10, delete "combrestatin" and insert therefor --combretastatin--.

Column 22, Line 17, delete "epithilone" and insert therefor --epothilone--.

Column 22, Line 55, delete "zolendronic acid" and insert therefor --zoledronic acid--.

Column 24, Line 11, delete "chloroquinine" and insert therefor --chloroquine--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

Column 24, Line 13, delete “cochicine” and insert therefor --colchicine--.

Column 24, Line 20, delete “adensosine” and insert therefor --adenosine--.

Column 24, Line 57, delete “budenoside” and insert therefor --budesonide--.

Column 25, Line 5, delete “fonotolizumab” and insert therefor --fontolizumab--.

Column 27, Line 16, delete “lymphangioendothelio” and insert therefor --lymphangioendothelioma--.

Column 27, Line 55, delete “psteosarcoma” and insert therefor --osteosarcoma--.

Column 27, Line 67, delete “abetalipoprotemia” and insert therefor --abetalipoproteinemia--.

Column 28, Line 32, delete “choleosatatis” and insert therefor --cholestasis--.

Column 28, Line 60, delete “hematophagocytic” and insert therefor --hemophagocytic--.

Column 29, Line 3, delete “haemosiderosis” and insert therefor --hemosiderosis--.

Column 29, Line 4, delete “Hallerrorden” and insert therefor --Hallervorden--.

Column 29, Line 6, delete “hemachromatosis” and insert therefor --hemochromatosis--.

Column 29, Line 15, delete “leucopaenia” and insert therefor --leukopenia--.

Column 29, Line 26, delete “lipidema” and insert therefor --lipedema--.

Column 29, Line 27, delete “lymphederma” and insert therefor --lymphedema--.

Column 29, Line 39, delete “myelodyplastic” and insert therefor --myelodysplastic--.

Column 29, Line 46, delete “epidydimitis” and insert therefor --epididymitis--.

Column 29, Line 67, delete “Raynoud’s” and insert therefor --Raynaud’s--.

Column 30, Line 9, delete “Sjörgren’s” and insert therefor --Sjögren’s--.

Column 30, Line 12, delete “spondyloarthopathy” and insert therefor --spondyloarthropathy--.

Column 30, Line 36, delete “hemaphagocytic” and insert therefor --hemophagocytic--.

Column 65, Line 35, delete “cycanoborohydride” and insert therefor --cyanoborohydride--.